(12) United States Patent
Chou et al.

(10) Patent No.: US 12,169,167 B2
(45) Date of Patent: *Dec. 17, 2024

(54) DEVICES AND METHODS FOR TISSUE AND CELL STAINING (II)

(71) Applicant: Essenlix Corporation, Monmouth Junction, NJ (US)

(72) Inventors: Stephen Y. Chou, Princeton, NJ (US); Wei Ding, Princeton, NJ (US); Ji Li, Princeton, NJ (US); Shengjian Cai, Bridgewater, NJ (US); Yu Sun, Basking Ridge, NJ (US)

(73) Assignee: Essenlix Corporation, Monmouth Junction, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/422,444

(22) PCT Filed: Feb. 19, 2020

(86) PCT No.: PCT/US2020/018871
§ 371 (c)(1),
(2) Date: Jul. 12, 2021

(87) PCT Pub. No.: WO2020/150751
PCT Pub. Date: Jul. 23, 2020

(65) Prior Publication Data
US 2022/0042884 A1 Feb. 10, 2022

Related U.S. Application Data

(60) Provisional application No. 62/792,883, filed on Jan. 15, 2019.

(51) Int. Cl.
G01N 31/00 (2006.01)
G01N 1/31 (2006.01)
G01N 33/53 (2006.01)
G01N 33/543 (2006.01)
G01N 33/569 (2006.01)

(52) U.S. Cl.
CPC ....... *G01N 1/312* (2013.01); *G01N 33/54366* (2013.01); *G01N 33/56927* (2013.01)

(58) Field of Classification Search
None
See application file for complete search history.

(56) References Cited

U.S. PATENT DOCUMENTS

| | | | |
|---|---|---|---|
| 8,007,743 B2 | 8/2011 | Clark et al. | |
| 9,268,988 B2 | 2/2016 | Benkley, III | |
| 9,354,199 B2 | 5/2016 | Selden et al. | |
| 11,274,996 B2* | 3/2022 | Chou | C12Q 1/24 |
| 11,326,989 B2* | 5/2022 | Chou | G01N 21/645 |
| 2016/0169923 A1 | 6/2016 | Holmes et al. | |
| 2018/0246089 A1* | 8/2018 | Chou | G01N 1/2813 |

OTHER PUBLICATIONS

Written Opinion of the International Searching Authority for PCT/US2020/018871 established by the ISA/US completed on Jul. 23, 2020.

* cited by examiner

*Primary Examiner* — Lisa V Cook

(57) ABSTRACT

Disclosed are devices, kits, apparatus, and methods for rapid homogenous cell staining and imaging.

43 Claims, 36 Drawing Sheets

DEVICES AND METHODS FOR TISSUE AND CELL STAINING (II)

CROSS-REFERENCE TO RELATED APPLICATIONS

This application is a National Stage entry (§ 371) application of International Application No. PCT/US2020/018871, filed on Feb. 19, 2020, which claims the benefit of priority to U.S. Provisional Application No. 62/792,883, filed Jan. 15, 2019, which is relied upon and incorporated herein by reference in its entirety. The entire disclosure of any publication or patent document mentioned herein is entirely incorporated by reference.

FIELD

Among other things, the present invention is related to devices and methods of performing rapid staining and imaging of cells and/or tissues, such as but not limited to immunoassays and dye staining.

BACKGROUND

There are needs to have rapid cell staining and imaging, and/or need to use a cell-phone to perform such. Tissue sections are broadly used in biological research, preclinical and clinical diagnosis, especially play an important role in the microscopic analysis of specimens during surgery. Standard immunohistochemistry (IHC) and immunofluorescence (IF) staining methods on tissue sections are normally take 2-4 hrs. Development of technology to accelerate standard procedure is pivotal for fast diagnosis. For example, microfluidic technologies have advanced staining procedure from 2-4 hrs to less than 12 min and a few microfluidic devices have been used in tissue diagnostics. Although this technology shortens whole staining procedure to a significant level, multiple staining step preparation is still needed and the preparation still follows standard IHC or IF method, hence still taking long time. The present invention makes the total time of a sample staining and other preparations of a tissue sample ready for imaging significantly less than the traditional methods.

SUMMARY OF INVENTION

Among other things, the present invention provides devices, kits, apparatus, and methods for rapid homogenous cell staining and imaging. Particularly, in some embodiments, the present invention can immunochemically stain a cell or a tissue in less than 60 seconds without washing.

One aspect of the present invention is to use QMAX card with dry reagent on the sample contact area of one or both plates to stain a sample (e.g. cells or tissues)

Another aspect of the present invention is to use the QMAX card to configure the thickness of the sample into a thin layer to reduce background signal, so that the stained cells become observable without any washing and/or without opening up the two plates of QMAX card. The unbound labeled detection agents (i.e. those are not bound to the target cells) in a sample are a major source of the background optical signal. The detection agent can be protein or nucleic acid.

Another aspect of the present invention is to use the QMAX card to configure the thickness of the sample into a thin layer, so that the stained cells do not substantially overlap in the direction normal to the sample thickness, which can allow a stained cell being viewed from top of the QMAX card without being substantially blocked by other stained cells.

Another aspect of the present invention is to increase an optical signal (i.e. light signal) from a stained cell) by unselectively stain the cells in the sample by other dye that emit light in the same wavelength as that of the dye that selectively stained the cell. The addition (i.e. combination) of the optical signal can make the selectively stained cell observable (i.e. distinguishable from the other part of the sample), even without washing away unbonded optical labels in the sample from the background of the sample. In some embodiments, the stained cells are either in a liquid or in a tissue.

Another aspect of the present invention is to use a second labeled antibody to stain the target cells, where the second labeled antibody selectively attaches to another epitope of the target binding site, and has an optical label emit light of wavelength overlap with that of the first labeled antibody.

Another aspect of the present invention to use a combination or multiple labeled antibody, labeled probe, dye to stain the target cells, where multiple labeled antibody, labeled probe, dye label emit light of wavelength overlap with that of the first labeled antibody. Another aspect of the present invention is to do grain staining. Another aspect of the present invention is to do immune staining.

Another aspect of the present invention is to do RNA fluorescence in situ hybridization (RNA-FISH) staining.

BRIEF DESCRIPTION OF THE DRAWINGS

The skilled artisan will understand that the drawings, described below, are for illustration purposes only. The drawings are not intended to limit the scope of the present teachings in any way. In some Figures, the drawings are in scale. In the figures that present experimental data points, the lines that connect the data points are for guiding a viewing of the data only and have no other means.

DETAILED DESCRIPTION OF EXEMPLARY EMBODIMENTS

Figure 1:
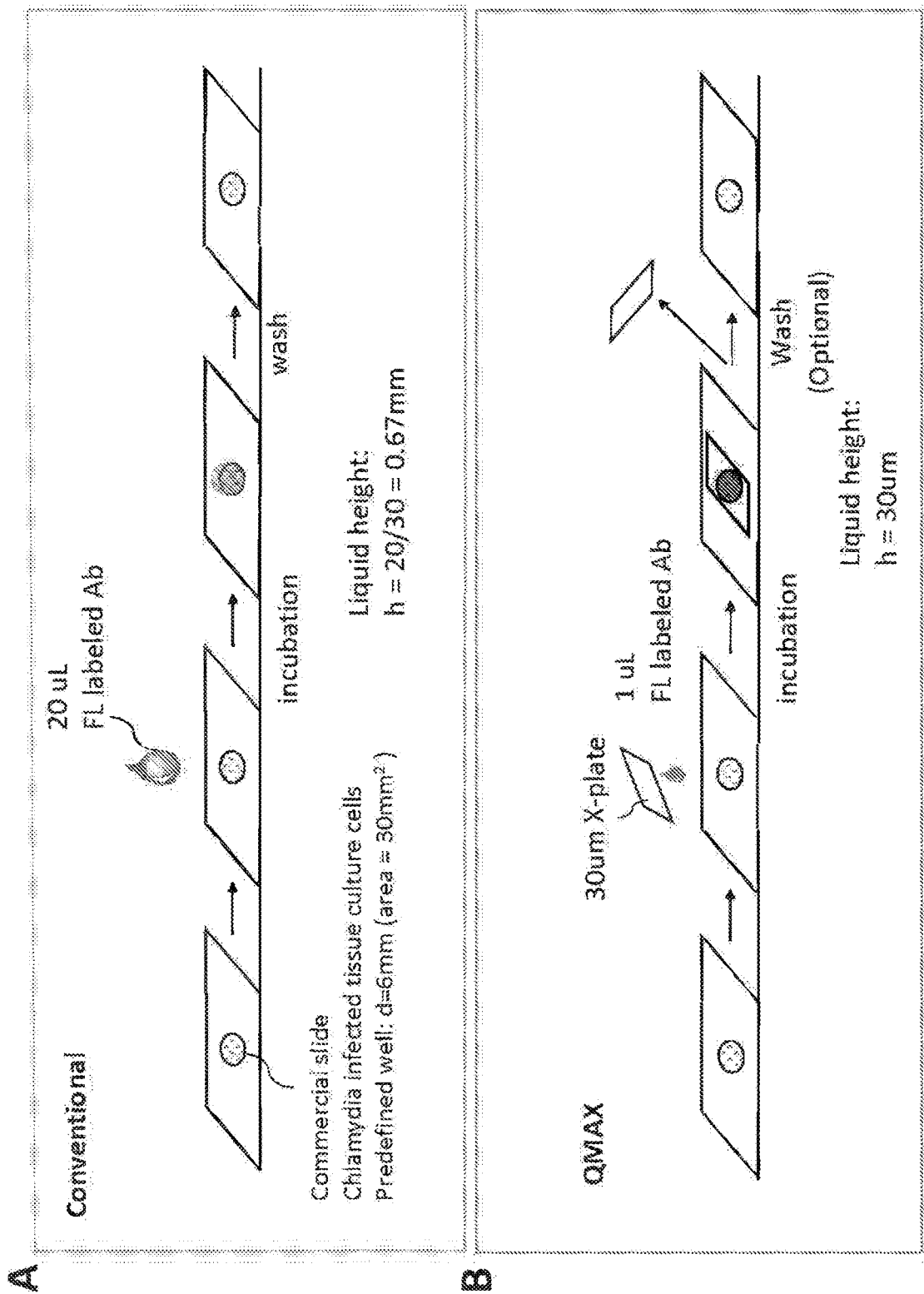
FIG. 1 provides schematic illustrations showing the processes for staining of chlamydia infected cells. Panel (A) shows the conventional method (prior art); panel (B) shows an embodiment of the present invention, where a QMAX device is employed.

The following detailed description illustrates some embodiments of the invention by way of example and not by way of limitation. If any, the section headings and any subtitles used herein are for organizational purposes only and are not to be construed as limiting the subject matter described in any way. The contents under a section heading and/or subtitle are not limited to the section heading and/or subtitle, but apply to the entire description of the present invention.

It should be noted that the Figures do not intend to show the elements in strict proportion.

For clarity purposes, some elements are enlarged when illustrated in the Figures. The dimensions of the elements should be delineated from the descriptions herein provided and incorporated by reference.

A. Fast Tissue Staining for Imaging without Washing

One aspect of the present invention is to make the total time of from a sample staining and other preparation of a tissue sample to being ready for imaging significantly less than the traditional methods.

In some embodiments of the present invention, a method of fast tissue staining a cell in a tissue for imaging comprises:
 (a) having a tissue containing or suspected of containing a target cell to be analyzed;
 (b) depositing the tissue sample on a solid phase (e.g., a surface of a plate);
 (c) having a X-Plate;
 (d) having a staining solution sandwiched between the tissue sample surface and the X-plate, wherein the stain solution stains specifically at last part of the target cell; wherein the X-plate comprises one or more spacers on its inner surface (the surface closed to the tissue); wherein the X-plate and the solid phase are movable to each other into a different configuration, said different configuration includes an open configuration and a closed configuration; wherein, in the open configuration, the two plates are partially or entirely separated, the spacing between the plates is not regulated by the spacers, and the tissue is deposited on one or both of the plates; wherein in the closed configuration, which is configured after deposition of the tissue in the open configuration, a staining solution layer sandwiched between the tissue sample surface and the second plate, wherein the thickness of the staining solution layer is regulated by the tissue sample surface, the second plate, and the spacers; wherein the thickness of the stain solution layer is configured to have, at a closed configuration, a thickness that the stained cell or any part of the cell being stained is visible without out removing (e.g. washing away) the staining solution layer between the tissue and the second plate. The stained cells can be viewed by an imager.

In an embodiment, the disclosure provides a device for fast staining cells in a tissue, comprising: a first plate, a second plate, and spacers, wherein:
 i. the first and the second plate are movable relative to each other into a different configuration, said different configuration includes an open configuration and a closed configuration;
 ii. one or both of the first and second plates is flexible;
 iii. the first plate has, on its inner surface, a tissue contact area for contacting a tissue containing or suspected of containing a target cell to be analyzed; and
 iv. the second plate (also termed X-plate) comprises the spacers fixed on its inner surface, atleast one of the spacers, the spacers have a predetermined substantially uniform height that is equal to 300 µm or less;
  wherein, in the open configuration, the two plates are partially or entirely separated, the spacing between the plates is not regulated by the spacers, and the tissue is deposited on one or both of the plates;
  wherein in the closed configuration, which is configured after deposition of the tissue in the open configuration, a staining solution layer sandwiched between the tissue sample surface and the second plate, wherein the thickness of the staining solution layer is regulated by the tissue sample surface, the second plate, and the spacers;
  wherein the thickness of the stain solution layer is configured to have, at a closed configuration, a thickness that the stained cell or any part of the cell being stained is visible without out removing (e.g. washing away) the staining solution layer between the tissue and the second plate; and
  wherein the stain solution stains specifically at last part of the target cell.

In an embodiment, the staining includes staining a cell by any staining methods, including, not limited to by color dye or by Standard immunohistochemistry (IHC), immunofluorescence (IF) and nucleic acid staining. The one or both plates can be flexible to conform the surface of the tissue.

Example-1

Material

Fresh human skin and lung cryo-sections are from Zyagen, tissue sections are stored at −80° C. before use. Antibodies used in this study are all commercially prelabelled with Alexa Flour 488 (AF488) or Alexa Flour 647 (AF647) antibodies. Alexa Fluor family of fluorescent dyes is a series of dyes invented by Molecular Probes, now a part of ThermoFisher Scientific, and sold under the Invitrogen brand name. Alexa Fluor dyes are frequently used as cell and tissue labels in fluorescent microscopy and cell biology. Alexa Fluor dyes can be conjugated directly to primary antibodies or to secondary antibodies to amplify signal and sensitivity of other biomolecules. Commercial prelabelled antibodies used in this study are Lamin A/C-AF488 (from Cell Signaling, cat no. 8617S), Elastin-AF647 (from Santa Cruz, cat no. sc-58756 AF647), cytokeratin 14-AF488 (from CK14-AF488, Nevus Biologicals, cat no. NBP2-34675AF488) and 5 IgG-AF488 (from Thermo Fisher Scientific, cat no. Z25002) and IgG-AF647 (from Thermo Fisher Scientific, cat no. Z25008). All antibodies are saved at 4° C. protective from light before use. X plates are manufactured in Essenlix Coop. X-Plate is 175 um thick PMMA with a pillar array of 30 um×40 um pillar size, 5 um pillar height and 80 um inter space distance.

Immunofluorescence (IF) Staining in Microvolume Embodiment

Figure 33:
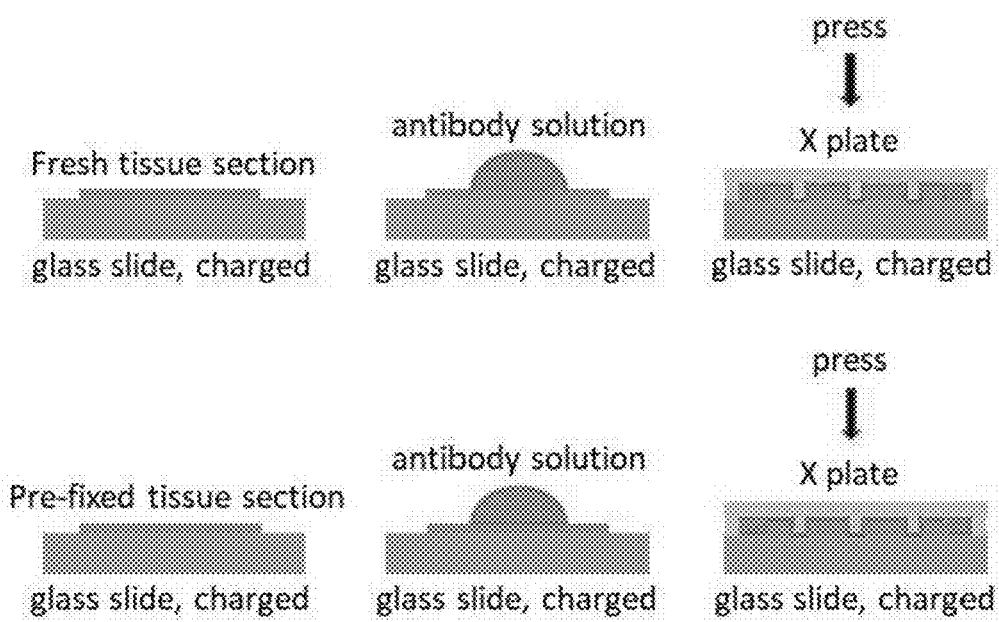
FIG. 33 is a schematic of an experimental procedure for generation of a microvolume comprising charging a slide with a fresh or pre-fixed tissue section and a flexible X plate. Drop an antibody solution on fresh cryo-tissue sections (upper panel) or prefixed tissue sections (lower panel), and gently pressing the X plate on tissue and incubate at room temperature for 1 min. A fluorescent signal was immediately observed and taken under fluorescent microscope.

Concentration of each antibody was first determined using Nanodrop One microvolume spectrophotometer (Thermal Fisher Scientific). 0.2 μg of each antibody was then diluted in 6 ul of PBS for IF staining. Drop 6 ul antibody solution on skin or lung section, gently press X plate to let antibody solution evenly distribute on tissue section, this generate a microvolume embodiment between X plate and charged glass slide. Incubate at room temperature for 1 min and observe fluorescent signal under microscope (FIG. 33).

Results

Figure 34:
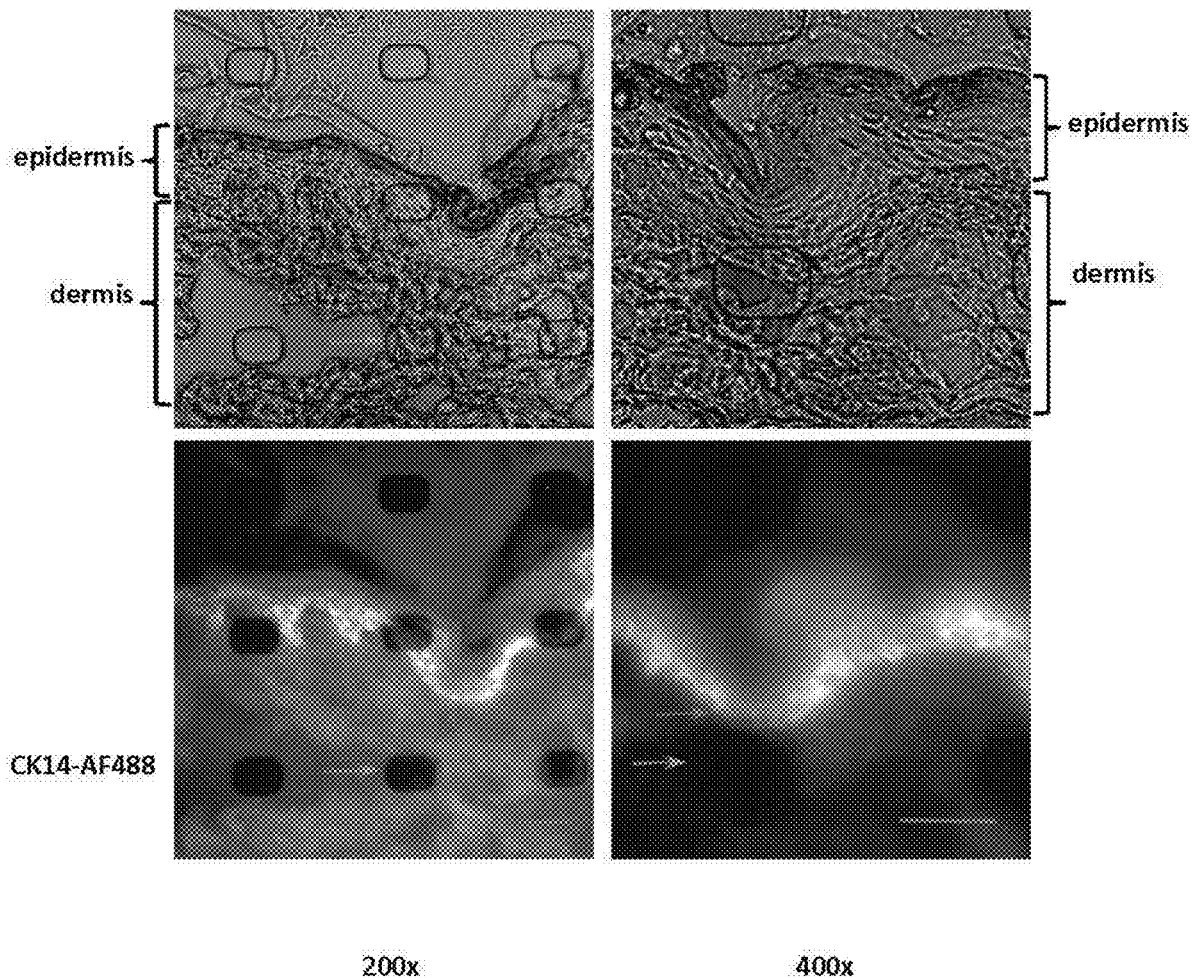
FIG. 34 shows a CK14-AF488 direct staining on fresh human skin sections. Drop 6 ul of premixed 0.2 µg CK14-AF488 (Novus Biologicals, cat no. NBP2-34675AF488) and PBS solution on fresh human skin cryosections, gently press 5 um pillar height X plate on tissue and incubate at room temperature for 1 min. Fluorescent signal was immediately taken under fluorescent microscope. Upper panel are bright filed images show epidermis and dermis of skin. Lower panel are fluorescent images with 200× or 400× amplification. Bright signals pointed with red arrows indicate CK14-AF488 positive cells are basal layer epidermal cells. Image with 400×shows membrane and cytosolic staining of CK14-AF488. Green arrow in each image points at the 5 um height pillar on X plate and red line is 40 um scale bar.
Figure 35:
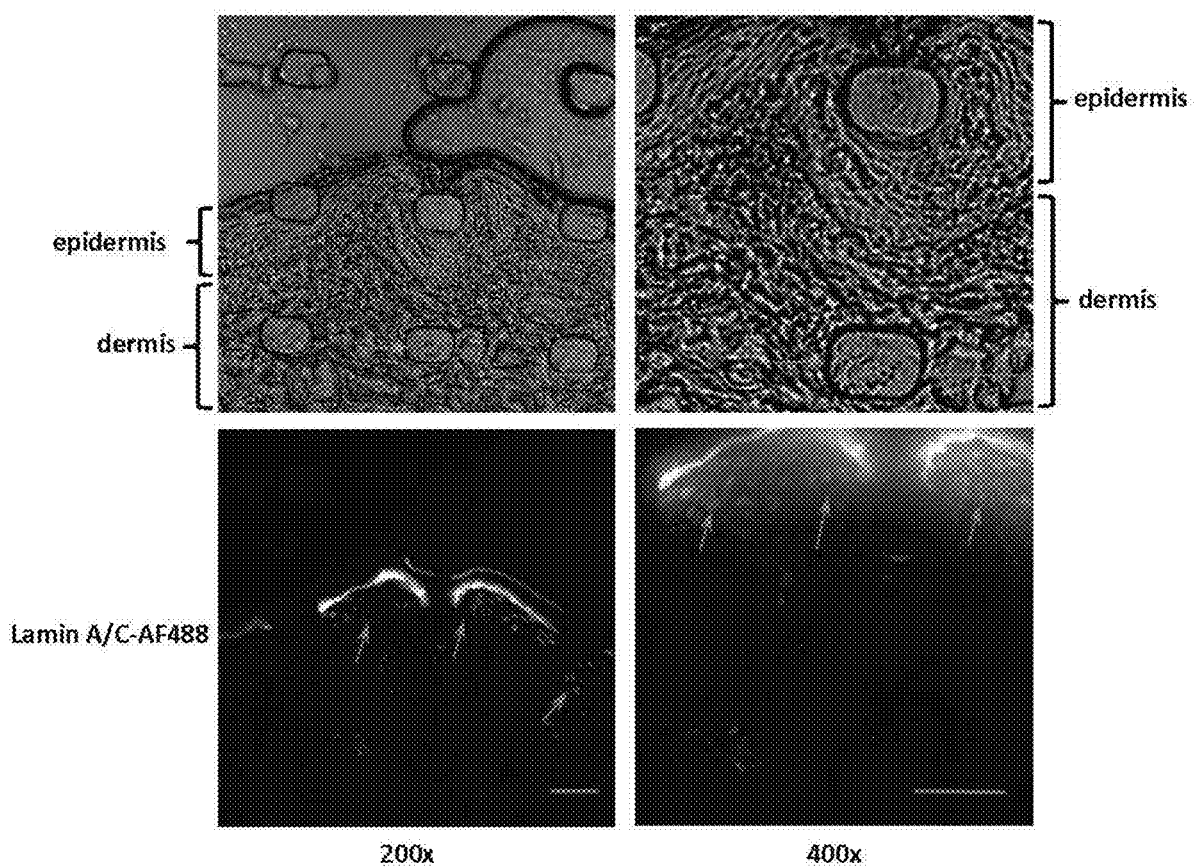
FIG. 35 shows Lamin A/C-AF488 direct staining on fresh human skin sections. Drop 6 ul of premixed 0.2 µg Lamin A/C-AF488 (Cell Signaling, cat no. 8617S) and PBS solution on fresh human skin cryosections, gently press 5 um pillar height X plate on tissue and incubate at room temperature for 1 min. Fluorescent signal was immediately taken under fluorescent microscope. Upper panel are bright filed images show epidermis and dermis of skin as indicated. Lower panel are fluorescent images. The bright signals pointed with red arrows indicate suprabasal epidermal cells are positive for Lamin A/C-AF488 staining. Image with 400×amplification shows nuclear staining of Lamin A/C-AF488. Green arrow in each image points at the 5 um height pillar on X plate and red line is 40 um scale bar.
Figure 36:
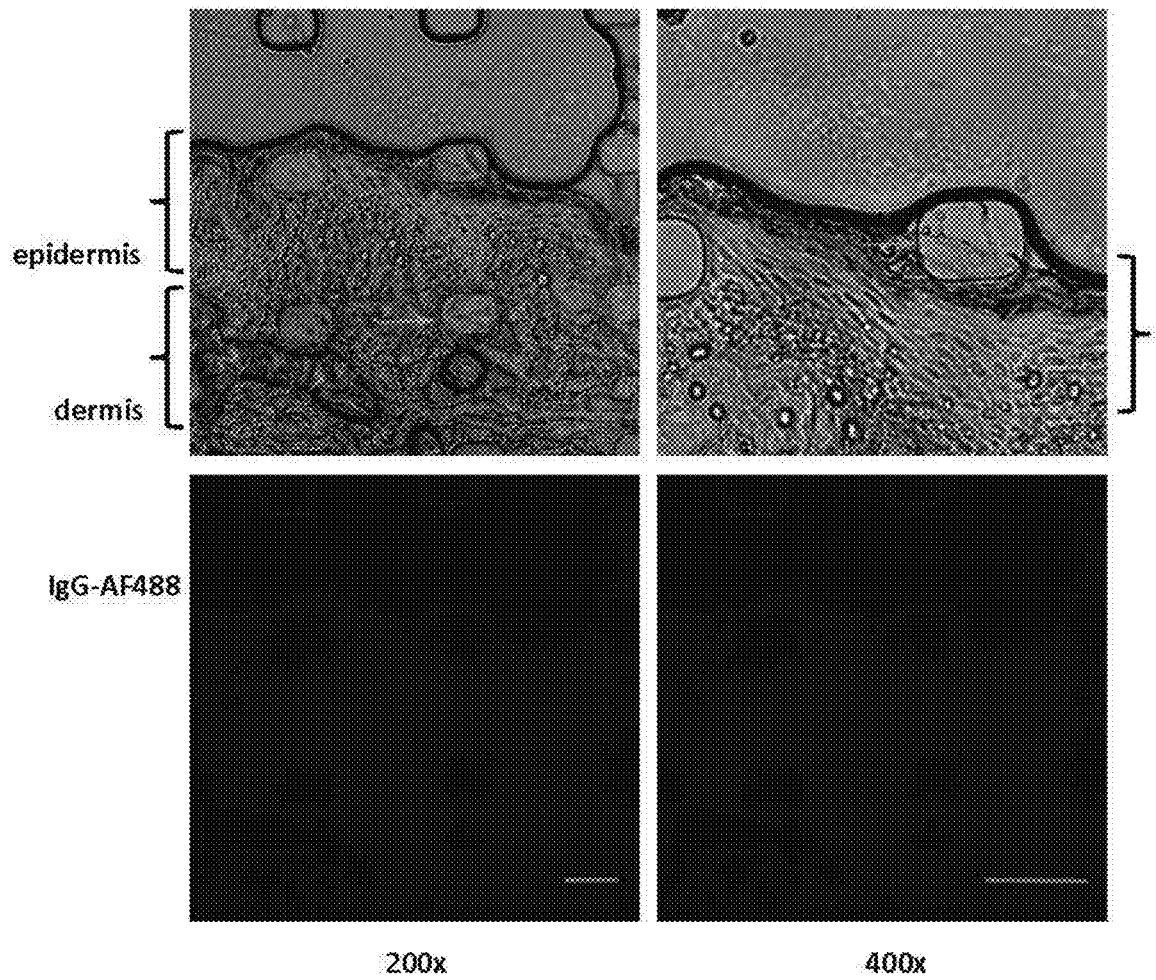
FIG. 36 shows a Control IgG-AF488 direct staining on fresh human skin sections. Drop 6 ul of premixed 0.2 µg IgG-AF488 (Thermo Fisher Scientific, cat no. Z25002) and PBS solution on fresh human skin cryosections, gently press 5 um pillar height X plate on tissue and incubate at room temperature for 1 min. Fluorescent signal was immediately taken under fluorescent microscope. Fluorescent signal was immediately taken under fluorescent microscope. Upper panel are bright filed images and lower panel are fluorescent images. Complete black images at lower panel indicate IgG-AF488 negative staining on skin tissues. Green arrow in each image points at the 5 um height pillar on X plate and red line is 40 um scale bar.

CK14-AF488 shows positive cytosolic and membrane staining of epidermal cells on fresh human skin section. CK14 is a member of the keratin family, the most diverse group of intermediate filaments. Together with two keratin 5 molecules, they form the cytoskeleton of epithelial cells. CK14 has been shown expression in epidermal progenitor cells, keratinocytes located at basal layer of epidermis in healthy adult skin (REF.). In FIG. 34, bright filed phase contrast images outlined clearer epidermis from dermis of human skin. In correspondent 200×fluorescent images, epidermal cells at basal layers show stronger positive fluorescence signals. Clear membrane and cytosolic staining of CK14 in epidermal cells was observed under 400×fluorescent microscope. Control IgG-AF488 shows negative staining on human skin section (FIG. 36). Therefore, CK14-AF488 staining using X plate show similar pattern Lamin A/C-AF488 shows positive nuclear staining of epidermal and dermal cells on fresh human skin section. Nuclear Lamins are intermediate filament proteins that form a network at the nucleoplasmic site of the nuclear membrane. In healthy adult skin, Lamin A/C is expressed in the suprabasal cell compartment of the epidermis, whereas the basal cells were mostly unstained (REF). In FIG. 35, 200× fluorescent image shows positive Lamin A/C staining in suprabasal epidermal cells, and nuclei staining is further evidenced in 400× image. We also observed some Lamin A/C positive cells in dermis of skin section.

Figure 37:
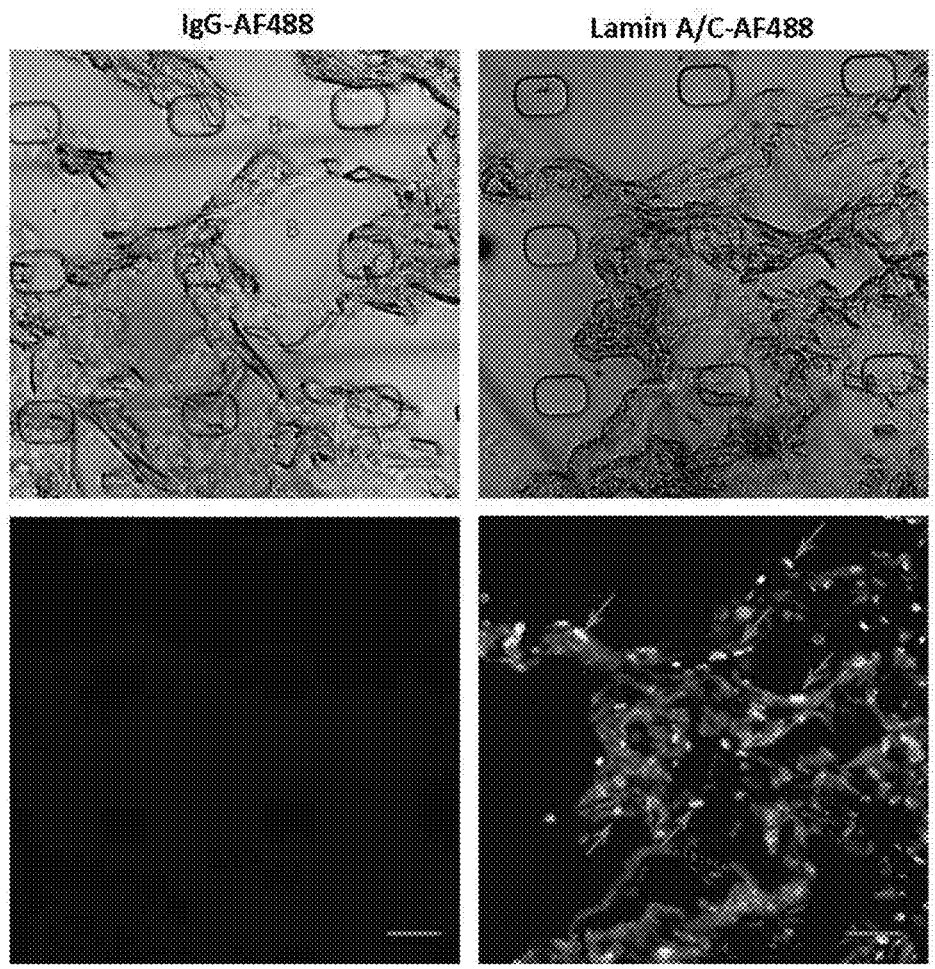
FIG. 37 shows a Lamin A/C-AF488 direct staining on fresh human lung sections. Drop 6 ul of premixed 0.2 µg IgG-AF488 (Thermo Fisher Scientific, cat no. Z25002) or Lamin A/C-AF488 (Cell Signaling, cat no. 8617S) and PBS solution on fresh human lung cryosections, gently press 5 um pillar height X plate on tissue and incubate at room temperature for 1 min. Fluorescent signal was immediately taken under fluorescent microscope. Upper panel are bright field images show lung bronchiole (B) and vascular (V) structures. Lower panel are correspondent fluorescent images. Red arrows indicate Lamin A/C positive cells in both bronchial epithelial cells and vascular endothelial cells. Control IgG-AF488 staining is negative. Green arrow in each image points at the 5 um height pillar on X plate and red line is 40 µm scale bar.

Lamin A/C-AF488 shows positive nuclear staining on fresh human lung section. Lamin A/C expression in human normal airway epithelial cells hasn't been thoroughly studied. We found that bronchial epithelial cells are positive to Lamin A/C-AF488 staining (FIG. 37). In addition, vascular endothelial cells are also shown positive staining on human fresh lung sections (FIG. 37).

Figure 38:
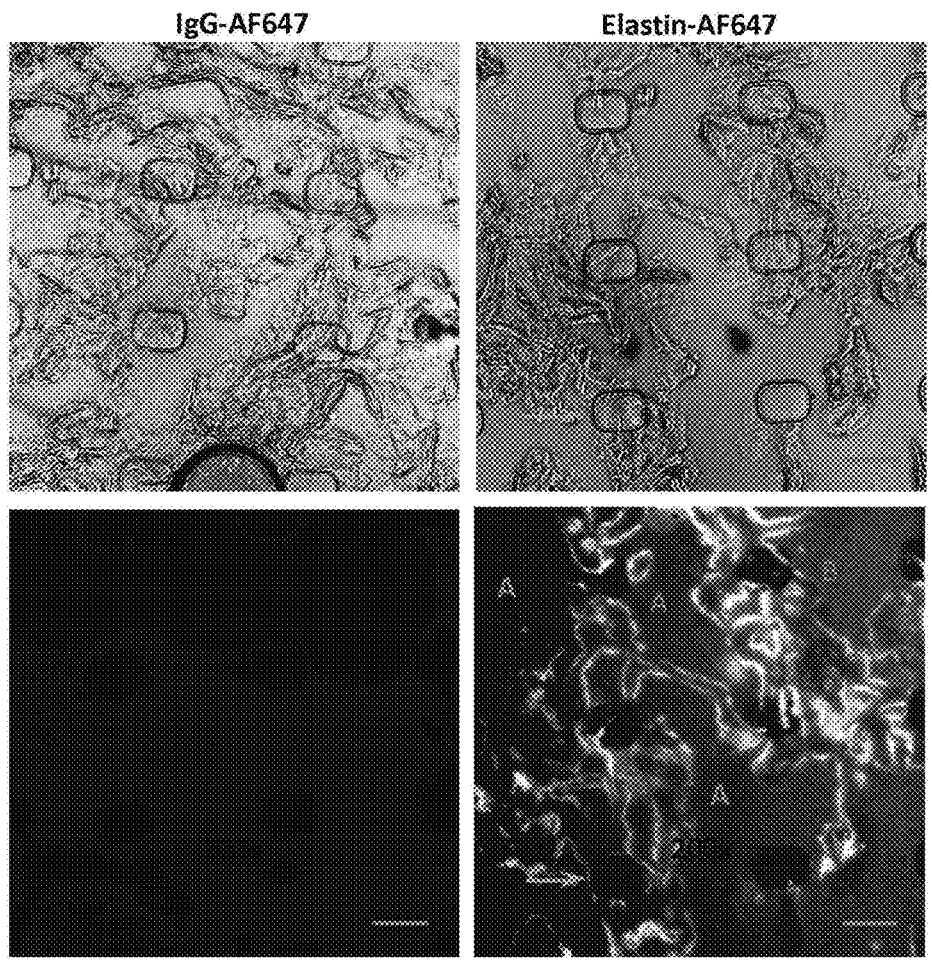
FIG. 38 shows a Elastin-AF647 direct staining on pre-fixed human lung sections. Human lung sections were prefixed in ice cold acetone for 5 minutes. Drop 6 ul of premixed 0.2 µg IgG-AF647 (Thermo Fisher Scientific, cat no. Z25008) or Elastin-AF647 (Santa Cruz, cat no. sc-58756 AF647) and PBS solution on tissue sections, gently press 5 um pillar height X plate on tissue and incubate at room temperature for 1 min. Fluorescent signal was immediately taken under fluorescent microscope. Upper panel are bright field images show lung bronchiole (B), alveolar (A) and vascular (V) structures. Lower panel correspondent fluorescent image shows Elastin-AF647 positive signals distributed through bronchiole and alveolar walls. Control IgG-AF488 staining is negative. Green arrow in each image points at the 5 um height pillar on X plate and red line is 40 um scale bar.

Elastin-AF647 shows positive staining on prefixed human lung sections. Elastin fibers consistently distribute in human pulmonary bronchiole and alveolar walls (REF). After prefix lung
section with acetone, using the micro volume embodiment system, Elastin-AF647 shows positive staining on lung bronchiole and alveolar walls, as well as vascular walls. (FIG. 38)

We have demonstrated the feasibility of using micro volume embodiment, comprising X plate, fresh or pre-fixed tissue sections and slide, for IHC/1F staining. This system advanced IHC/1F staining procedure from 2-4 hrs to 1min with high specificity and low background.

Examples of Observing the Specifically Stained Cell Using Optical Enhancers

AM1. A method of assaying cells using homogeneous assay, comprising:
 (a) obtaining a sample containing or suspected of containing a target cell;
 (b) obtaining detection agents that specifically bind the target cell, wherein each of the detection agent has an optical label capable of emitting light in a wavelength range;
 (c) obtaining optical enhancers, wherein each is capable of (i) emitting light in a wavelength range that overlaps with or within 30 nm near the wavelength range of the optical label and (ii) being attached to the target cell;
 (d) attaching the optical enhancers to the target cell;
 (e) binding specifically the target cell with the detection agents; and
 (f) placing the sample between two plates, wherein (1) the target cell in the sample specifically binds to the detection agent and is attached by the optical enhances, and (ii) at least a part of the sample is confined by the two plates into a thin layer of a thickness, wherein the thickness is configured so that for a given target cell concentration in the sample, each individual target cell does not substantially overlap other target cells when viewed inthe direction normal to the sample layer; and
 (g) imaging the target cell; wherein the optical enhancers enhance an imaging of the target cell in the sample layer.

AM2. A method for assaying a plurality of cells, comprising:
 (a) obtaining a sample suspected of having a plurality of cells;
 (b) attaching an optical enhancer to said plurality of cells, wherein said optical enhancer is capable of emitting light having a wavelength;
 (c) providing a detecting agent to bind to the optical enhancer, said detection agent comprises an optical label, wherein said emitting light of said optical enhancer has a wavelength that overlaps with the wavelength of said optical label of 30 nm;
 (d) placing the sample between a first plate and a second plate, wherein at least a part of the sample is confined by the first plate and the second plate into a thin layer, wherein the layer is configured such that, for a given concentration of said plurality of cells, each of said plurality of target cells do not substantially overlap when viewed in the direction normal to the sample layer; and
 (e) imaging the plurality of cells, wherein the optical enhancer enhances an imaging of the target cell in the sample layer.

AD1. A device for fast staining cells in a sample, comprising:
 a first plate, a second plate, and spacers, wherein:
 the first and the second plate are movable relative to each other into a different configuration, said different configuration includes an open configuration and a closed configuration;
 one or both of the first and second plates is flexible;
 the first plate has on its inner surface, a sample contact area for contacting a sample containing or suspected of containing a cell; and
 the second plate comprises the spacers fixed on its inner surface, at least one of the spacers is inside the sample contact area, the spacers have a predetermined substantially uniform height that is equal to 200 μm or less;
 wherein, in the open configuration, the two plates are partially or entirely separated, the spacing between the plates is not regulated by the spacers, and the sample is deposited on one or both of the plates;

wherein in the closed configuration, which is configured after deposition of the sample in the open configuration, at least part of the sample is compressed by the two plates into a layer of highly uniform thickness, wherein the uniform thickness of the layer is confined by the inner surfaces of the plates and is regulated by the plates and the spacers.

AD2. A device for a saying cells using homogeneous assay, comprising: a first plate, a second plate, and spacers, wherein: the first and second plates are movable relative to each other into different configurations, including an open configuration and a closed configuration; each of the plates has, on its respective inner surface, a sample contact area for contacting a sample containing or suspected of containing a target cell; and the first plate comprises the spacers that are fixed on its inner surface, atleast one of the spacers is inside the sample contact area, the spacers have a predetermined substantially uniform height that is equal to 200 μm or less;

wherein in the open configuration, the two plates are partially or entirely separated apart, the spacing between the plates is not regulated by the spacers, and the sample is deposited on one or both of the plates; and wherein in the closed configuration, which is configured after deposition of the sample in the open configuration: at least part of the sample is compressed by the two plates into a layer of highly uniform thickness, the uniform thickness of the layer is confined by the inner surfaces of the plates and is regulated by the plates and the spacers.

The method and device of any prior claim, wherein the optical signal from the optical enhancer is equal or less than the optical signal from the area of the sample layer that does not contain a target cell.

The method and device of any prior claim, wherein, before depositing the sample between the two plates, the detection agent and the optical enhancer are coated on the inner surface of the plates.

The method and device of any prior claim, wherein, before depositing the sample between the two plates, the detection agent and the optical enhancer are coated on the inner surface of the plates.

The method and device of any prior claim, wherein the layer thickness of the at least a part of the sample is configured so that the time for the detection agent and the optical enhancer is 30 secs or less.

The method and device of any prior claim, wherein the layer thickness of the at least a part of the sample is configured so that the time for the detection agent and the optical enhancer is 60 secs or less.

The method and device of any prior claim, wherein the layer thickness of the at least a part of the sample is configured so that the time for the detection agent and the optical enhancer is 120 secs or less.

The method and device of any prior claim, wherein the attachment of the optical enhancer to the target cell is specific.

The method and device of any prior claim, wherein the attachment of the optical enhancer to the target cell is nonspecific.

B. Immunostaining

In some embodiments, immunostaining can be used to detect a cell or non-cell analyte within a sample. In some embodiments, immunostaining can be used to detect a cell or non-cell analyte by enhancing signal from the cell or non-cell analyte relative to a background signal.

Immunostaining can generally refer to any method that uses one or more antibodies to detect a cell or non-cell analyte within a sample. A naturally occurring antibody can be a protein comprising at least two heavy (H) chains and two light (L) chains inter-connected by disulfide bonds. Each heavy chain can be comprised of a heavy chain variable region (VH) and a heavy chain constant region. The heavy chain constant region can be comprised of three domains, CH1, CH2 and CH3—Each light chain can be comprised of a light chain variable region (VL) and a light chain constant region. The light chain constant region can be comprised of one domain, CL. The VH and VL regions can be further subdivided into regions of hypervariability, termed complementary determining regions (CDR), interspersed with regions that are more conserved, termed framework regions (FR). Each VH and VL can be composed of three CDRs and four FRs arranged from amino-terminus to carboxy-terminus in the following order: FR1, CDR1, FR2, CDR2, FR3, COR3, and FR4. The constant regions of the antibodies can mediate the binding of the immunoglobulin to host tissues or factors, including various cells of the immune system (e.g., effector cells) and the first component (C1 q) of the classical complement system. The antibodies can be of any isotype (e.g., IgG, IgE, IgM, IgD, IgA and IgY), class (e.g., IgG1, IgG2, IgG3, IgG4, IgA1 and IgA2), subclass or modified version thereof.

Antibodies can include a complete immunoglobulins or fragments thereof. An antibody fragment can refer to one or more fragments of an antibody that retain the ability to specifically bind to a cell or non-cell analyte, such as an antigen. In addition, aggregates, polymers, and conjugates of immunoglobulins or their fragments can be used where appropriate so long as binding affinity for a particular molecule is maintained. Examples of antibody fragments include a Fab fragment, a monovalent fragment consisting of the VL, VH, CL and CH1 domains; a F(ab)2 fragment, a bivalent fragment comprising two Fab fragments linked by a disulfide bridge at the hinge region; an Fd fragment consisting of the VH and CH1 domains; an Fv fragment consisting of the VL and VH domains of a single arm of an antibody; a single domain antibody (dAb) fragment, which consists of a VH domain; and an isolated CDR and a single chain Fragment (scFv) in which the VL and VH regions pair to form monovalent molecules (known as single chain Fv (scFv)). Thus, antibody fragments include Fab, F(ab)2, scFv, Fv, dAb, and the like. Although the two domains VL and VH are coded for by separate genes, they can be joined, using recombinant methods, by an artificial peptide linker that enables them to be made as a single protein chain. Such single chain antibodies include one or more antigen binding moieties. These antibody fragments can be obtained using conventional techniques known to those of skill in the art, and the fragments can be screened for utility in the same manner as are intact antibodies. Antibodies can be human, humanized, chimeric, isolated, dog, cat, donkey, sheep, any plant, animal, or mammal.

Figure 2:
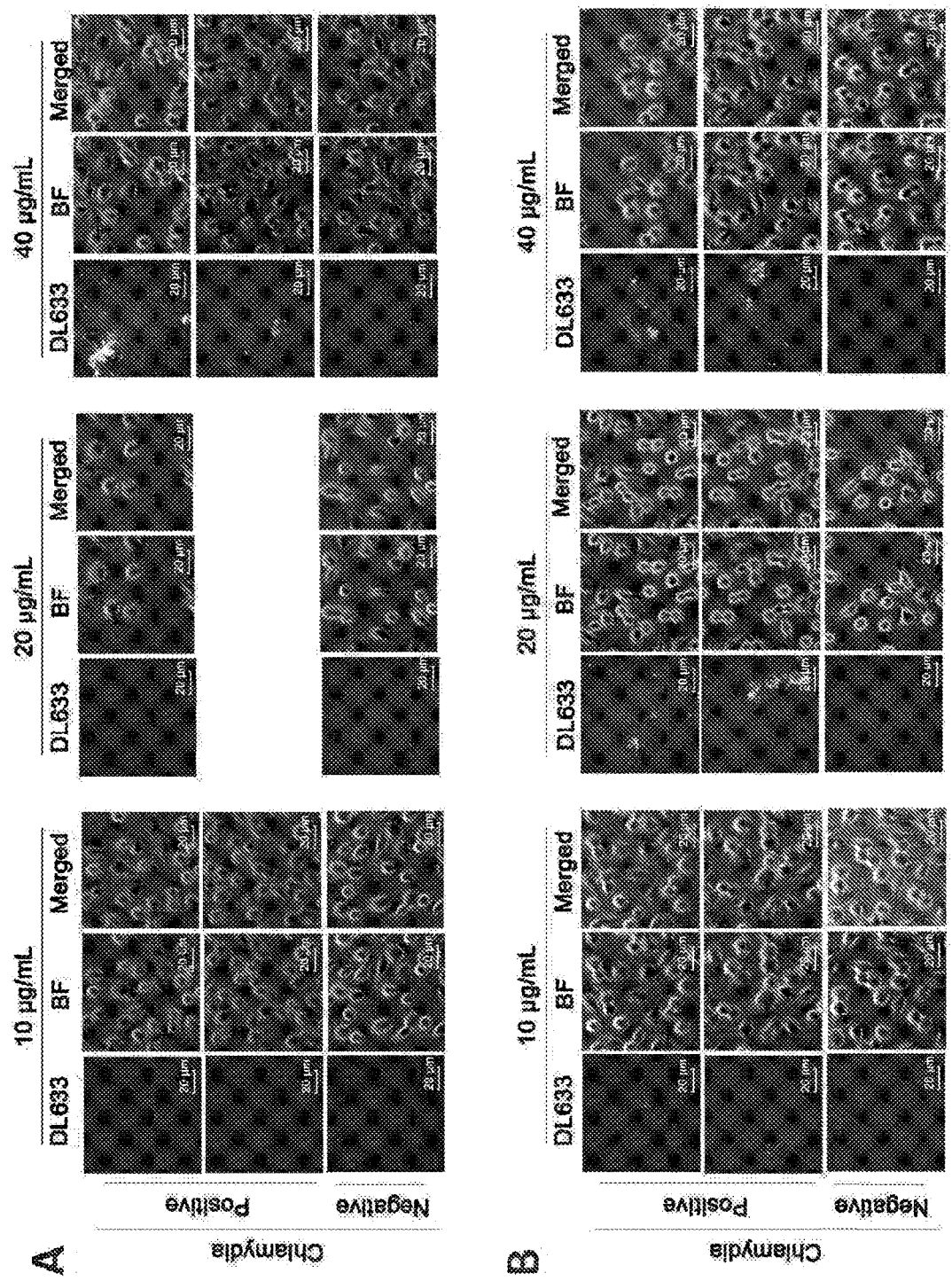
FIG. 2 shows exemplary pictures of chlamydia staining with the QMAX device. Panel (A) illustrates the results for the experiments using a 15 second incubation with the antibody to chlamydia; panel (B) illustrates the results for the experiments using a 30 second incubation with the antibody to chlamydia.
Figure 22:
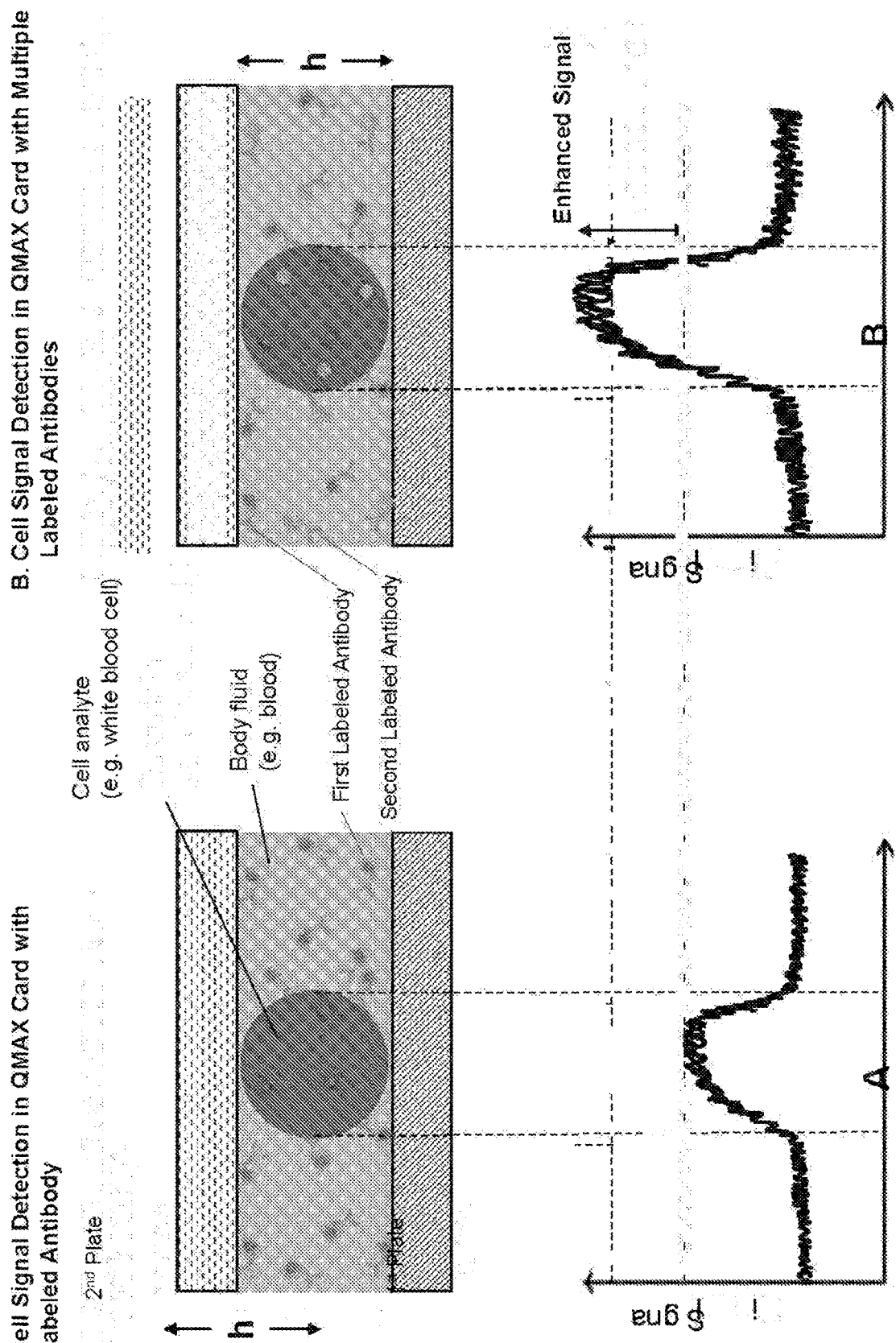
FIG. 22 shows an exemplary effect of using multiple labeled antibodies on signal detection from a cell or non-cell analyte within a sample.

In any of the embodiments of the present disclosure, any number and/or type of antibodies can be used. In particular, about 1 antibody, about 2 antibodies, about 3 antibodies, about 4 antibodies, about 5 antibodies, about 10 antibodies, about 25 antibodies, or greater than about 25 antibodies can be used. For example, as shown in FIG. 22A, a labeled antibody can be used to detect a cell analyte within a sample. However, as shown in FIG. 22B, 2 different labeled antibodies can be used to detect a cell or non-cell analyte (e.g., an antigen) within a sample, thereby enhancing a signal detected from the cell or non-cell analyte relative to a background signal. In some embodiments, two or more antibodies can be used to detect a cell or non-cell analyte, and the two or more antibodies can bind the same molecule.

In some embodiments, two or more antibodies can be used to detect a cell or non-cell analyte, and the two or more antibodies can bind the same epitope. In some embodiments, two or more antibodies can be used to detect a cell or non-cell analyte, and the two or more antibodies can bind different epitopes on the same antigen (e.g., polyclonal antibodies). In some embodiments, two or more antibodies can be used to detect a cell or non-cell analyte, and the two or more antibodies can bind the same epitope on different molecules. In some embodiments, two or more antibodies can be used to detect a cell or non-cell analyte, and the two or more antibodies can bind different molecules.

Any antibody used in an embodiment of the present disclosure can be labeled or unlabeled. A label can refer to a molecule that, when attached (directly or indirectly, e.g., via an antibody) to another molecule provides or enhances a means of detecting the other molecule. A signal emitted from a label can allow detection of the molecule or complex to which it is attached, and/or the label itself. A label can be a molecular species that elicits a physical or chemical response that can be observed or detected by the naked eye or by means of instrumentation such as, without limitation, cameras (e.g., mobile phone cameras), scintillation counters, colorimeters, UV spectrophotometers and the like. Labels include but are not limited to, radioactive isotopes, fluorophores, chemiluminescent dyes, chromophores, enzymes, enzymes substrates, enzyme cofactors, enzyme inhibitors, dyes, metal ions, nanoparticles, metal sols, ligands (such as biotin, avidin, streptavidin or haptens) and the like. A fluorescence or fluorescent label or tag emits detectable light at a particular wavelength when excited at a different wavelength. A radiolabel or radioactive tag emits radioactive particles detectable with an instrument such as, without limitation, a scintillation counter. Other signal generation detection methods include: chemiluminescence detection, electrochemiluminescence detection, Raman energy detection, colorimetric detection, hybridization protection assays, and mass spectrometry. Non limiting examples of labels include a fluorophore, a chromophore, FITC, TRITC, DTAF, 1H,5H,11H, 15H-Xantheno[2,3,4-ij:5,6,7-ij']diquinolizin-18-ium, 9-[2(or 4)-(chlorosulfonyl)-4(or 2)-sulfophenyl]-2,3,6,7,12,13,16,17-octahydro-, inner salt (TEXAS RED®), phycoerythrin, allophycocyanin, a green fluorescent protein (GFP), a blue fluorescent protein (BFP), rhodamine, FAM, TET, HEX, JOE, TAMRA, ROX, an aromatic-substituted xanthene dye, 4,7-dichloro-fluorescein, 4,7-dichloro-rhodamine, a cyanine dye, an enzyme, horseradish peroxidase (HRP), alkaline phosphatase, beta-galactosidase, luciferase, chloramphenicol acetyltransferase (CAT), avidin, streptavidin, biotin, a biotinylated protein, or any combination, fragments or derivatives thereof. In any embodiments, of the present disclosure, one or more labels can used to detect a cell or non-cell analyte. In any embodiments, of the present disclosure, two or more labels can used to detect a cell or non-cell analyte. In some embodiments, where two or more labels are used to detect a cell or non-cell analyte, the excitation and/or emission spectrum of the two or more labels can be the same. For example, a sample can be contacted with two antibodies (e.g., each of which bind to the same epitope on the same antigen), each having a different label that excites at the same wavelength. In another example, a sample can be contacted with two antibodies (e.g., each of which bind to a different epitope on the same antigen), each having the same label that excites at a predetermined wavelength. In some embodiments, where two or more labels are used to detect a cell or non-cell analyte, the excitation and/or emission spectrum of the two or more labels can be different. In some embodiments, where three or more labels are used to detect a cell or non-cell analyte, the excitation and/or emission spectrum of at least two or more labels can be the same. In some embodiments, where three or more labels are used to detect a cell or non-cell analyte, the excitation and/or emission spectrum of at least two or more labels can be different.

If an antibody comprises a label, the methods of detection can include fluorescence, luminescence, radioactivity, and the like. If the antibody is unlabeled, the detection of binding can be based on a change in some physical property of the target analyte. Such physical properties can include, for example, a refractive index or electrical impedance. The detection of binding of unlabeled antibody could include, for example, mass spectroscopy. In competitive methods, binding-site occupancy can be determined indirectly. In this method, the target cell or non-cell analyte can be exposed to a solution containing a cognate labeled antibody and an unlabeled antibody. The labeled cognate antibody and the unlabeled antibody compete for the binding sites on the target analyte. The affinity of the unlabeled antibody for the target analyte relative to the labeled cognate antibody is determined by the decrease in the amount of binding of the labeled antibody.

Dye Staining

In some embodiments, dye staining can be used to detect a cell or non-cell analyte within a sample. In some embodiments, dye staining can be used to detect a cell or non-cell analyte by enhancing signal from the cell or non-cell analyte relative to a background signal. Dye staining can refer to a technique used to enhance contrast in an image, and specifically enhance a detectable signal from a target cell or non-cell analyte in a sample. Stains and dyes can be used to highlight structures in biological tissues or cells for viewing. Stains can be used to define and examine cell populations (e.g., classifying different blood cells or bacteria, such as gram-positive and gram-negative bacteria), or organelles within individual cells. Dye staining can involve contacting a class-specific (e.g., DNA, protein, lipid, or carbohydrate) dye to a sample to qualify or quantify the presence of a specific cell or non-cell analyte within the sample.

In any of the embodiments of the present disclosure, any number and/or type of dyes can be used. In particular, about 1 dye, about 2 dyes, about 3 dyes, about 4 dyes, about 5 dyes, about 10 dyes, about 25 dyes, or greater than about 25 dyes can be used. In some embodiments, two or more dyes can be used to detect a cell or non-cell analyte, and the two or more dyes can bind the same molecule. In some embodiments, two or more dyes can be used to detect a cell or non-cell analyte, and the two or more dyes can stain the same region (e.g., the same organelle) of the same target cell or non-cell analyte. In some embodiments, two or more dyes can be used to detect a cell or non-cell analyte, and the two or more dyes can stain different regions (e.g., the cell cytoplasm and the cell nucleus) of the same target cell or non-cell analyte.

A signal emitted from a dye can allow detection of the molecule or complex to which it is attached. A dye can be a molecular species that elicits a physical or chemical response that can be observed or detected by the naked eye or by means of instrumentation such as, without limitation, cameras (e.g., mobile phone cameras), scintillation counters, colorimeters, UV spectrophotometers and the like. Dyes can include, but are not limited to 5-Ethynyl-2'-deoxyuridine, 7-Aminoactinomycin D, Acid fuchsin, Acridine orange, Acridine yellow, Alcian blue stain, Aniline Blue WS, Aniline Yellow, Auramine O, Bismarck brown Y, Brilliant green (dye), Bromodeoxyuridine, Calcofluor-white, Carbol fuchsin, Carboxyfluorescein diacetate succinimidyl ester, Carmine, Congo red, Coomassie Brilliant Blue, Crystal violet, DAPI, Oil, DiOC6, Eosin, Ethidium bromide, Ethyl Green, Fast Green FCF, Feulgen stain, Fluorescein, Fluorescein isothiocyanate, Fuchsine, GelGreen, GelRed, Giemsa stain, Green S, H&E stain, Haematoxylin, Hematein, Hoechst stain, Janus Green B, Jaswant Singh-Bhattacharji (JSB) stain, Light Green SF, Lugol's iodine, Malachite green, Mallory's trichrome stain, Methyl blue, Methyl violet, Methylene blue, Neutral red, New methylene blue, Nigrosin, Nile blue, Nile red, Oil Blue 35, Oil Red O, range G, Orcein, Osmium tetroxide, P-Dimethylaminocinnamaldehyde, Phyloxin, Ponceau 2R, Ponceau 6R, Propidium iodide, Pyranine, Quinoline Yellow SS, Red2G, Rhodamine, Rhodamine 123, Rhodamine 6G, Rhodamine B, RiboGreen, Ruthenium red, Safranin, Silver nitrate, Staining, Sudan Black B, Sudan III, Sudan IV, Sudan Red 7B, SYBR Green I, SYBR Safe, SYTOX, Template:Stains, TEXAS RED®, Toluidine blue stain, Trypan blue, User: Kyle MoJo/sandbox, Victoria blue BO, Water blue, Wayson stain, and Ziehl-Neelsen stain.

In some embodiments, the dye selected is a metachromatic dye. The term "metachromatic dye" can refer to a fluorescent dye that contains two or more peaks in its emission spectrum when bound to a cell or cellular components. A metachromatic dye can fluoresce at different wavelengths when bound to different types of cells or molecules, e.g., to RNA, DNA, or other cellular components. For example, a metachromatic dye used in any embodiment of the present disclosure fluoresces at different wavelengths when bound to double-stranded DNA, single-stranded DNA, or single-stranded RNA.

A variety of metachromatic dyes are known in the art and include, without limitation, xanthene dyes, carbocyanine dyes, polymethine dyes including Astra Violet FR, thiofalvine T, psuedoisocyanine, oxacarbocyanine dyes, acridine dyes, azine dyes, diphenylmethane dyes, methine dyes, oxazine dyes, cyanine dyes, styryl dyes, nonyl Acridine Orange dye (3,6-Bis-(dimethylamino)-10-nonylacridinium bromide, Molecular Probes, Eugene, Oreg.), the Acridine Red dye, the Toluidine Blue dye (2-amino-7-dimethylamino-3-methylphenothiazinium chloride), hydrosystilbamidine, and cyanine dyes including SYTO dyes, TOTO dyes, YOYO dyes, BOBO dyes, and combinations or derivatives thereof.

In some embodiments, the dye can be a non-metachromatic dye. The term "non-metachromatic dye" can refer to a fluorescent dye that provides a single wavelength of excitation when irradiated at a predetermined wavelength. Such dyes are useful in methods for discriminating multiple cell types or in circumstances in which a second fluorescent dye or antibody can be present that has a metachromatic wavelength that interferes with analysis be of the sample. Such dyes can be useful for staining cellular components of cells including acidophilic granules, basophilic granules, and cellular membranes of the cells. Non limiting examples of non-metachromatic dyes include, without limitation, Neutral Red dye (3-amino-7-dimethylamino-2-methylphenazine hydrochloride), Basic Orange 21 dye, DiOC dye (1,1'-dimethyloxacarbocyanine), Pyronin Y dye, Methylene Blue dye (3-bis-(dimethylamino)-phenothiazin-5-ium chloride), Auramine O dye (4,4'-(imidocarbonyl)-bis-(N,N,-dimethylaniline) monohydrochloride), LOS 751 dye (quinolinium, 6-(dimethylamino)-2-[4-[4-(dimethylamino)phenyl]-1,3-butadienyl]-2-ethyl perchlorate), Red series dyes, and combinations or derivatives thereof. Still other dyes suitable for use include ethidium bromide, propidium iodide (3,8-Diamino-5-(3-diethylaminopropyl)-6-phenyl-phenanthridinium iodide methiodide), hexidium iodide, dihydroethidium, ethidium monoazide, the Thiazole Orange dye, and combinations and derivatives thereof.

In some embodiments, the reagents coating on the device including an agent making cell membrane or cell nucleus permeable, including but not limit to 2-[4-(2,4,4-trimethylpentan-2-yl)phenoxy]ethanol (TRITON X-100™), surfactant, Zwittergent, ASB-14, ASB-16, 3-[(3-cholamidopropyl) dimethylammonio]-1-propanesulfonate (CHAPS), Cationic surfactant NN-[Tris(hydroxymethyl) methyl]-N-alkyl-N, N-dimethyl ammonium chloride (IIa), IIb, IIe, IId, cetyltrimethylammonium chloride (CTAC), polyoxyethylene sorbitan monolaurate (TWEEN® 20), polyoxyethylene sorbitan monopalmitate (TWEEN® 40), polyoxyethylene sorbitan monostearate (TWEEN® 60), polyoxyethylene sorbitan monooleate (TWEEN® 80), Sodium lauryl sulfate (SLS), ammonium lauryl sulfate, CTAB, sodium lauryl ether sulfate (SLES), sodium myreth sulfate, docusate, perfluorooctanesulfonate, alkyl-aryl ether phosphates, alkyl ether phosphates, cetyltrimethylammonium bromide (CTAB), cetylpyridinium chloride (CPC), benzalkonium chloride (BAC), benzethonium chloride (BZT), dimethyldioctadecylammonium chloride, dioctadecyldimethlyammonium bromide (DODAB), cocamidopropyl hydroxysultaine, cocamidopropyl betaine, narrow-range ethoxylate, octaethylene glycol monododecyl ether, pentaethylene glycol monododecyl ether, nonxynols, TRITON X-100™, polyethoxylated tallow amine, cocamide monoethanolamine, cocamide diethanolamine, poloxamers, glycerol monostearate, glycerol monolaurate, sorbitan monolaurate, sorbitan monostearate, sorbitan tristearate, decyl glucoside, lauryl glucoside, octyl glucoside, lauryldimethylamine oxide, dimethyl sulfoxide, phosphine oxide.

In some embodiments, the reagents coating on the device including an agent making cell membrane or cell nucleus permeable, by method of osmotic pressure difference between the cell membrane as dilution, or tuning salt concentration.

In some embodiments, the reagents coating on the device including an agent making protein cross link, including but not limit to formaldehyde, glutaraldehyde, osmium tetroxide, potassium dichromate and potassium permanganate.

Any dye used in the embodiments of the present disclosure can be a cell permeant dye or cell impermeant dye. The term "cell permeant" can refer a dye that readily penetrates a cell wall and stains the components of the same without requiring the additional presence of a permeabilizing agent. Typically, cell-permeant dyes are utilized to stain live cells or components of cells that have not been lysed. In some embodiments, cell permeant dyes are utilized to analyze samples containing whole blood. In some embodiments of the present disclosure, if a cell impermeant dye is used, a cell permeabilizing agent may be used to enhance permeability of the cell to the dye.

Figure 23:
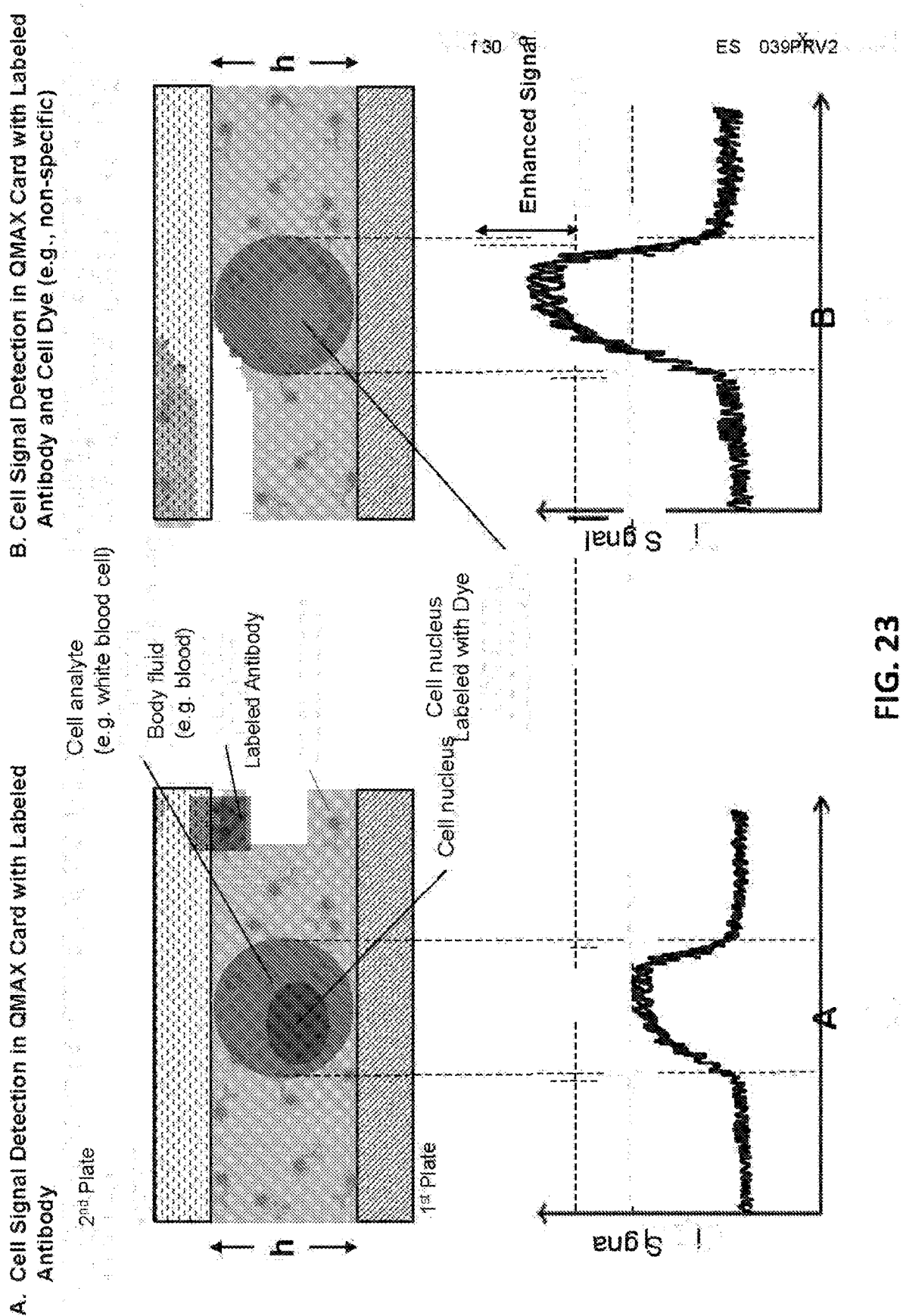
FIG. 23 shows an exemplary effect of using a combination of labeled antibodies and cell dye (e.g., non-specific) on signal detection from a cell or non-cell analyte within the FIG. 24 shows an exemplary effect of varying spacer height on signal detection from a cell or non-cell analyte within a sample.

In some embodiments, a dye can be used in combination with a labeled antibody. For example, as shown in FIG. 23A, a labeled antibody can be used to detect a cell analyte within a sample. However, as shown in FIG. 23B, a labeled antibody in combination with a cell dye can be used to detect a cell or non-cell analyte (e.g., an antigen) within a sample, thereby enhancing a signal detected from the cell or non-cell analyte relative to a background signal. Simple staining can refer to staining with only one stain/dye. There are various kinds of multiple staining, many of which are examples of counterstaining, differential staining, or both, including double staining and triple staining. In any embodiments, of the present disclosure, one or more dyes can used to detect a cell or non-cell analyte. In any embodiments, of the present disclosure, two or more dyes can used to detect a cell or non-cell analyte. In some embodiments, where two or more dyes are used to detect a cell or non-cell analyte, the excitation and/or emission spectrum of the two or more dyes can be the same. For example, a sample can be contacted with two antibodies (e.g., each of which bind to the same epitope on the same antigen), each having a different dye that excites at the same wavelength. In another example, a sample can be contacted with two antibodies (e.g., each of which bind to a different epitope on the same antigen), each having the same dye that excites at a predetermined wavelength. In some embodiments, where two or more dyes are used to detect a cell or non-cell analyte, the excitation and/or emission spectrum of the two or more dyes can be different. In some embodiments, where three or more dyes are used to detect a cell or non-cell analyte, the excitation and/or emission spectrum of at least two or more dyes can be the same. In some embodiments, where three or more dyes are used to detect a cell or non-cell analyte, the excitation and/or emission spectrum of at least two or more dyes can be different.

In any of the embodiments disclosed herein, a labeled antibody, stain, and/or dye can be coated onto one or more surfaces of the first plate and/or the second plate. It is contemplated that, coating a labeled antibody, stain, and/or dye onto one or more surfaces of the first plate or the second plate can be useful in reducing the number of steps performed by the user in order to analyze a sample. For example, if the first plate is coated with a cell staining reagent, the user would simply need to deposit a sample onto or into the QMAX card (e.g., within the sample contact area). Upon contact the cell staining reagent, cells within the sample can be automatically (e.g., without user intervention) stained. A reduction in the number steps performed by the user can reduce error (e.g., human error), increase accuracy in data analysis, and reduce the amount of time needed to analyze a sample. In some embodiments, stain or dye can be coated on one or more surfaces of a first plate, and a labeled antibody can be coated on one or more surfaces of a second plate. In another embodiment, a labeled antibody and a stain or dye can be coated on one or more surfaces of either the first plate or the second plate. In yet another embodiment, a labeled antibody and a stain or dye can be coated on one or more surfaces of both of the first plate and the second plate.

It is also contemplated that a blocking agent that competes with a stain or dye can be used to enhance signal from a target cell or non-cell analyte. For example, a blocking agent can be used to associate with unbound antibodies, thereby quenching the reporter molecule on the antibody and reducing the background signal that may otherwise be generated by said unbound antibodies. The blocking agent can block non-specific interaction of a dye with the cell or cellular components. The blocking agent can compete with other dyes present for the binding sites on the cells or non-cell analytes being analyzed. The blocking agent can compete with low affinity dyes for specific binding sites on the cells or non-cell analytes. The blocking agent can itself be a dye; in such circumstances, the dye is selected so that it is differentially detectable from the dye or stain that associates with a target cell or non-cell analyte. Alternatively, the blocking agent may be any compound which blocks non-specific interactions of the dye or stain without affecting the specific binding of the dye or stain to its target(s).

A blocking agent is either non-fluorescent, or is selected from among dyes that fluoresce at wavelengths different from the wavelength of the dye(s) used to detect a target cell or non-cell analyte. The blocking agent can be non-fluorescent at the wavelength that activates fluorescence of the dye or stain. A number of suitable blocking agents are known in the art and can be readily utilized in the embodiments of the present disclosure, including, without limitation, bisbenzamide (N,N'-(dithiodi-2,1-phenyl)-bisbenzamide), Hoechst33258 dye (bisbenzimide, 2'-(4-hydroxyphenyl)-5-(4-methyl-1-peperazinyl)-2,5-bi-1H-benzimidazole trihydrochloride pentahydrate), Hoechst 34580 dye, Hoechst 33342 dye (bisbenzimide, 2'-(ethoxyphenyl)-5-(4-methyl-1-peperazinyl)-2,5-bi-1H-benzimidazole trihydrochloride trihydrate), 4',6-diamidino-2-phenyl-indole dihydrochloride (DAPI), 4',6-bis-[2-imidazoxolinyl-4H, SH]-2-phenyl-indole (DIPI), Eosin Y dye, Orcein dye, Phloxine B dye (2',4',5',7'-tetrabromo-4,5,6,7-tetrachlorofluorescein disodium salt), Pentoxiphilline dye, Quinacrine dye (6-chloro-9-(4-diethyl-1-methylbutylamino)-2-methoxyacridine dihydrochloride), combinations thereof, and derivatives thereof.

RNA Fluorescence In Situ Hybridization

RNA fluorescence in situ hybridization (RNA-FISH) is a molecular cytogenetic technique to detect and localize specific RNFigA targets (mRNA, lncRNA and miRNA) in single cells via fluorescence microscopy. The traditional RNA-FISH methods usually include multiple steps, e.g., fixation, permeabilization, hybridization and imaging. Although FISH has wide medical applications, the complexity of the technique limits its potential in rapid diagnostics. Therefore, it is desirable to develop a fast, accurate, portable, and/or inexpensive RNA-FISH assay, which can be conducted by a non-professional.

In some embodiments, fluorescent in situ hybridization (FISH) can be used to detect a cell or non-cell analyte within a sample. In some embodiments, FISH can be used to detect a cell or non-cell analyte by enhancing signal from the cell or non-cell analyte relative to a background signal. FISH can generally refer to any method that uses one or more probes to detect a cell or non-cell analyte within a sample, including DNA probes to detect and localize the presence or absence of specific DNA sequences on chromosomes and RNA probes to detect or localize specific RNA targets (mRNA, lncRNA and miRNA). Thus, FISH is often used for finding specific features in DNA for use in genetic counseling, medicine, and species identification as well as define the spatial-temporal patterns of gene expression within cells and tissues. In some embodiments, probe can be short strands of DNA or RNA (often 10-25 nucleotides) which are complementary to a given target sequence are often used to locate a target. In some embodiments, Stellaris® RNA FISH probes can be used, which is an RNA visualization method that allows simultaneous detection, localization, and quantification of individual mRNA molecules.

In some embodiment, the surfactant used to permeabilize to allow probe accessibility including but not limit to Zwittergent, ASB-14, ASB-16, CHAPS, Cationic surfactant NN-[Tris(hydroxymethyl) methyl]-N-alkyl-N, N-dimethyl ammonium chloride (IIa), IIb, IIe, IId, CTAC, TWEEN® 20, TWEEN® 40, TWEEN® 60, TWEEN® 80, Sodium lauryl sulfate (SLS), ammonium lauryl sulfate, CTAB, sodium lauryl ether sulfate (SLES), sodium myreth sulfate, docusate, perfluorooctanesulfonate, alkyl-aryl ether phosphates, alkyl ether phosphates, CTAB, cetylpyridinium chloride (CPC), benzalkonium chloride (BAC), benzethonium chloride (BZT), dimethyldioctadecylammonium chloride, dioctadecyldimethlyammonium bromide (DODAB), cocamidopropyl hydroxysultaine, cocamidopropyl betaine, narrow-range ethoxylate, octaethyleneglycol monododecyl ether, pentaethylene glycol monododecyl ether, nonxynols, TRITON X-100™, polyethoxylated tallow amine, cocamide monoethanolamine, cocamide diethanolamine, poloxamers, glycerol monostearate, glycerol monolaurate, sorbitan monolaurate, sorbitan monostearate, sorbitan tristearate, decyl glucoside, lauryl glucoside, octyl glucoside, lauryldi-methylamine oxide, dimethyl sulfoxide, phosphine oxide.

In some embodiment, the reagent causing red blood cell lysis coated in the device including but not limit to Pluronic™ F-127, polyoxyl 35 castor oil (Cremophor EL), polyoxyethylene-polyoxypropylene block copolymer (Pluronic™ F-68), polyoxyethylene (40) stearate (Myrj 52), polyoxyethylene lauryl ether (Brij 35), sodium oleate, sodium dodecyl sulfate, TWEEN® 20, TWEEN® 40, TWEEN® 60, TWEEN® 80, SLS, CTAB, CTAC, Tamoxifen, saponin, hydrochloric acid, sulfuric acid, nitric acid, phosphoric acid, lactic acid, ABS-14, ABS-16, anti-malaria drugs (quinine compounds), arsenic, dapsone, metals (chromium/chromates, platinum salts, nickel compounds, copper, lead, cis-platinum), nitrites, nitrofurantoin, penicillin, phenazopyridine (pyridium), rho immune globulin, ribavirin, sulfonamides, sulfones.

Any RNA/DNA probe used in an embodiment of the present disclosure can be labeled. A label can refer to a molecule that, when attached (directly or indirectly) to another molecule provides or enhances a means of detecting the other molecule. A signal emitted from a label can allow detection of the molecule or complex to which it is attached, and/or the label itself. A label can be a molecular species that elicits a physical or chemical response that can be observed or detected by the naked eye or by means of instrumentation such as, without limitation, cameras (e.g., mobile phone cameras), scintillation counters, colorimeters, UV spectrophotometers and the like. Labels include but are not limited to, radioactive isotopes, fluorophores, chemiluminescent dyes, chromophores, enzymes, enzymes substrates, enzyme cofactors, enzyme inhibitors, dyes, metal ions, nanoparticles, metal sols, ligands (such as biotin, avidin, streptavidin or haptens) and the like. A fluorescence or fluorescent label or tag emits detectable light at a particular wavelength when excited at a different wavelength. A radiolabel or radioactive tag emits radioactive particles detectable with an instrument such as, without limitation, a scintillation counter. Other signal generation detection methods include: chemiluminescence detection, electrochemiluminescence detection, Raman energy detection, colorimetric detection, hybridization protection assays, and mass spectrometry. Non limiting examples of labels include a fluorophore, a chromophore, FITC, TRITC, DTAF, TEXAS RED®, phycoerythrin, allophycocyanin, a green fluorescent protein (GFP), a blue fluorescent protein (BFP), rhodamine, FAM, TET, HEX, JOE, TAMRA, ROX, an aromatic-substituted xanthene dye, 4,7-dichloro-fluorescein, 4,7-dichloro-rhodamine, a cyanine dye, an enzyme, horseradish peroxidase (HRP), alkaline phosphatase, beta-galactosidase, luciferase, chloramphenicol acetyltransferase (CAT), avidin, streptavidin, biotin, a biotinylated protein, or any combination, fragments or derivatives thereof. In any embodiments, of the present disclosure, one or more labels can used to detect a cell or non-cell analyte. In any embodiments, of the present disclosure, two or more labels can used to detect a cell or non-cell analyte. In some embodiments, where two or more labels are used to detect a cell or non-cell analyte, the excitation and/or emission spectrum of the two or more labels can be the same. For example, a sample can be contacted with two antibodies (e.g., each of which bind to the same epitope on the same antigen), each having a different label that excites at the same wavelength. In another example, a sample can be contacted with two antibodies (e.g., each of which bind to a different epitope on the same antigen), each having the same label that excites at a predetermined wavelength. In some embodiments, where two or more labels are used to detect a cell or non-cell analyte, the excitation and/or emission spectrum of the two or more labels can be different. In some embodiments, where three or more labels are used to detect a cell or non-cell analyte, the excitation and/or emission spectrum of at least two or more labels can be the same. In some embodiments, where three or more labels are used to detect a cell or non-cell analyte, the excitation and/or emission spectrum of at least two or more labels can be different.

Protocols

Figure 24:
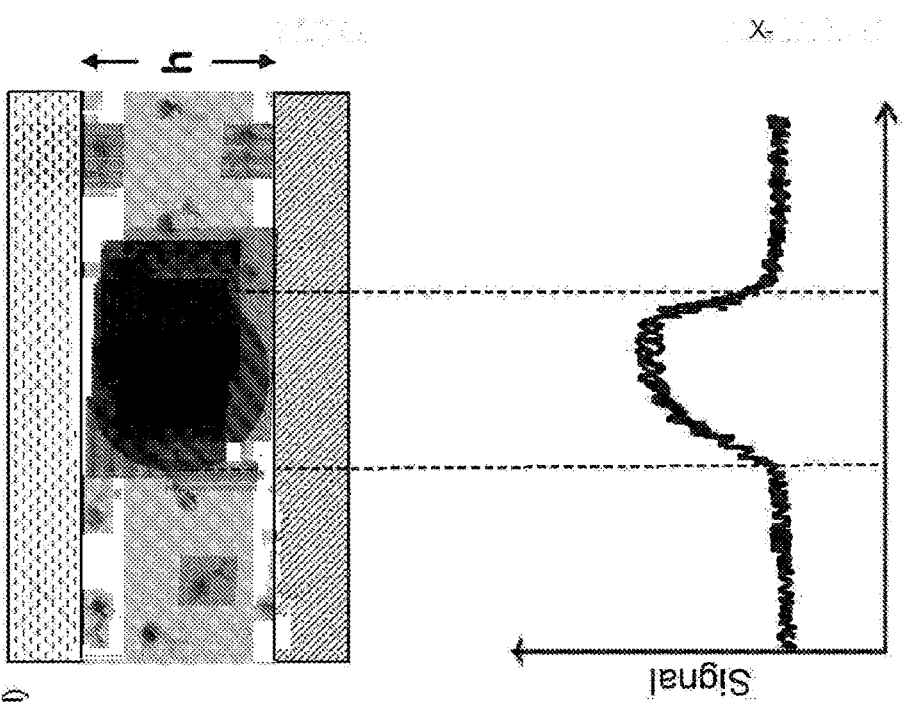
Figure 24:
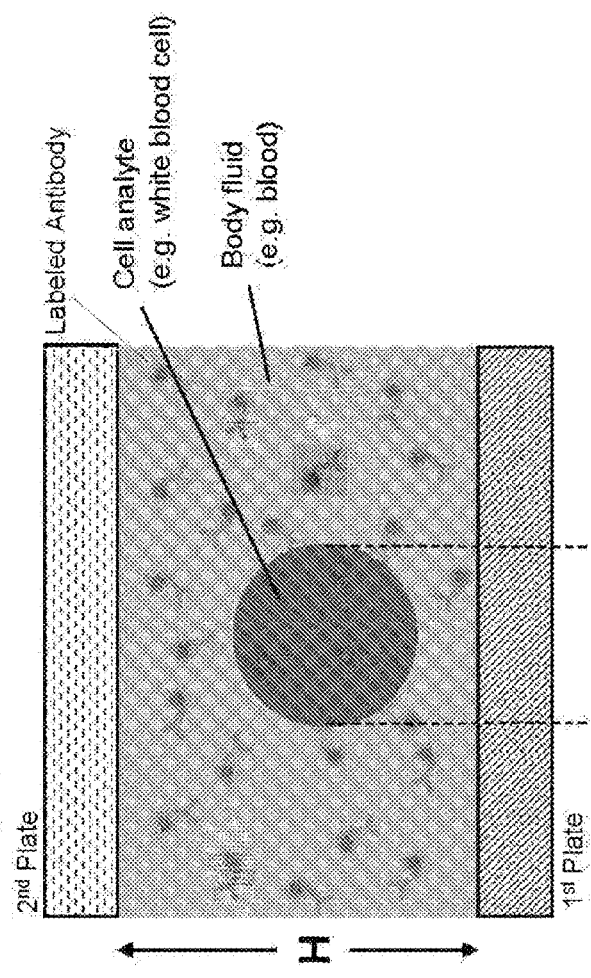

1. Design, synthesize and purify fluorescent probes for target RNA.
2. Use Biodot to print probe (1 nM) and surfactant (e.g. Zwittergent) on X-plate.
3. Apply one drop of blood on substrate plate, close chip, press, and incubate at room temperature for 1 minute.
4. Insert chip to the device, take pictures and analyze data Spacer Height & Sample Thickness In some embodiments of the present disclosure, the spacer height can be varied to adjust the thickness of the sample being analyzed, and thereby enhance detection of signal from a target cell or non-cell analyte. For example, as shown in FIG. 24, a signal detected from the cell or non-cell analyte relative to a background signal can be enhanced by varying the thickness of the sample from a larger thickness (FIG. 24A) to a smaller thickness (FIG. 24B). In some embodiments, the spacer height and/or thickness of the sample can be at most about 500 micrometers, at most about 250 micrometers, at most about 100 micrometers, at most about 90 micrometers, at most about 80 micrometers, at most about 70 micrometers, at most about 60 micrometers, at most about 50 micrometers, at most about 40 micrometers, at most about 30 micrometers, at most about 25 micrometers, at most about 20 micrometers, at most about 15 micrometers, at most about 10 micrometers, at most about 5 micrometers, at most about 4 micrometers, at most about 3 micrometers, at most about 2 micrometers, at most about 1 micrometers, at most about 0.5 micrometers, at most about 0.1 micrometers, or at most about 0.05 micrometers. For example, the spacer height can be at most about 30 micrometers. In some embodiments, the spacer height and/or thickness of the sample can be about 25 micrometers to 10 about 35 micrometers. In some embodiments, the spacer height and/or thickness of the sample can be about 20 micrometers to about 40 micrometers. In some embodiments, the spacer height and/or thickness of the sample can be about 10 micrometers to about 30 micrometers. In some embodiments, the spacer height and/or thickness of the sample can be about 30 micrometers to about 50 micrometers. In some embodiments, the spacer height and/or thickness of the sample can be about 50 micrometers to about 75 micrometers. In some embodiments, the spacer height and/or thickness of the sample can be about 1 micrometers to about 25 micrometers. For example, the spacer height and/or thickness of the sample can be about 25 microns to about 35 microns. In some embodiments, the spacer height and/or thickness of the sample can be determined based on a size or shape of a target cell or non-cell analyte. For example, lymphocytes can have an average diameter in suspension about 15 micrometers. Accordingly, in some embodiments, the spacer height and/or thickness of the sample can be about 15 micrometers, about 20 micrometers, about 25 micrometers, about 30 micrometers, or greater than about 30 micrometers.

Examples of the Present Invention

A1. A method for analyzing a sample, the method comprising:
(a) obtaining a device according to an embodiment as disclosed herein, the device comprising a first plate, a second plate, and spacers, wherein the spacers have a predetermined substantially uniform height that is equal to or less than about 200 microns;
(b) contacting the sample with two or more labeled antibodies to obtain a mixture, wherein said two or more labeled antibodies are capable of binding to one or more epitopes on a target cell within said sample;
(c) depositing the mixture on one or both of the plates when the plates are configured in an open configuration, wherein the open configuration is a configuration in which the two plates are partially or completely separated apart and the spacing between the plates is not regulated by the spacers; and
(d) after (b), forcing the two plates into a closed configuration, in which: at least part of the mixture is compressed by the two plates into a layer of substantially uniform thickness, wherein the uniform thickness of the layer is confined by the mixture contact surfaces of the plates and is regulated by the plates and the spacers.

A2. A method for analyzing a sample, the method comprising:
(a) obtaining a device according to an embodiment as disclosed herein, the device comprising a first plate, a second plate, and spacers, wherein the spacers have a predetermined substantially uniform height that is equal to or less than about 200 microns, and wherein at least one of said first plate, said second plate, and said spacers comprise at least one surface coated with two or more labeled antibodies;
(b) depositing the sample on one or both of the plates when the plates are configured in an open configuration, wherein the open configuration is a configuration in which the two plates are partially or completely separated apart and the spacing between the plates is not regulated by the spacers, wherein upon deposition of the sample on one or both plates, said sample is contacted with said two or more labeled antibodies, wherein said two or more labeled antibodies are capable of binding to one or more epitopes on a target cell within said sample;
(c) after (b), forcing the two plates into a closed configuration, in which: at least part of the sample is compressed by the two plates into a layer of substantially uniform thickness, wherein the uniform thickness of the layer is confined by the sample contact surfaces of the plates and is regulated by the plates and the spacers.

A3. The method of any prior embodiment, wherein the spacers have a predetermined substantially uniform height that is equal to or less than about 100 microns, equal to or less than about 75 microns, equal to or less than about 50 microns, equal to or less than about 30 microns, equal to or less than about 25 microns, equal to or less than about 10 microns, equal to or less than about 5 microns, or equal to or less than about 1 micron.

A4. The method of any prior embodiment, wherein said predetermined substantially uniform height of said spacers is determined based on a size or a shape of said target cell.

A5. The method of any prior embodiment, wherein said two or more labeled antibodies bind different epitopes on a molecule of said target cell.

A6. The method of any prior embodiment, wherein said two or more labeled antibodies bind the same epitope.

A7. The method of any prior embodiment, wherein said two or more labeled antibodies bind different molecules on said target cell.

A7.1 The method of any prior embodiment, wherein said labels coupled to said two or more labeled antibodies are capable of excitation at the same wavelength.

A8. A method for analyzing a sample, the method comprising:
(a) obtaining a device according to an embodiment as disclosed herein, the device comprising a first plate, a second plate, and spacers, wherein the spacers have a predetermined substantially uniform height that is equal to or less than about 200 microns, wherein said first plate comprises a surface coated with a first antibody and said second plate comprises a surface coated with a second antibody;
(b) depositing the sample on one or both of the plates when the plates are configured in an open configuration, wherein the open configuration is a configuration in which the two plates are partially or completely separated apart and the spacing between the plates is not regulated by the spacers, wherein upon deposition of the sample on one or both plates, said sample is contacted with said first antibody and said second antibody, wherein said first antibody and said second antibody are capable of binding to one or more epitopes on a target cell within said sample;
(c) after (b), forcing the two plates into a closed configuration, in which: at least part of the sample is compressed by the two plates into a layer of substantially uniform thickness, wherein the uniform thickness of the layer is confined by the sample contact surfaces of the plates and is regulated by the plates and the spacers.

A9. A method for analyzing a sample, the method comprising:
(a) obtaining a device according to an embodiment as disclosed herein, comprising: a first plate, a second plate, and spacers, wherein the spacers have a predetermined substantially uniform height that is equal to or less than about 200 microns;
(b) contacting the sample with two or more dyes to obtain a mixture, wherein said two or more labeled dyes are capable of binding to a target cell within said sample;
(c) depositing the mixture on one or both of the plates when the plates are configured in an open configuration, wherein the open configuration is a configuration in which the two plates are partially or completely separated apart and the spacing between the plates is not regulated by the spacers; and
(d) after (c), forcing the two plates into a closed configuration, in which: at least part of the mixture is compressed by the two plates into a layer of substantially uniform thickness, wherein the uniform thickness of the layer is confined by the mixture contact surfaces of the plates and is regulated by the plates and the spacers.

A10. A method for analyzing a sample, the method comprising:
(a) obtaining a device according to an embodiment as disclosed herein, the device comprising a first plate, a second plate, and spacers, wherein the spacers have a predetermined substantially uniform height that is equal to or less than about 200 microns, and wherein at least one of said first plate, said second plate, and said spacers comprise at least one surface coated with two or more dyes;

(b) depositing the sample on one or both of the plates when the plates are configured in an open configuration, wherein the open configuration is a configuration in which the two plates are partially or completely separated apart and the spacing between the plates is not regulated by the spacers, wherein upon deposition of the sample on one or both plates, said sample is contacted with said two or more dyes, wherein said two or more dyes are capable of binding to a target cell within said sample; and (c) after (b), forcing the two plates into a closed configuration, in which: at least part of the sample is compressed by the two plates into a layer of substantially uniform thickness, wherein the uniform thickness of the layer is confined by the sample contact surfaces of the plates and is regulated by the plates and the spacers.

A11. The method of any prior embodiment, wherein the spacers have a predetermined substantially uniform height that is equal to or less than about 100 microns, equal to or less than about 75 microns, equal to or less than about 50 microns, equal to or less than about 30 micron, equal to or less than about 25 microns, equal to or less than about 10 microns, equal to or less than about 5 microns, or equal to or less than about 1 micron.

A12. The method of any prior embodiment, wherein said predetermined substantially uniform height of said spacers is determined based on a size or a shape of said target cell.

A13. The method of any prior embodiment, wherein said two or more dyes non-specifically bind said target cell.

A14. The method of any prior embodiment, wherein said two or more dyes are capable of excitation at the same wavelength.

A15. A method for analyzing a sample, the method comprising:
  obtaining a device according to an embodiment as disclosed herein, the device comprising a first plate, a second plate, and spacers, wherein the spacers have a predetermined substantially uniform height that is equal to or less than about 200 microns, wherein said first plate comprises a surface coated with an antibody and said second plate comprises a surface coated with a dye;
  depositing the sample on one or both of the plates when the plates are configured in an open configuration, wherein the open configuration is a configuration in which the two plates are partially or completely separated apart and the spacing between the plates is not regulated by the spacers, wherein upon deposition of the sample on one or both plates, said sample is contacted with said antibody and said dye, wherein said antibody and said dye are capable of binding to a target cell;
  after depositing, forcing the two plates into a closed configuration, in which: at least part of the sample is compressed by the two plates into a layer of substantially uniform thickness, wherein the uniform thickness of the layer is confined by the sample contact surfaces of the plates and is regulated by the plates and the spacers.

A16. A method for analyzing a sample, the method comprising:
  obtaining a device according to an embodiment as disclosed herein, the device comprising a first plate, a second plate, and spacers, wherein the spacers have a predetermined substantially uniform height that is equal to or less than about 200 microns;
  contacting the sample with a labeled antibody and a dye to obtain a mixture, wherein said labeled antibody and said dye are capable of binding to a target cell within said sample;
  depositing the mixture on one or both of the plates when the plates are configured in an open configuration, wherein the open configuration is a configuration in which the two plates are partially or completely separated apart and the spacing between the plates is not regulated by the spacers;
  after depositing, forcing the two plates into a closed configuration, in which: at least part of the mixture is compressed by the two plates into a layer of substantially uniform thickness, wherein the uniform thickness of the layer is confined by the mixture contact surfaces of the plates and is regulated by the plates and the spacers.

A17. A method for analyzing a sample, the method comprising:
  obtaining a device according to an embodiment as disclosed herein, the device comprising a first plate, a second plate, and spacers, wherein the spacers have a predetermined uniform height that is equal to or less than about 200 microns, and wherein at least one of said first plate, said second plate, and said spacers comprise at least one surface coated with a labeled antibody and a dye;
  depositing the sample on one or both of the plates when the plates are configured in an open configuration, wherein the open configuration is a configuration in which the two plates are partially or completely separated apart and the spacing between the plates is not regulated by the spacers, wherein upon deposition of the sample on one or both plates, said sample is contacted with said labeled antibody and said dye, wherein said labeled antibody and said dye are capable of binding to a target cell within said sample; and
  after depositing, forcing the two plates into a closed configuration, in which: at least part of the sample is compressed by the two plates into a layer of substantially uniform thickness, wherein the uniform thickness of the layer is confined by the sample contact surfaces of the plates and is regulated by the plates and the spacers.

A18. The method of any prior embodiment, wherein the spacers have a predetermined substantially uniform height that is equal to or less than about 100 microns, equal to or less than about 75 microns, equal to or less than about 50 microns, equal to or less than about 30 microns, equal to or less than about 25 microns, equal to or less than about 10 microns, equal to or less than about 5 microns, or equal to or less than about 1 micron.

A19. The method of any prior embodiment, wherein said predetermined substantially uniform height of said spacers is determined based on a size or a shape of said target cell.

A20. The method of any prior embodiment, wherein said dye non-specifically binds to said target cell.

A21. The method of any prior embodiment, wherein said label on said labeled antibody and said dye are capable of excitation at the same wavelength.

In one embodiment, stain reagent and additives are coated on the same plate (1st or 2nd plate), or separate plate (1st and 2nd plate).

In one embodiment, additives are chemicals that have physical, or chemical or physiological impact on target cell. Examples are surfactant (refer to other Provisionals) and ions (refer to other Provisionals).

In one embodiment, stain reagent is labeled antibody, peptide, oligonucleotide, aptamer, small molecules and any other substances that have binding affinity to one or multiple specific components, inside or outside, of target cell.

In one embodiment, the detection of labeled stain reagent are fluorescence-based (refer to other Provisionals), chemiluminescence-based (refer to other Provisionals) or colorimetrics-based (refer to other Provisionals) or plasmonics-based (refer to other Provisionals).

In one embodiment, target cell are prokaryote such as bacteria and archaea, or eukaryote such as animal cell and plant cell. Common examples include mammalian cells, yeast and algae etc.

In one embodiment, the number of target cell in sample can be one or more than one.

In some embodiments, the reagents coating on the device including an agent making cell membrane or cell nucleus permeable, including but not limit to TRITON X-100™, surfactant, Zwittergent, ASB-14, ASB-16, CHAPS, Cationic surfactant NN-[Tris(hydroxymethyl) methyl]-N-alkyl-N, N-dimethyl ammonium chloride (IIa), IIb, IIe, IId, CTAC, TWEEN® 20, TWEEN® 40, TWEEN® 60, TWEEN® 80, Sodium lauryl sulfate (SLS), ammonium lauryl sulfate, CTAB, sodium lauryl ether sulfate (SLES), sodium myreth sulfate, docusate, perfluorooctanesulfonate, alkyl-aryl ether phosphates, alkyl ether phosphates, CTAB, cetylpyridinium chloride (CPC), benzalkonium chloride (BAC), benzethonium chloride (BZT), dimethyldioctadecylammonium chloride, dioctadecyldimethlyammonium bromide (DODAB), cocamidopropyl hydroxysultaine, cocamidopropyl betaine, narrow-range ethoxylate, octaethylene glycol monododecyl ether, pentaethylene glycol monododecyl ether, nonxynols, TRITON X-100™, polyethoxylated tallow amine, cocamide monoethanolamine, cocamide diethanolamine, poloxamers, glycerol monostearate, glycerol monolaurate, sorbitan monolaurate, sorbitan monostearate, sorbitan tristearate, decyl glucoside, lauryl glucoside, octyl glucoside, lauryldimethylamine oxide, dimethyl sulfoxide, phosphine oxide.

In some embodiments, the reagents coating on the device including an agent making cell membrane or cell nucleus permeable, by method of osmotic pressure difference between the cell membrane as dilution, or tuning salt concentration.

In some embodiments, the reagents coating on the device including an agent making protein cross link, including but not limit to formaldehyde, glutaraldehyde, osmium tetroxide, potassium dichromate and potassium permanganate.

The device, kit, system, or method of any prior embodiments, wherein the dye to stain the WBC is coated onto the first plate, or the second plate or both.

The device, kit, system, or method of any prior embodiments, wherein the dye to stain the WBC and PLT is coated onto the first plate, or the second plate or both.

The device, kit, system, or method of any prior embodiments, wherein the dye to stain the PLT is coated onto the first plate, or the second plate or both.

The device, kit, system, or method of any prior embodiments, wherein the reagents is coated by droplet printing into an array.

The device, kit, system, or method of any prior embodiments, wherein the reagents is coated by spray.

The device, kit, system, or method of any prior embodiments, wherein the reagents is coated by contact printing.

The device, kit, system, or method of any prior embodiments, wherein the reagents is coated by transfer printing.

The device, kit, system, or method of any prior embodiments, wherein the dye to stain the RBC is coated onto the first plate, or the second plate or both.

The device, kit, system, or method of any prior embodiments, wherein the surfactant to separate and round RBC is coated onto the first plate, or the second plate or both.

The device, kit, system, or method of any prior embodiments, wherein the chemical to lyse RBC is coated onto the first plate, or the second plate or both.

The device, kit, system, or method of any prior embodiments, wherein the acridine orange is coated onto the first plate, or the second plate or both.

The device, kit, system, or method of any prior embodiments, wherein the Zwittergent is coated onto the first plate, or the second plate or both.

The device, kit, system, or method of any prior embodiments, wherein the Methylene blue and Zwittergent is coated onto the first plate, or the second plate or both.

The device, kit, system, or method of any prior embodiments, wherein the acridine orange and Zwittergent is coated onto the first plate, or the second plate or both.

The device, kit, system, or method of any prior embodiments, wherein the $[1^2(2)\ Z,\ 16(17^2)\ Z]$-$1^3$,7,7,11,11,$17^3$-Hexamethyl-$1^3$H, $17^3$H-7,11-diaza-$3^1\lambda^5$, $15^1\lambda^5$-3(4,1), 15(1,4)-diquinolina-1, 17(2)-bis([1,3]benzoxazola)heptadecaphane-12(2), $16(17^2)$-diene-7,11-diium-$3^1$, $15^1$-bis (ylium) tetraiodide (YOYO dye) and Zwittergent is coated onto the first plate, or the second plate or both.

The devices or methods of any prior embodiment, wherein the device further comprises, on one or both plates, multi reagent layers including anti-conglutination, cell lysing, cell staining, release time control material layers, and their combinations; wherein each layer coated on the plates has a thickness of 10 nm, 100 nm, 200 nm, 500 nm, 1 um or a range between any two of the values.

The devices or methods of any prior embodiment, where anti-conglutination agent comprises ethylenediaminetetraacetic acid (EDTA), EDTA disodium, dipotassium ethylenediaminetetraacetic acid (K2EDTA), tripotassium ethylenediaminetetraacetic acid (K3EDTA), and etc.

The devices or methods of any prior embodiment, wherein cell stain agent comprise Wright's stain (Eosin, methylene blue), Giemsa stain (Eosin, methylene blue, and Azure B), May-Grunwald stain, Leishman's stain ("Polychromed" methylene blue (i.e. demethylated into various azures) and eosin), Erythrosine B stain (Erythrosin B), and other fluorescence stain including but not limit to Acridine orange dye, 3,3-dihexyloxacarbocyanine (DiOC6), Propidium Iodide (PI), Fluorescein Isothiocyanate (FITC) and Basic Orange 21 (BO21) dye, Ethidium Bromide, Brilliant Sulfaflavine and a Stilbene Disulfonic Acid derivative, Erythrosine B or trypan blue, Hoechst 33342, Trihydrochloride, Trihydrate, and DAPI (4',6-Diamidino-2-Phenylindole, Dihydrochloride), YOYO, acid fuchsine, hematoxylin, Hoechst stains including Hoechst 33258 and Hoechst 33342, methyl green, methylene blue, Nile blue, Nile red, osmium tetraoxide, rhodamine, safranine, MeOSuc-AAPV-AMC, CFSE, BCECF/AM, silver nitrate, neutral red, pyronin Y, Calcein-AM, Dihydroethidium, Xylene Cyanol FF, Rhodamine 123, 4-Methylumbelliferyl palmitate, Fast Blue B Salt, Lucifer Yellow CH dipotassium salt, DAPI dilactate, Propidium Iodide;

wherein the cell lysing agent comprises ammonium chloride, sodium bicarbonate, ethylenediaminetetraacetic acid (EDTA), acetic acid, citric acid, other acid and base, and like agents, and wherein release time control material comprises albumin, carbomers, carboxymethyl cellulose, carrageenan, chitosan, dextrin, polyethylene glycol, polyvinylpyrrolidone, polyvinyl alcohol, and etc.

In some embodiment, chemicals with certain concentration is coated on the plate and dissolved into the blood to achieve a uniform distribution of red blood cell in device.

In some embodiment, chemicals with certain concentration is coated on the plate and dissolved into the blood to lyse the red blood cell in device, wherein the coating can be on first plate, or second plate, or both.

In some embodiment, the chemicals coated in the device including but not limit to Surfactant, Zwittergent, ASB-14, ASB-16, CHAPS, Cationic surfactant NN-[Tris(hydroxymethyl) methyl]-N-alkyl-N, N-dimethyl ammonium chloride (IIa), IIb, IIe, IId, CTAC, TWEEN® 20, TWEEN® 40, TWEEN® 60, TWEEN® 80, Sodium lauryl sulfate (SLS), ammonium lauryl sulfate, CTAB, sodium lauryl ether sulfate (SLES), sodium myreth sulfate, docusate, perfluorooctanesulfonate, alkyl-aryl ether phosphates, alkyl ether phosphates, CTAB, cetylpyridinium chloride (CPC), benzalkonium chloride (BAC), benzethonium chloride (BZT), dimethyldioctadecylammonium chloride, dioctadecyldimethlyammonium bromide (DODAB), cocamidopropyl hydroxysultaine, cocamidopropyl betaine, narrow-range ethoxylate, octaethylene glycol monododecyl ether, pentaethylene glycol monododecyl ether, nonxynols, TRITON X-100™, polyethoxylated tallow amine, cocamide monoethanolamine, cocamide diethanolamine, poloxamers, glycerol monostearate, glycerol monolaurate, sorbitan monolaurate, sorbitan monostearate, sorbitan tristearate, decyl glucoside, lauryl glucoside, octyl glucoside, lauryldimethylamine oxide, dimethyl sulfoxide, phosphine oxide.

In some embodiment, the reagent causing red blood cell lysis coated in the device including but not limit to Pluronic™ F-127, Cremophor EL, Pluronic™ F-68, Myrj 52, Brij 35, sodium oleate, sodium dodecyl sulfate, TWEEN® 20, TWEEN® 40, TWEEN® 60, TWEEN® 80, SLS, CTAB, CTAC, Tamoxifen, saponin, hydrochloric acid, sulfuric acid, nitric acid, phosphoric acid, lactic acid, ABS-14, ABS-16, anti-malaria drugs (quinine compounds), arsenic, dapsone, metals (chromium/chromates, platinum salts, nickel compounds, copper, lead, cis-platinum), nitrites, nitrofurantoin, penicillin, phenazopyridine (pyridium), rho immune globulin, ribavirin, sulfonamides, sulfones.

In some embodiment, the anticoagulant coated in the device including but not limit to EDTA such as dipotassium ethylenediaminetetraacetic acid (K2EDTA), tripotassium ethylenediaminetetraacetic (K3EDTA), coumarins (vitamin K antagonists), warfarin (coumadin), acenocoumarol, phenprocoumon, atromentin, phenindione, heparin, fondaparinux and idraparinux, dabigatran, rivaroxaban, apixaban, edoxaban, betrixaban, NOACs, hirudin, lepirudin, bivalirudin, agratroban, dabigatran, batroxobin, hementin, Vitamin E, sodium citrate, acid citrate dextrose, oxalate such as fluoride oxalate, deltaparin, desirudin, enoxaparin.

In some embodiment, to achieve a uniform distribution of red blood cell in device, Zwittergent is coated on the plate with a preferred area concentration of 3 ng/mm$^2$, 5 ng/mm$^2$, 8 ng/mm$^2$, 12 ng/mm$^2$, ng/mm$^2$, 25 ng/mm$^2$, 35 ng/mm$^2$, 50 ng/mm$^2$, 80 ng/mm$^2$, 100 ng/mm$^2$ or in a range between any of the two values.

In some embodiment, to lyse red blood cell in device, Zwittergent is coated on the plate with a preferred area concentration of 100 ng/mm$^2$, 120 ng/mm$^2$, 150 ng/mm$^2$, 180 ng/mm$^2$, 20 ng/mm$^2$, 300 ng/mm$^2$, 400 ng/mm$^2$, 500 ng/mm$^2$, 800 ng/mm$^2$, 1000 ng/mm$^2$ or in a range between any of the two values.

In some embodiment, to achieve a uniform distribution of red blood cell in device, Zwittergent is coated on the plate with a preferred final concentration in blood of 0.05 mg/ml, 0.1 mg/ml, 0.2 mg/ml, 0.3 mg/ml, 0.5 mg/ml, 0.6 mg/ml, 1.0 mg/ml, 2 mg/ml or in a range between any of the two values.

In some embodiment, to lyse red blood cell in device, Zwittergent is coated on the plate with a preferred final concentration in blood of 2 mg/ml, 3 mg/ml, 4 mg/ml, 5 mg/ml, 6 mg/ml, 7 mg/ml, 9 mg/ml, 10 mg/ml, 15 mg/ml, 25 mg/ml, 50 mg/ml, or in a range between any of the two values.

In some embodiment, to achieve a uniform distribution of red blood cell in device, Zwittergent is coated on the plate with a preferred area concentration of 3 ng/mm$^2$. 5 ng/mm$^2$, 8 ng/mm$^2$, 12 ng/mm$^2$, 15 ng/mm$^2$, 25 ng/mm$^2$, 35 ng/mm$^2$, 50 ng/mm$^2$, 80 ng/mm$^2$. 100 ng/mm$^2$ or in a range between any of the two values.

In some embodiment, to lyse red blood cell in device, Zwittergent is coated on the plate with a preferred area concentration of 100 ng/mm$^2$, 120 ng/mm$^2$. 150 ng/mm$^2$, 180 ng/mm$^2$, 200 ng/mm$^2$. 300 ng/mm$^2$. 400 ng/mm$^2$. 500 ng/mm$^2$, 800 ng/mm$^2$, 1000 ng/mm$^2$ or in a range between any of the two values.

In some embodiment, to achieve a uniform distribution of red blood cell in device, Zwittergent is coated on the plate with a preferred final concentration in blood of 0.05 mg/ml, 0.1 mg/ml, 0.2 mg/ml, 0.3 mg/ml, 0.5 mg/ml, 0.6 mg/ml, 1.0 mg/ml, 2 mg/ml or in a range between any of the two values.

In some embodiment, to lyse red blood cell in device, Zwittergent is coated on the plate with a preferred final concentration in blood of 2 mg/ml, 3 mg/ml, 4 mg/ml, 5 mg/ml, 6 mg/ml, 7 mg/ml, 9 mg/ml, 10 mg/ml, 15 mg/ml, 25 mg/ml, 50 mg/ml, or in a range between any of the two values.

The device, kit, system, or method of any prior embodiments, wherein the acridine orange is coated on the plate with an area concentration of 0.5 ng/mm$^2$. 1 ng/mm$^2$, 2 ng/mm$^2$. 3 ng/mm$^2$. 5 ng/mm$^2$. 8 ng/mm$^2$. 10 ng/mm$^2$. 15 ng/mm$^2$. 20 ng/mm$^2$, 30 ng/mm$^2$ or in a range between any of the two values.

The device, kit, system, or method of any prior embodiments, wherein the acridine orange is coated on the plate with an area concentration of 3 to 10 ng/mm$^2$ and Zwittergent is coated on the plate with an area concentration of 3 to 10 ng/mm$^2$.

The device, kit, system, or method of any prior embodiments, wherein the acridine orange is coated on the plate with an area concentration of 5 to 20 ng/mm$^2$ and Zwittergent is coated on the plate with an area concentration of 10 to 30 ng/mm$^2$.

In some embodiment, label (example as immunoassay antibody label, RNA label, staining dye) is coated on the plate with a preferred final concentration in sample of 0.1 nM/ml, 0.5 nM/ml, 1 nM/ml, 5 nM/ml, 10 nM/ml, 15 nM/ml, 20 nM/ml, 50 nM/ml, or in a range between any of the two values.

In some embodiment, label (example as immunoassay antibody label, RNA label, staining dye) is coated on the plate with a preferred final concentration in sample of 1 nM/ml, 5 nM/ml, 10 nM/ml, 15 nM/ml, 20 nM/ml, or in a range between any of the two values.

In some embodiment, label (example as immunoassay antibody label, RNA label, staining dye) is coated on the plate with a preferred final concentration in sample of 0.1 uM/ml, 0.5 uM/ml, 1 uM/ml, 5 uM/ml, 10 uM/ml, 15 uM/ml, 20 uM/ml, 50 uM/ml, or in a range between any of the two values.

In some embodiment, label (example as immunoassay antibody label, RNA label, staining dye) is coated on the plate with a preferred final concentration in sample of 0.1 ng/ml, 0.5 ng/ml, 1.0 ng/ml, 1.5 ng/ml, 2.0 ng/ml, 5 ng/ml, 10 ng/ml, 50 ng/ml, or in a range between any of the two values.

In some embodiment, label (example as immunoassay antibody label, RNA label, staining dye) is coated on the plate with a preferred final concentration in sample of 0.05 mg/ml, 0.15 mg/ml, 0.3 mg/ml, 0.5 mg/ml, 1.0 mg/ml, or in a range between any of the two values.

In some embodiment, label (example as immunoassay antibody label, RNA label, staining dye) is coated on the plate with a preferred final concentration in sample of 0.1 mg/ml, 0.5 mg/ml, 1.0 mg/ml, 1.5 mg/ml, 2.0 mg/ml, 5 mg/ml, 10 mg/ml, 50 mg/ml, or in a range between any of the two values.

In some embodiment, label (example as immunoassay antibody label, RNA label, staining dye) is coated on the plate with a preferred final concentration in sample of 100 mg/ml, 200 mg/ml, 300 mg/ml, or in a range between any of the two values.

Example 1

Rapid Assay for Distinguishing Gram-Negative and Gram-Positive Bacteria

Materials

1. Hexidium Iodide: This nucleic acid stain is permeant to mammalian cells and selectively stains most gram-positive bacteria orange (Thermofisher, H7593).
2. SYTO 9: Stains both gram-positive and gram-negative bacteria green (Thermofisher, S34854).
3. 500 nm wavelength excitation filter.
4. *Staphylococcus epidermidis* (gram-positive), *Escherichia coli* (gram-negative).

Methods

Bacterial Culture Preparation:
1 *S. epidermidis* and *E. coli* were used as gram-positive and gram-negative bacteria, respectively. These distinct bacterial species were cultured in nutrient broth (R061582, Remel) at 37° C. overnight before staining.

Figure 25:
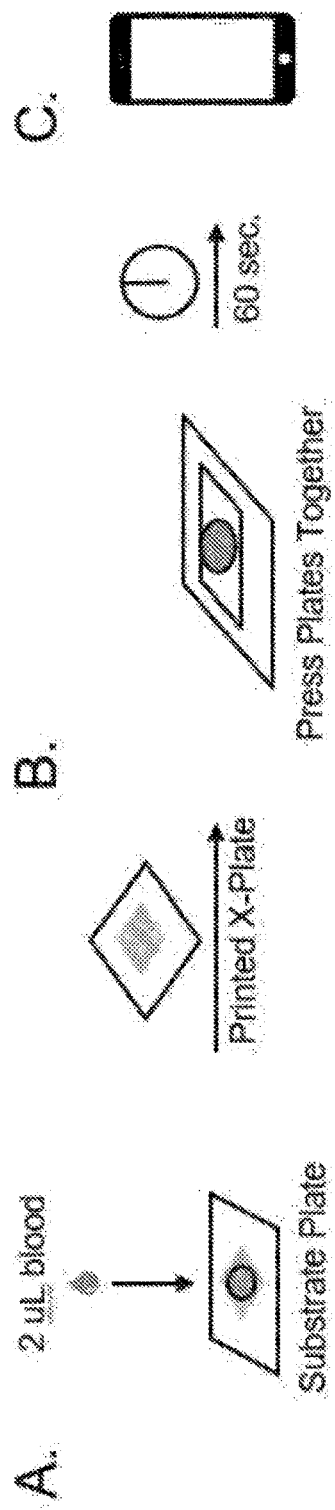
FIG. 25 shows assembly of the Q-card for distinguishing bacterial cell wall type. 2 ul of blood sample containing a mixture of S. epidermidis and E. coli was added to the substrate plate. The X-plate printed with the DNA dyes was placed on top of the blood sample and pressed firmly to promote mixing of the sample and dyes. Imaging was carried out using the iPhone 6s camera.

Q-Card Preparation:
1. A mixture containing 12 µg/ml of hexidium iodide and 8 uM SYTO 9 suspended in PBS were printed on a batch of X-plates (containing 2 um pillars) at 3 ul per cm$^2$ and air-dried.
2. 2 ul of PBS or blood that contains *S. epidermidis* and *E. coli* was added to a substrate plate. The printed X-plate and the substrate plate containing the bacterial-blood sample were pressed together firmly (FIG. 25).

Figure 26:
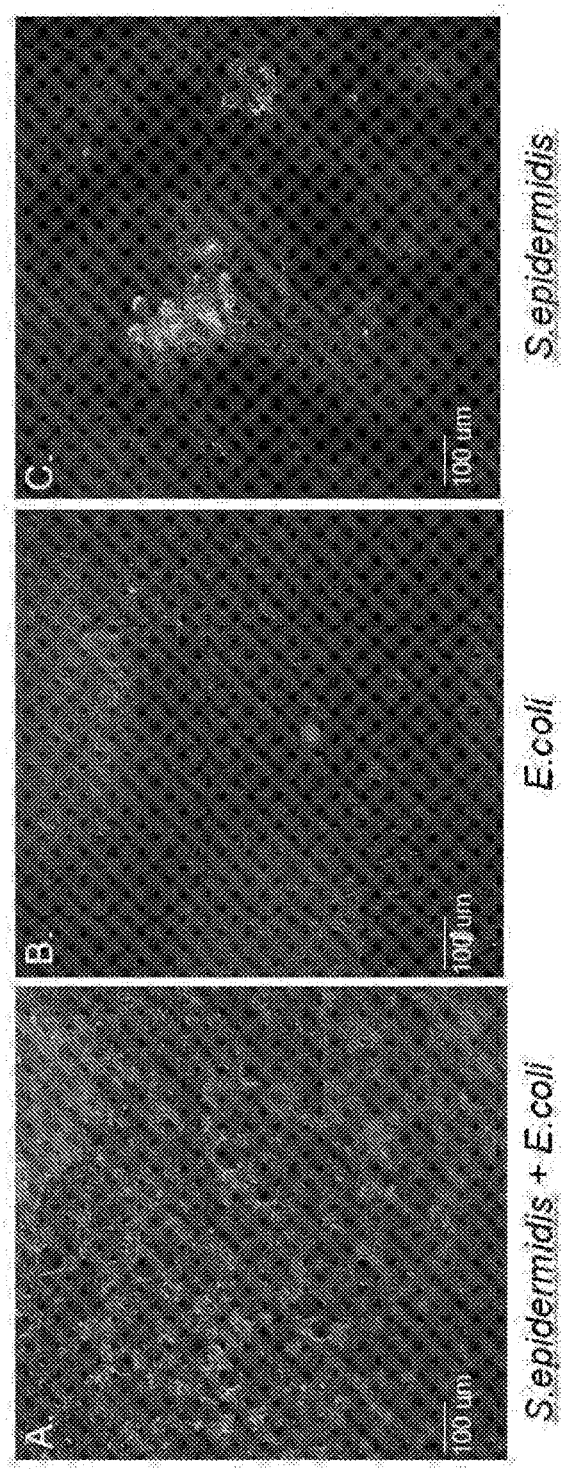
FIG. 26 shows an example of distinguishing bacteria that are gram-positive from gram-negative using different DNA dyes. The three images are taken from different bacterial mixtures that were analyzed using the same, rapid staining assay. Bacterial mixtures analyzed: A) a mixture of bacterial species, B) E. coli only, C) S. epidermidis only.

Imaging:
After a 60 second incubation period, fluorescent and bright field images of the assay were taken using the iPhone 6s. Only gram-positive bacteria appear orange, whereas both gram-positive and gram-negative bacteria may stain green (FIG. 26).

Example 2

Rapid CD4 Immunostaining

Materials

1. CD4 Antibodies: Ab34276 (Abeam) and 10R-CD4KHUP (Fitzgerald industrial international)
2. Antibody labeling kits:
2.1 Alexa Fluor 647 NHS ester kit (A37573, Thermofisher) 102.2 Zenon mouse IgG1 antibody labeling kit (Z25008, Thermofisher)
3. SYTO62 red fluorescent nucleic acid stain (S11344, Thermofisher) 5 mM in DMSO
4. Bioworld antibody bio-stabilizer 1OX (22050005-2, Fisher Scientific)
5. TRITON X-100™ (X-100 100 ml, Sigma)

Methods

1. Antibody Double-Labeling Method:
1.1. Primary fluorescent label: 100 µg of each CD4 detection antibody (Ab34276 and 10R-CD4KHUP) was labeled using the Alexa Fluor 647 NHS ester labeling kit (Thermofisher) following the manufacturer's protocol. After labeling the antibodies, residual dye was removed using a Sephadex-G25 column (17-0853-01, GE Health).

Purified antibodies were resuspended to a final concentration of 1 µg/ul in a mixture composed of 30% glycerol and 1% BSA. Antibodies were stored at −20° C. before further use.

1.2. Secondary fluorescent label: The Alexa Fluor 647 NHS ester labeled CD4 antibodies were labeled a second time using the Zenon Alexa Fluor 647 labeling kit (Fe-domain
labeling) following the manufacturer's instruction. Briefly, 1 µg of each CD4 antibody was mixed with 8 ul of mouse IgG1 Alexa Fluor 647 labeling reagent in 15 ul PBS. The reaction mixture was incubated at room temperature for 5 minutes and then kept at 4° C. before further use. This double-labeling method significantly enhances the fluorescence signal of the CD4 specific antibodies.

2. Detection Antibody Mixtures:
3D Assay: 6 µg/ml of each detection antibody that had been double-labeled is mixed together with 5 uM SYTO 62 (Red fluorescent DNA dye from Thermofisher), 0.SX of antibody bio-stabilizer (Bioworld), and 0.1% TRITON X-100™ (Sigma) in PBS. This mixture, therefore, has a final antibody concentration of 12 µg/ml mixed together with a dye that will stain DNA.

2A Assay: 6 µg/ml of each detection antibody that had been double-labeled is mixed together with 0.SX of antibody bio-stabilizer (Bioworld) and 0.1% TRITON X-100™ (Sigma) in PBS. This mixture also has a final antibody concentration of 12 µg/ml but the DNA dye is omitted.

1A Assay: 6 µg/ml of one detection antibody that had been double-labeled is mixed together with the 0.SX of antibody bio-stabilizer (Bioworld, and 0.1% TRITON X-100™ (Sigma) in PBS. This mixture only contains a final antibody concentration of 6 µg/ml without the DNA dye.

1D Assay: 6 µg/ml of one detection antibody that had been double-labeled is mixed together with 0.5× of antibody bio-stabilizer (Bioworld, and 0.1% TRITON X-100™ (Sigma) in PBS. This mixture only contains one antibody with the DNA dye.

3. Surface Treatment of the Q-Cards:
   3.1. Both the X-plate (containing 10 um pillars) and the substrate plate were treated with 1% NaOH for 1 hour at 50° C. Both plates were subsequently washed with distilled water, PBS, and distilled water once again for 5 minutes for each wash.
   3.2. After washing the plates, they were blocked with 4% BSA for 2 hours at room temperature. The plates were washed to remove residual BSA by distilled water twice for 5 minutes, then air-dried.

4. Printing of the Antibody Mixture onto the Q-Card:
   4.1 The prepared antibody mixture was printed at approximately 3 ul/cm² on both plates (X-plate and substrate plate). Once the antibodies had been printed, the plates were air dried and protected from the light before further use.

Figure 27:
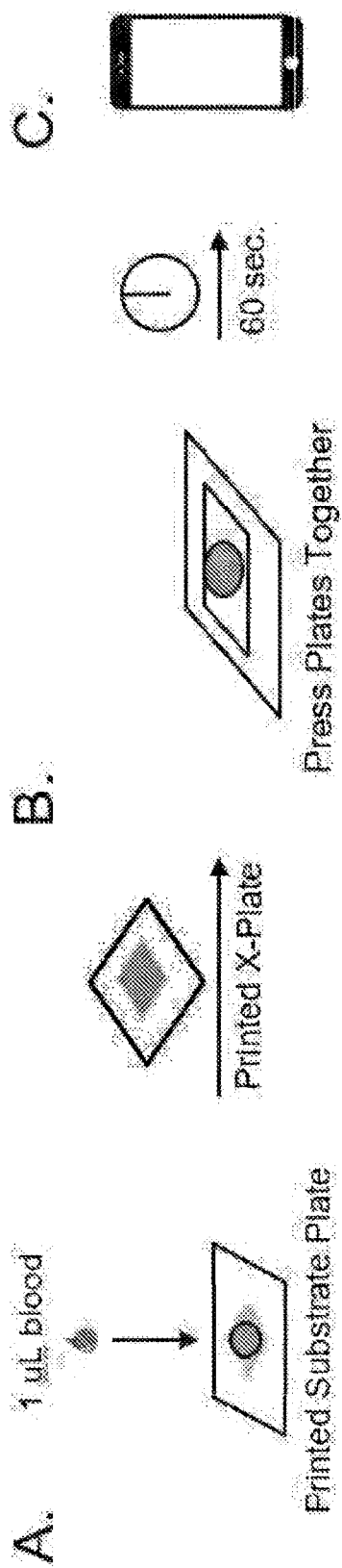
FIG. 27 shows Q-card assembly and immunoassay imaging. A, After preparing the Q-card plates, 1 ul of whole blood can be added to the substrate plate. B, The X-plate is subsequently pressed onto the substrate plate containing the blood sample. C, The immunoassay is incubated for one minute at room temperature after which time pictures are immediately taken using an iPhone 6s.
Figure 28:
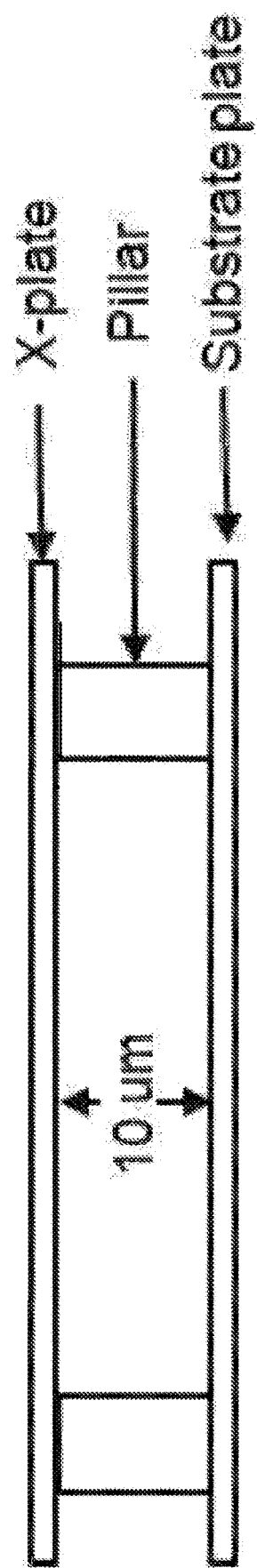
FIG. 28 shows a schematic illustration of a Q-Card: The Q-card is composed of a substrate plate and an X-plate that is engineered to have 10 um pillars. The final gap between the plates is equal to the height of the pillars.
Figure 29:
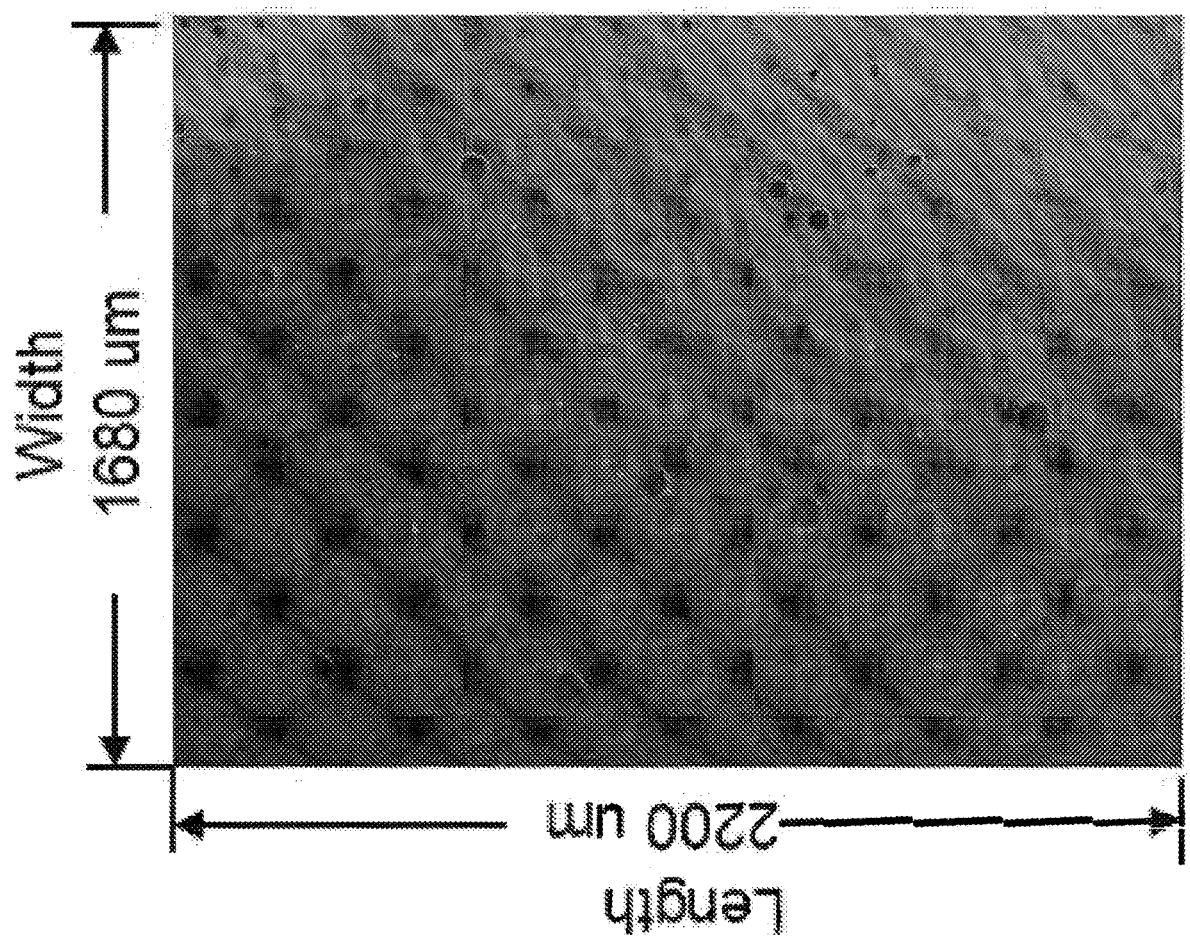
FIG. 29 an example of an iPhone 6s CD4 T-Cell Count: The length and width of the iPhone 6s field of view is displayed. These dimensions are used to calculate the average CD4 T-cell count per ul of blood.

5. CD4 Detection Using the iPhone Gs:
   5.1. 2 ul of fresh, whole blood was added to the prepared substrate plate (FIG. 27, FIG. 28). The prepared x-plate was then pressed firmly onto the blood sample. Pictures were taken after one 1 minute of incubation using an iPhone 6s.

6. CD4 Count Per Microliter Calculation:
   6.1. X-plate pillar height: 10 um
   6.2 fov: field of view (the total area of the Q-card in the picture that is taken using either an iPhone or a fluorescent microscope)
   6.3. Volume of sample in a fov:
      6.3.1. Length (um) x Width (um) x Height (10 um)=Volume of the fov (um³)
   6.4. 1 ul=$10^9$ um³
   6.5. CD4 counts per microliter:
      6.5.1: CD4 counts in the FOV X $10^9$ um³/volume of the FOV (um³)
      Total CD4 Counts·X 1e9 um 1
      Volume of FOV um-'uL
   6.6. Example: in the iPhone picture below, there were 31 CD4 positive signals
      6.6.1. CD4 counts per micrometer:
      31×10 9 um 3/(1680 um×2200 um×10 um)
      =31×$10^9$ um³/3.7×$10^7$ um³=838/ul Example 3

RNA Fluorescence In Situ Hybridization (RNA-FISH)

RNA fluorescence in situ hybridization (RNA-FISH) is a molecular cytogenetic technique to detect and localize specific RNFigA targets (mRNA, lncRNA and miRNA) in single cells via fluorescence microscopy. The traditional RNA-FISH methods usually include multiple steps, e.g., fixation, permeabilization, hybridization and imaging. Although FISH has wide medical applications, the complexity of the technique limits its potential in rapid diagnostics. Therefore, it is desirable to develop a fast, accurate, portable, and/or inexpensive RNA-FISH assay, which can be conducted by a non-professional. The current invention satisfies these needs.

1. Materials

Stellaris® FISH Probes, Human GAPDH with Quasar® 670 Dye (BioSearch Technologies, cat #SMF-2019-1). Q-card with 10 μm height of pillar.

2. Procedures

Coating plate. X-plate with 10 um pillar was printed with 1 nM of Quasar® 670 labeled FISH probes with different concentration of Zwittergent (Sigma-Aldrich) as surfactant and air-dried. Adding sample. 3 μL fresh whole blood was dropped onto the center of substrate plate and covered by X-plate. Staining. The card was incubated at room temperature for 1 minute. Imaging. The stained card was imaged by iPhone 6s with external laser illumination.

3. Results

Figure 30:
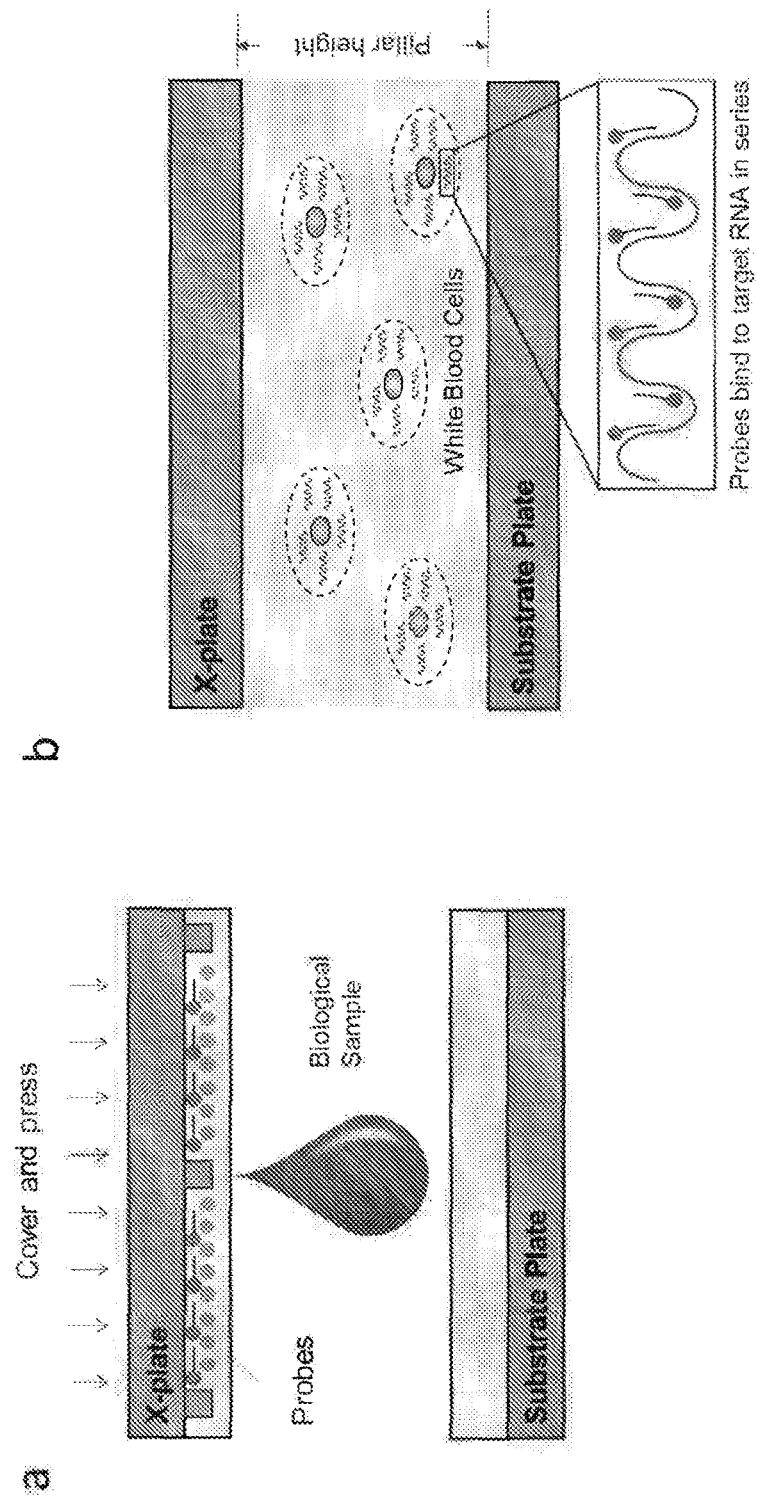
FIG. 30 (a) shows an embodiment of a X-FISH device, which comprises a first plate (X-plate) and a second plate (substrate plate). Specific probes and surfactants (e.g. Zwittergent) are printed on X-plate. After drop blood samples on substrate plate, X-plate is covered and pressed on substrate plate. One minute later, the device is inserted to smart phone device for imaging and analyzing. (b) is an illustration to detect specific RNA expressed in white blood cells by X-FISH. Pillars on X-plates make a gap between the two plates, where the assay takes place. Printed probes and surfactants (e.g. Zwittergent) are dissolved in blood. surfactants (e.g., Zwittergent) lysate red blood cells, and also permeabilize white blood cells to promote probes enter cells to bind target RNA. Of note, the probes are designed to bind target RNA in series to amplify signals.

FIG. 30 (a) shows an embodiment of a X-FISH device, which comprises a first plate (X-plate) and a second plate (substrate plate). Specific probes and surfactants (e.g. Zwittergent) are printed on X-plate. After drop blood samples on substrate plate, X-plate is covered and pressed on substrate plate. One minute later, the device is inserted to smart phone device for imaging and analyzing. (b) is an illustration to detect specific RNA expressed in white blood cells by X-FISH. Pillars on X-plates make a gap between the two plates, where the assay takes place. Printed probes and surfactants (e.g., Zwittergent) are dissolved in blood. surfactants (e.g., Zwittergent) lysate red blood cells, and also permeabilize white blood cells to promote probes enter cells to bind target RNA. Of note, the probes are designed to bind target RNA in series to amplify signals.

Figure 31:
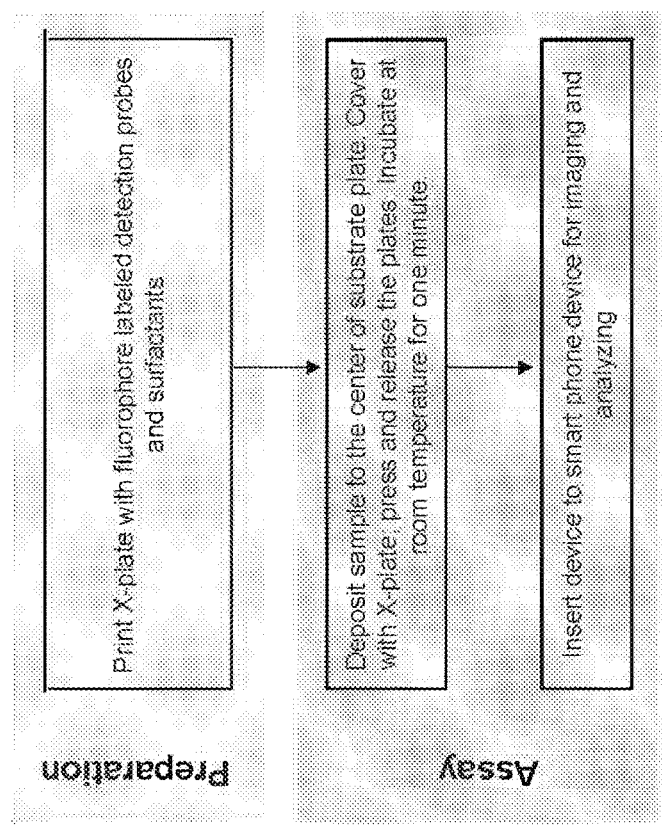
FIG. 31 is a flowchart for X-FISH. Preparation is to print X-plate with fluorophore labeled detection probes and surfactants. Assay includes apply sample to substrate plate, cover with X-plate, incubate at room temperature for one minute, and insert to smart phone device for readouts.

FIG. 31 is a flowchart for X-FISH. Preparation is to print X-plate with fluorophore labeled detection probes and surfactants. Assay includes apply sample to substrate plate, cover with X-plate, incubate at room temperature for one minute, and insert to smart phone device for readouts.

Figure 32:
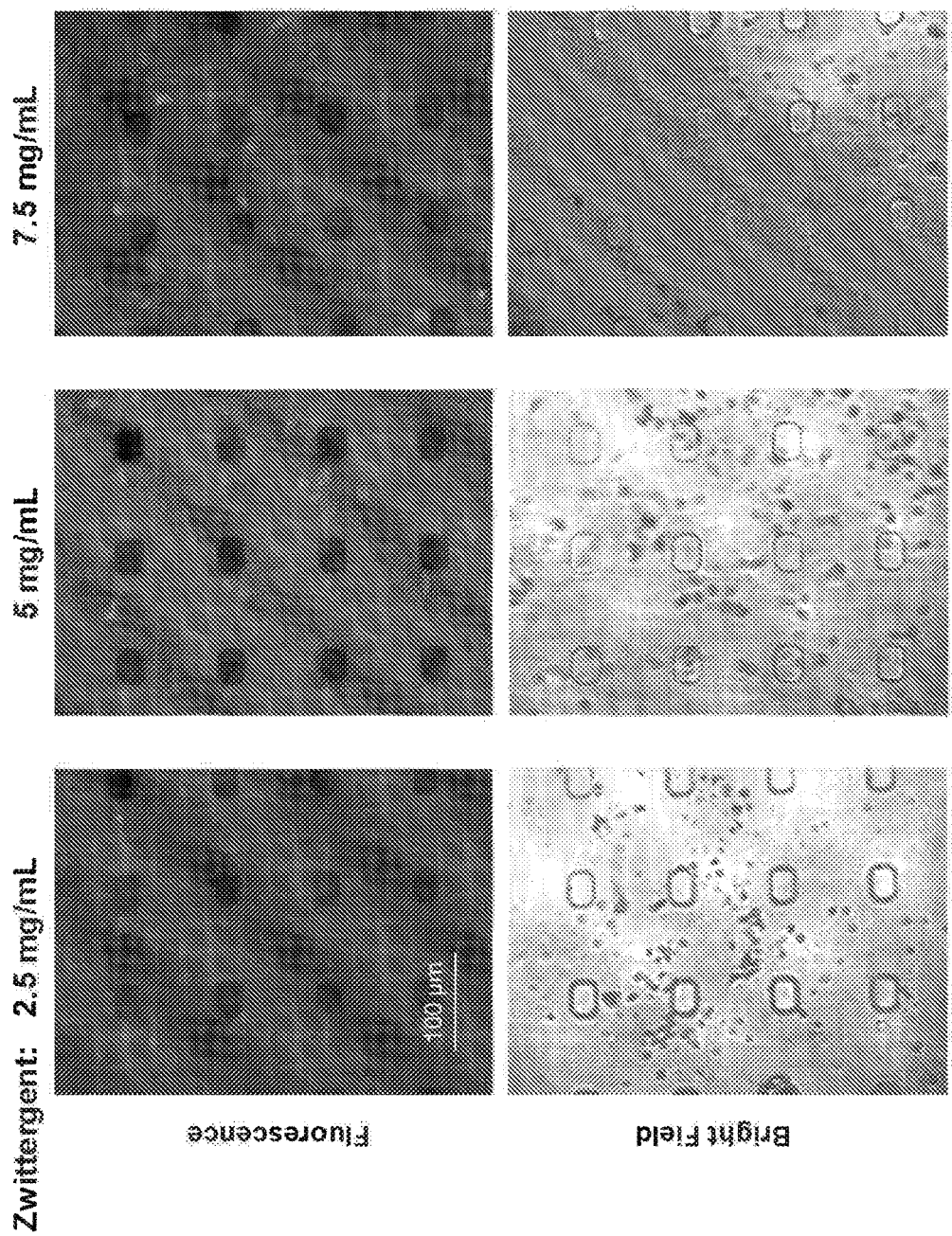
FIG. 32 shows effects of different Zwittergent concentrations on red blood cell lysate and white blood cell permeabilization. 2.5 mg/mL Zwittergent gives limited amount of fluorescence-labeled white blood cells. 5 mg/ml Zwittergent boosts the amount of fluorescence-labeled white blood cells by increasing probe penetration. However, 7.5 mg/ml Zwittergent decreases the amount of fluorescence-labeled white blood cells by inducing cell lysis.

FIG. 32 shows effects of different Zwittergent concentrations on red blood cell lysate and white blood cell permeabilization. 2.5 mg/ml Zwittergent gives limited amount of fluorescence-labeled white blood cells. 5 mg/ml Zwittergent boosts the amount of fluorescence-labeled white blood cells by increasing probe penetration. However, 7.5 mg/ml Zwittergent decreases the amount of fluorescence-labeled white blood cells by inducing cell lysis.

Example 4

Chlamydia Staining

In the experiments, mouse anti-chlamydia (Abeam, cat #ab41196) was used for staining and chlamydia antigen control slide (MBL Bion, cat #QCHE-4502) was used as the device to hold the sample.

As shown in panel (A), 20 ul Dylight633 labeled anti-Chlamydia antibody (Abeam) was added to sample slide that carries fixed human tissue cells infected by Chlamydia. The reactants were incubated for a predetermined period of time. The suggested time period is 30 minutes. Then the slide was washed and the cells were imaged by microscope. As shown in panel (B), for QMAX staining: 1 ul Dylight633 labeled anti-Chlamydia antibody was added to sample slide that carries fixed human tissue cells infected by Chlamydia. The labeled antibody was then covered by X-plate (30 um pillar height) for 15 seconds (or longer). In some experiments, as an optional step, the X-plate is removed and the stained slide is washed by dipping into PBST for 3 times and air dried. In some experiments, the slides were not washed. The stained slide and cells were imaged by microscope.

For the conventional method, 20 ul of labeled Ab is the minimum amount for effective staining, compared to 1 ul with the QMAX method.

FIG. 2 shows exemplary pictures of chlamydia staining with the QMAX device. Panel (A) illustrates the results for the experiments using a 15 second incubation with the antibody to chlamydia; panel (B) illustrates the results for the experiments using a 30 second incubation with the antibody to chlamydia. DL633 refers to Dylight633 labeled; BF refers to bright field. The "ug/ml" numbers refer to antibody concentration.

In the experiments shown in FIG. 2, slides with fixed human tissue cells infected by chlamydia were incubated with 1 ul of Dylight633 labeled anti-chlamydia antibody with different concentration for 15 seconds (panel A) or 30 seconds (panel B). X-plate with 30 um pillar height was used in the QMAX immunostaining. The slides were then washed by PBST and images were taken by microscope. BF: bright field. DL633: Dylight633 fluorescence.

Figure 3:
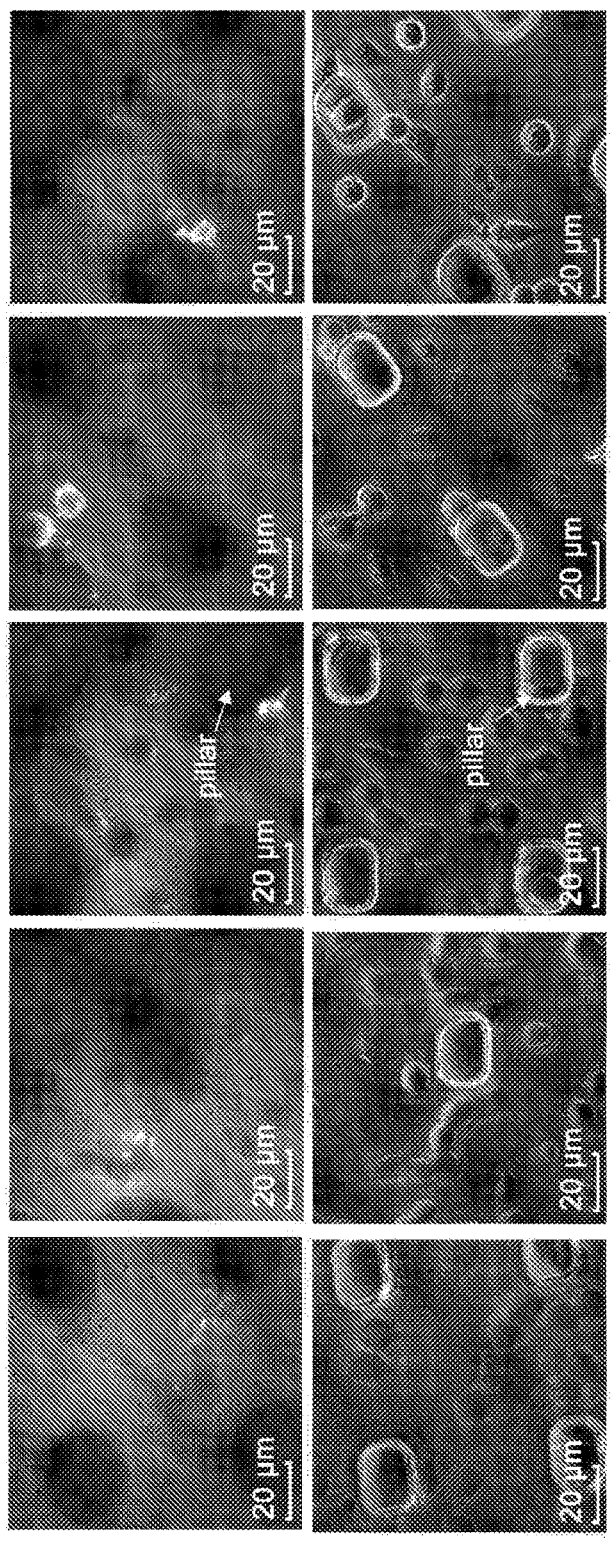
FIG. 3 shows exemplary pictures of chlamydia staining with the QMAX device without the optional washing step.

FIG. 3 shows exemplary pictures of chlamydia staining with the QMAX device without the optional washing step. In the experiments shown in FIG. 3, slides with fixed human tissue cells infected by chlamydia were incubated with 1 ul of Dylight633 labeled anti-chlamydia antibody with 40 ug/ml for 2 min. X-plate with 30 um pillar height was used in the QMAX immunostaining. Images were taken by microscope without washing. BF: bright field. DL633: Dylight633 fluorescence.

Figure 4:
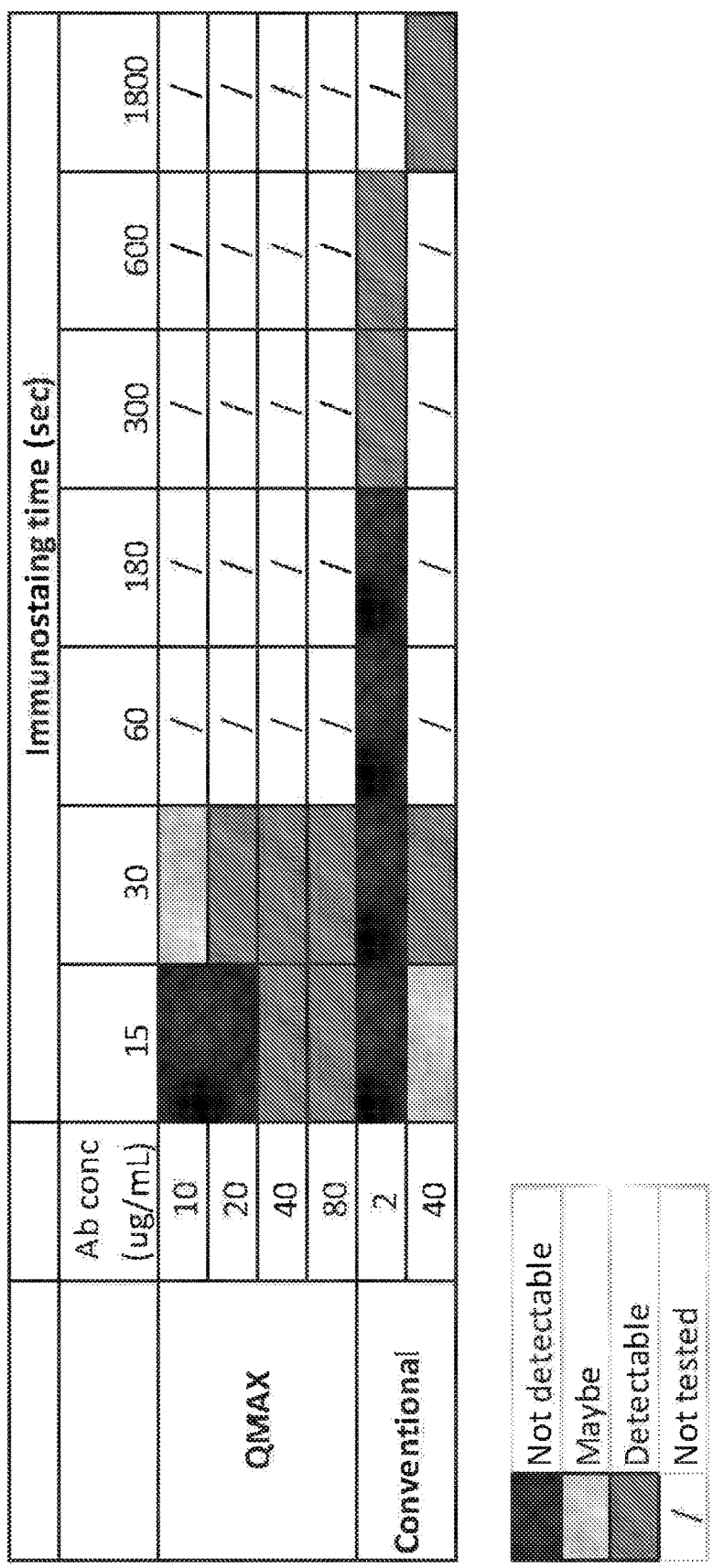
FIG. 4 provides a summary of the results from conventional staining and the staining using a QMAX device.

FIG. 4 provides a summary of the results from conventional staining and the staining using a QMAX device. It is noted that QMAX immunostaining of Chlamydia can be detected after 15s (40 μg/mL).

Figure 5:
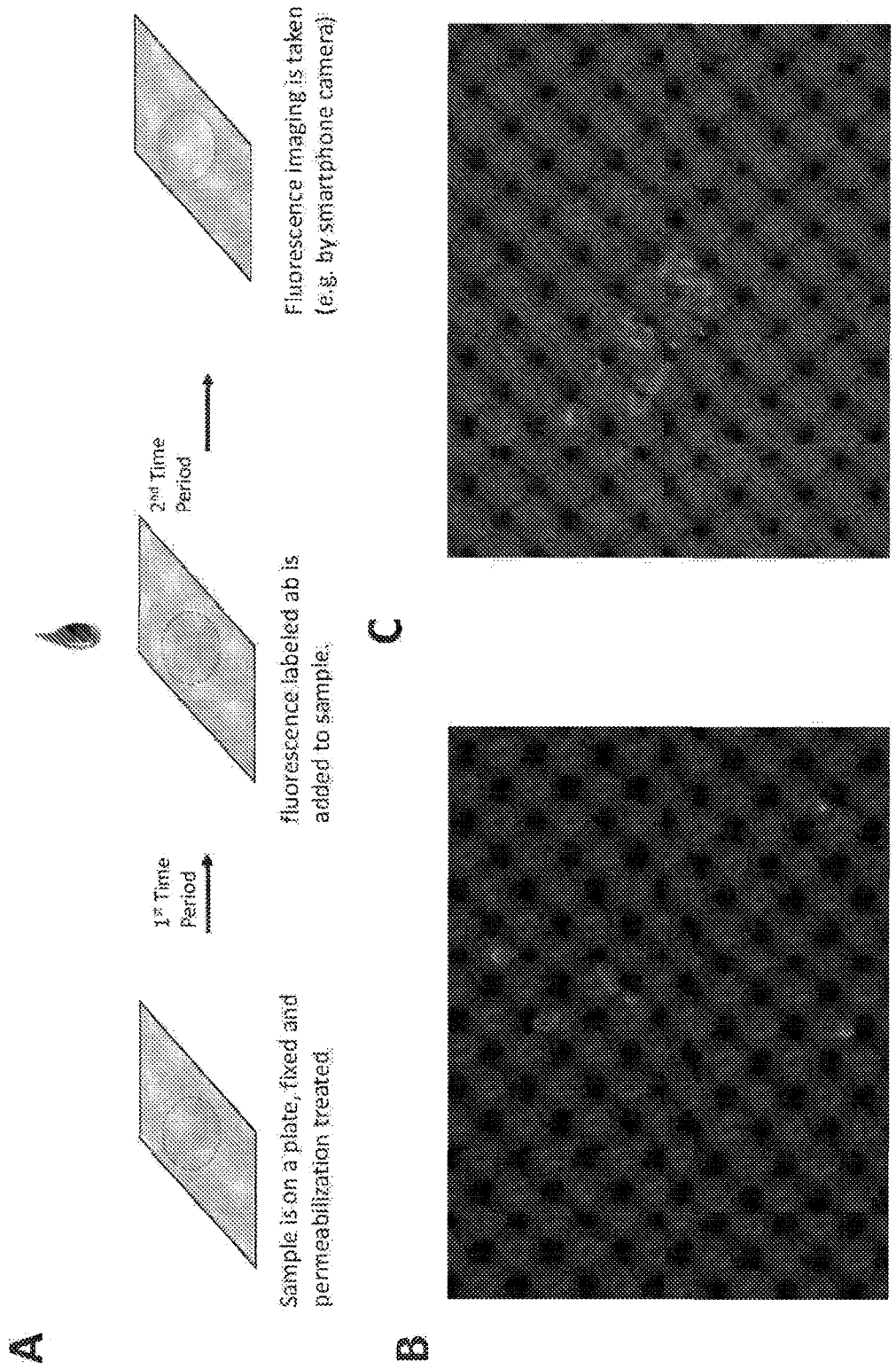
FIG. 5 shows schematic design and results for the staining of chlamydia infected cells. Panel (A) shows the design of the staining process; panel (B) shows an image of immunostaining of Chlamydia infected cells taken with the camera of a smart phone, with one step washing; panel (C) shows an image of immunostaining of Chlamydia infected cells taken with the camera of a smart phone, with no washing.

FIG. 5 shows schematic design and results for the staining of chlamydia infected cells. Panel (A) shows the design of the staining process. In some embodiments, the sample is placed on a plate. In certain embodiments, the sample includes cells that are suspected to be infected by chlamydia. In certain embodiments, the sample is immobilized on the plate. In certain embodiments, the sample is fixed and/or permeabilized. In certain embodiments, the sample is not immobilized.

Panel (B) shows an image of immunostaining of Chlamydia infected cells taken with the camera of a smart phone, with one step washing. Panel (C) shows an image of immunostaining of Chlamydia infected cells taken with the camera of a smart phone, with no washing.

Figure 6:
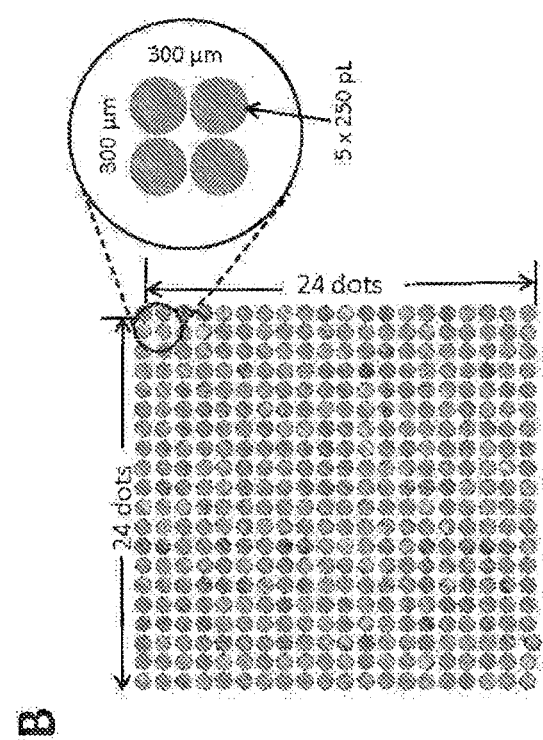
FIG. 6 shows schematic illustrations of the QMAX device, which is prepared for a one-step sandwich assay for the detection of chlamydia. Panel (A) shows an illustration of the X-plate, to which detection antibodies are attached; panel (B) shows an illustration to demonstrate how the antibody is printed on the X-plate; panel (C) shows an illustration of a PMMA substrate, to which capturing antibodies are attached.
Figure 6:
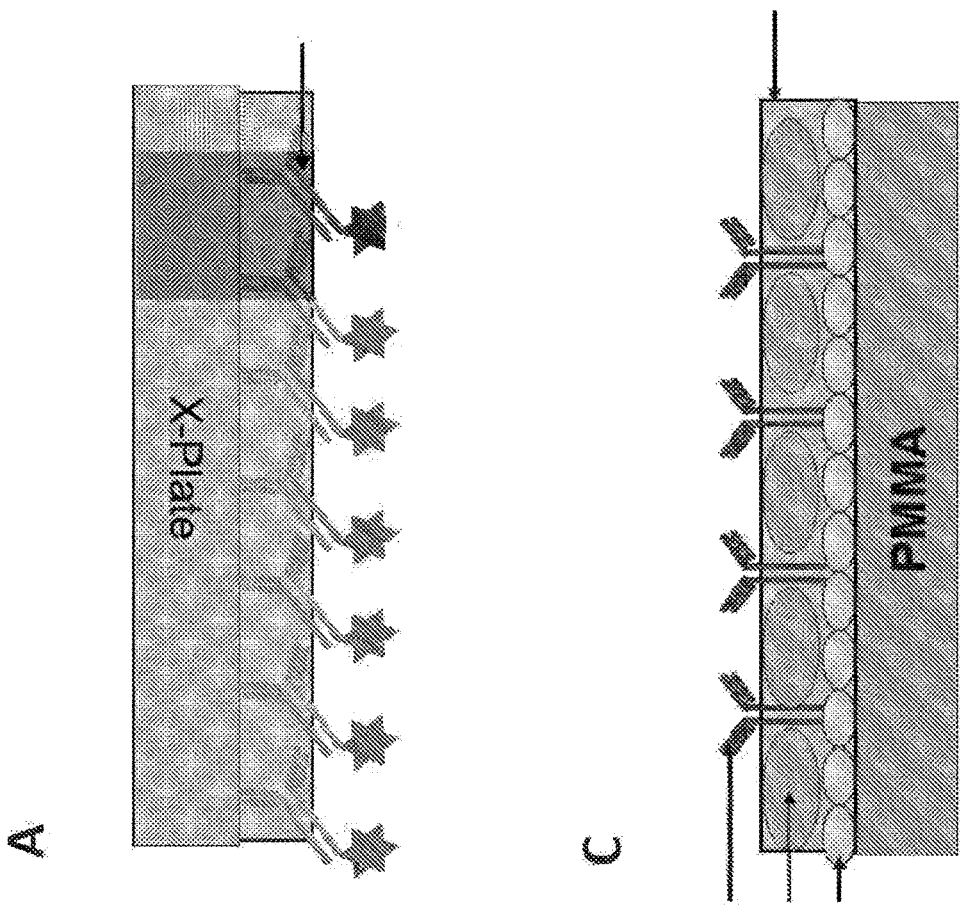

FIG. 6 shows schematic illustrations of the QMAX device, which is prepared for a one-step sandwich assay for the detection of chlamydia. Panel (A) shows an illustration of the X-plate, to which detection antibodies are attached; panel (B) shows an illustration to demonstrate how the antibody is printed on the X-plate; panel (C) shows an illustration of a PMMA substrate, to which capturing antibodies are attached.

As shown in panel (B) of FIG. 6, Nanoprint Dylight633-anti-chlamydia detection antibody (100 μg/mL) in PBST and 1:100 commercial protein stabilizer on pre-cut X-Plates, dry at room temperature.

Setup: 8×2 arrays, 24×24 dots per array, 5×250 pl per dot. Array size: 7.2 mm×7.2 mm. Gap between dots: 300 um.

PMMA as binding site: 100 ul Protein A 20 μg/ml in PBS coat substrate overnight/Wash 3× with PBST; 100 ul Capture Ab 20 μg/ml in PBS coat substrate for 3 h/Wash 3× with PBST; 100 ul Blocking the substrate with 4% BSA in PBS for 2 h/Wash 3× with PBST; incubate 100 ul StabilCoat stabilizer for 1 h/pipette excessive/Dry at RT. It is noted that 6.5×6.5 mm FlexWell was used on PMMA.

The antibodies used in the experiments shown in the sandwich assays are listed in the Table below.

| Antibody | Vendor | Cat# |
|---|---|---|
| Mouse anti-chlamydia (Capture antibody) | Fitzgerald | 10-C13A |
| Mouse anti-chlamydia (Capture antibody) | Fitzgerald | 10-C13B |

Figure 7:
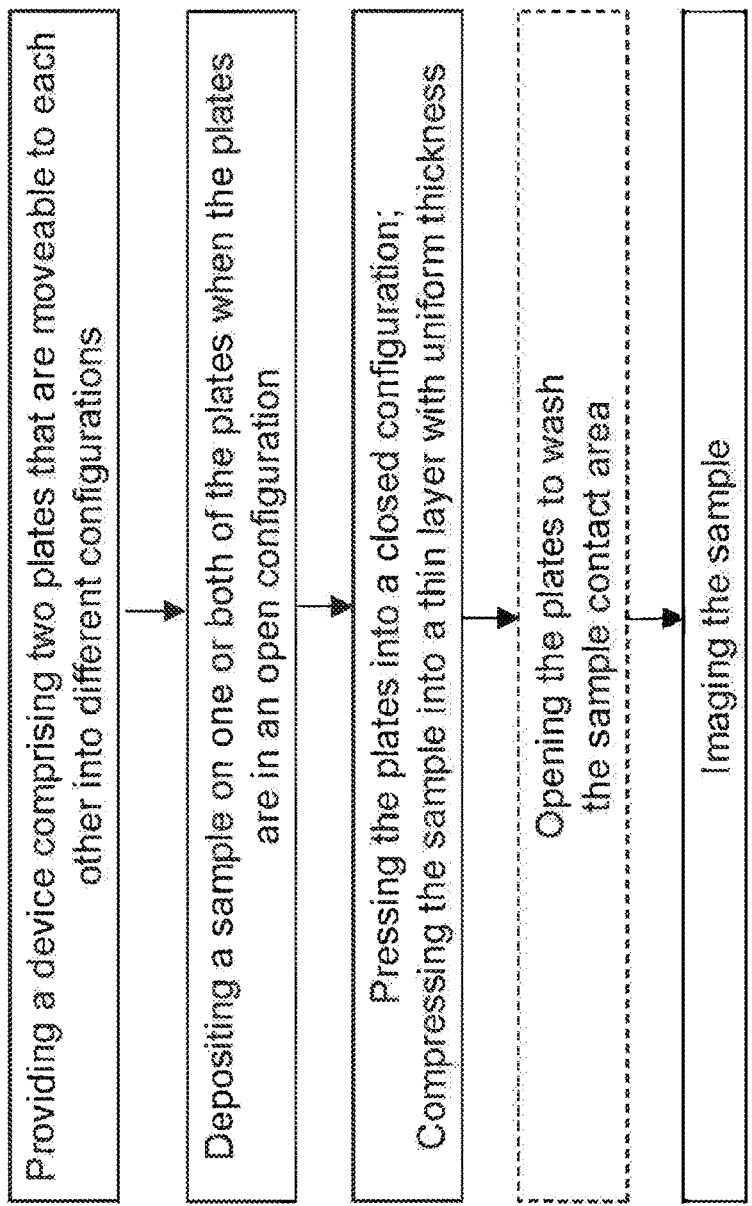
FIG. 7 shows an exemplary flow chart that demonstrates the process to conduct the sandwich assay to detect chlamydia.

FIG. 7 shows an exemplary flow chart that demonstrates the process to conduct the sandwich assay to detect chlamydia. In some experiments, a series samples, each with a volume of 0.8 ul, containing different concentrations of chlamydia analyte were deposited on coated substrate at different locations. X-plate nanoprinted with the detection antibody was pressed on top of the liquid by hand. The reactants were incubated for 2 min. In some experiments, one step washing was performed: peel off the X-plate; wash the substrate plate binding site in PBST for 1 min and then water briefly. The results were measure by Raman microscope.

Figure 8:
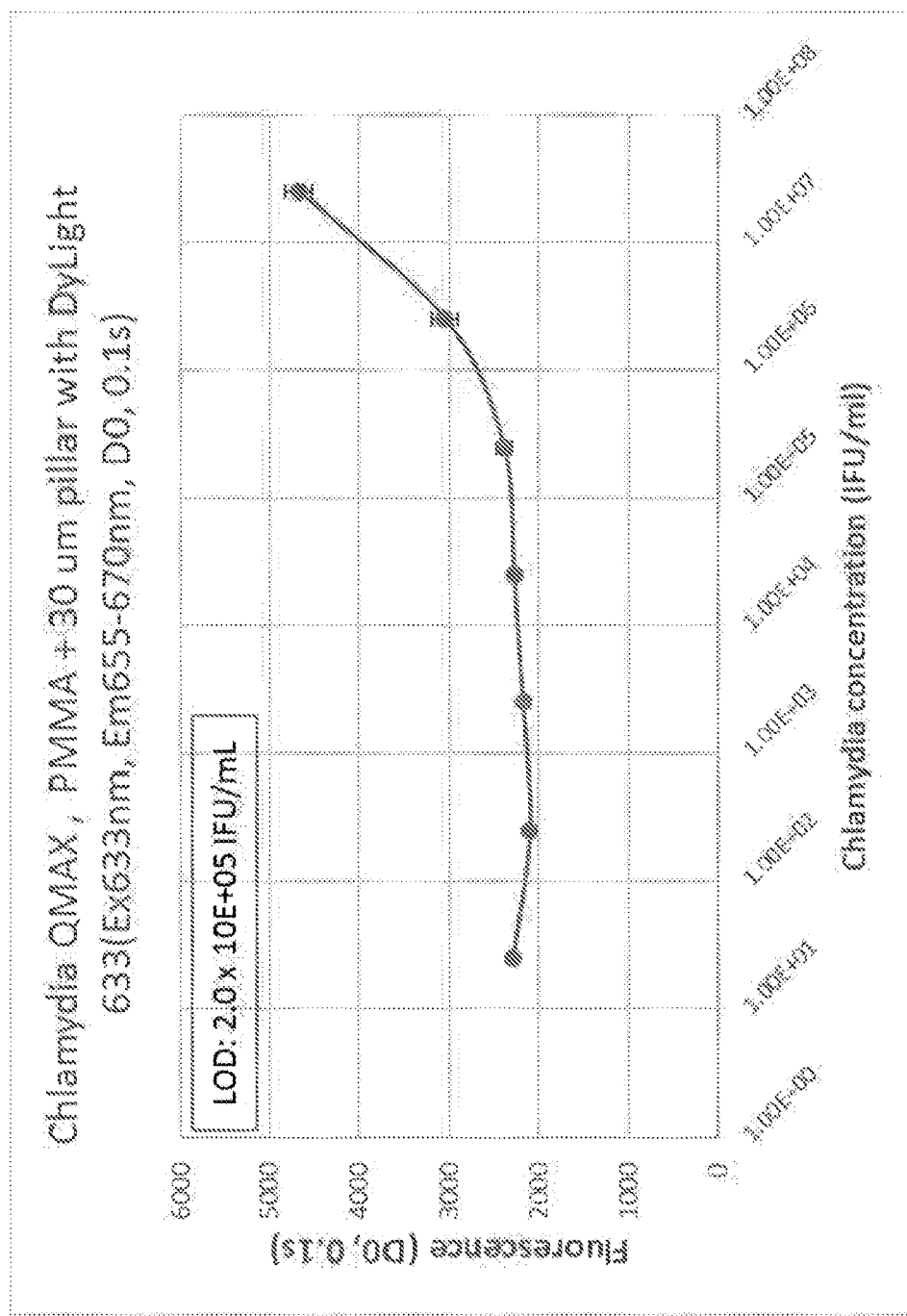
FIG. 8 show an example of the results of sandwich assays that detect chlamydia.

FIG. 8 show an example of the results of sandwich assays that detect chlamydia. FIG. 8 provides a standard curve of chlamydia QMAX sandwich immunoassay. 1 ul of purified chlamydia elementary bodies (EB) were used in the QMAX assay. Limit of detection (LOO): 2×10E+05 IFU/mL, or 200 IFU per test.

Additional Examples of Present Invention

One Step Staining Assay to Detect Chlamydia

AA1 A method for detecting chlamydia in a sample, comprising:
  (a) obtaining a first plate comprising, on its inner surface, a sample contact area that is configured to contact a sample;
  (b) depositing the sample in the sample contact area, wherein the sample is suspected to comprise cells infected with chlamydia; and
  (c) depositing a chlamydia staining medium on the sample, wherein the staining medium comprises a chlamydia-binding antibody, and the staining medium and the sample form a mixture;
  (d) covering the mixture of the sample and the staining medium with a second plate,
  (e) pressing the first plate and the second plate so that at least part of the mixture is compressed into a thin layer;
  (f) incubating for a predetermined period of time that is about 60 seconds or less; and
  (g) detecting a chlamydia-related signal from the mixture.

AA2 The method of any prior embodiments, wherein the predetermined period of time that is about 30 seconds or less.

AA3 The method of any prior embodiments, wherein the predetermined period of time that is about 15 seconds or less.

AA4 The method of any prior embodiments, wherein the chlamydia antibody is fluorescently labeled.

AA5 The method of any prior embodiments, wherein the thin layer has a uniform thickness that is less than 100 um.

AA6 The method of any prior embodiments, wherein the thin layer has a uniform thickness that is less than 50 um.

AA7 The method of any prior embodiments, wherein the thin layer has a uniform thickness that is about 30 μm or less.

AA8 The method of any prior embodiments, wherein the chlamydia-related signal is detected by imaging the sample.

One Step Sandwich Assay for Testing Chlamydia

AB1 A method for detecting chlamydia in a sample, comprising:
- (a) obtaining a first plate comprising, on its inner surface, a sample contact area that has a binding site, wherein the binding site comprises an immobilized capture antibody that binds to chlamydia in a sample that is suspected to contain chlamydia;
- (b) obtaining a second plate comprising, on its inner surface, a sample contact area that has a storage site, wherein the storage site comprises a detection antibody that is capable of, upon contacting the sample, diffusing in the sample, and wherein the capture antibody and detection antibody bind to different sites in the chlamydia to form a capture antibody-chlamydia-detection antibody sandwich;
- (c) depositing the sample on one or both of the sample contact areas of the plates;
- (d) after (c), bringing the two plates to a closed configuration, wherein, in the closed configuration, at least part of the sample deposited in (c) is confined between the sample contact areas of the two plates, and has an average thickness in the range of 0.01 to 200 um; and
- (e) detecting a signal related to chlamydia captured by the capture antibody.

AB2. The method of any prior AB embodiments, wherein the sample is from a human subject.

AB3. The method of any prior AB embodiments, wherein the capturing site further comprises a protein stabilizer.

AB4. The method of any prior AB embodiments, wherein the storage site further comprises a protein stabilizer.

AB5. The method of any prior AB embodiments, wherein the detection antibody comprises a fluorescent label.

AB6. The method of any prior AB embodiments, wherein the sample between the two plates has a uniform thickness in the range of 0.5 to 50 um.

AB7. The method of any prior AB embodiments, wherein the sample between the two plates has a uniform thickness in the range of 1 to 35 um.

AB8. The method of any prior AB embodiments, further comprising determining the presence or absence of chlamydia.

AB9. The method of any prior AB embodiments, wherein the overall time for steps (a) to (e) is less than 10 minutes.

AB10. The method of any prior AB embodiments, wherein the overall time for steps (e) to (e) is less than 3 minutes.

AB11. The method of any prior AB embodiments, wherein the overall time for steps (a) to (e) is less than 2 minutes.

Additional Features

AC1. The method of any prior embodiments, wherein one or both of the sample contact areas comprise spacers, wherein the spacers regulate the spacing between the sample contact areas of the plates when the plates are in the closed configuration.

AC2. The method of any prior embodiments, wherein the first plate comprises a plurality of binding sites and the second plate comprises a plurality of corresponding storage sites, wherein each biding site faces a corresponding storage site when the plates are in the closed configuration.

AC3. The method and device of any prior embodiment, wherein the detection antibody is dried on the storage site.

AC4. The method of any prior embodiments, wherein the capture antibody at the binding site are on an amplification surface that amplifies an optical signal of the analytes or the captured detection agents in any prior embodiments.

AC5. The method of any prior embodiments, wherein the capture agents at the binding site are on an amplification surface that amplifies an optical signal of the analytes or the captured detection agents in any prior embodiments, wherein the amplification is proximity-dependent in that the amplification significantly reduced as the distance between the capture agents and the analytes or the detection agents increases.

AC6. The method of any prior embodiments, wherein the detection of the signal is electrical, optical, or both (including but not limited to Fluorescence, SPR, etc.).

B. Quantifying CD4 Expressing Cells

Figure 9:
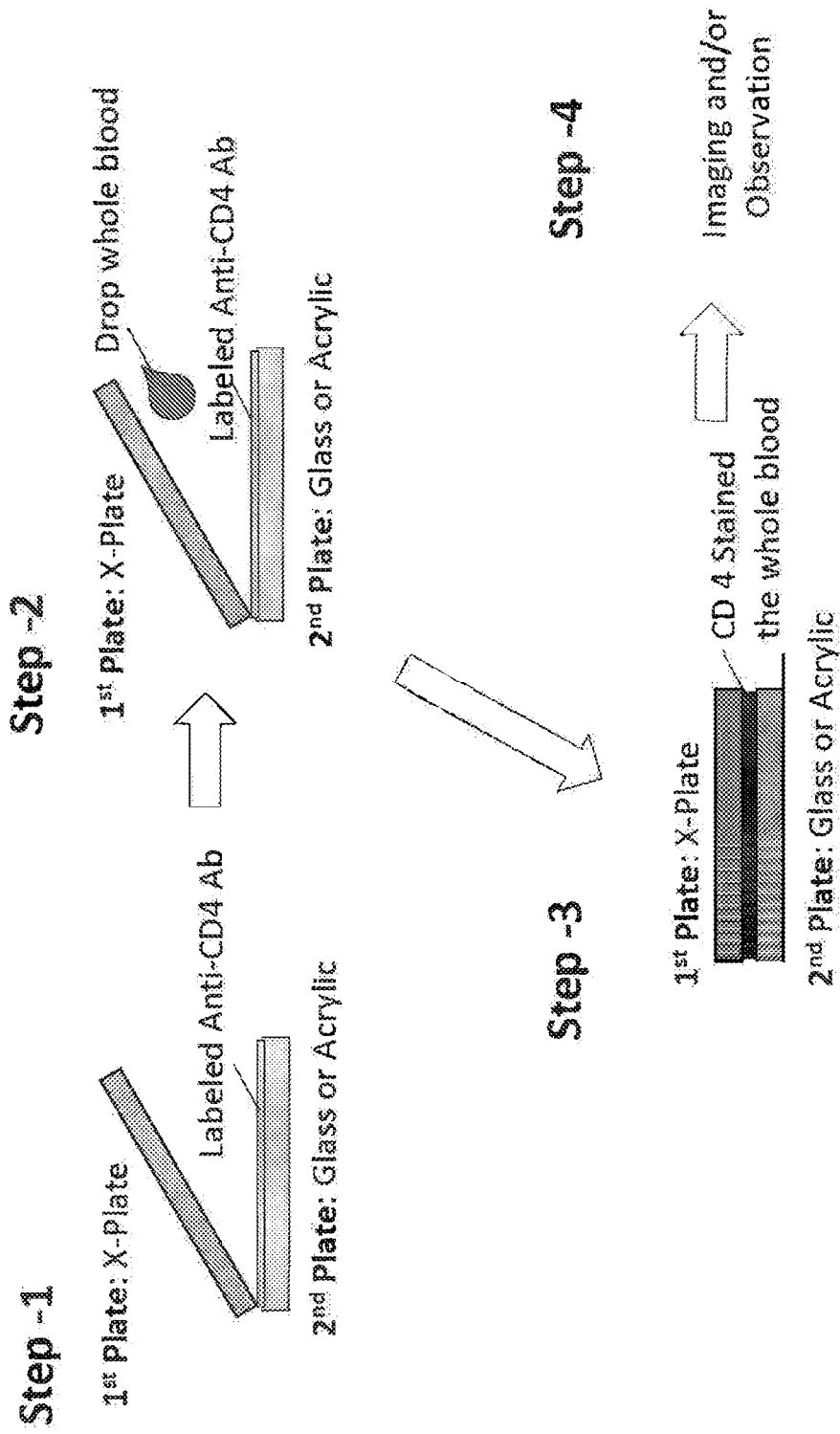
FIG. 9 provides schematic illustrations showing the processes for staining of CD4 expressing cells according to some embodiments of the present invention.

FIG. 9 provides schematic illustrations showing the processes for staining of CD4 expressing cells according to some embodiments of the present invention.

As shown in FIG. 9, in some embodiments, a first plate (termed "X-plate") and a second plate (e.g. made from glass or acrylic) were obtained, wherein the first plate and the second plate are moveable relative to each other. In certain embodiments, the first plate and the second plate are not connected. In certain embodiments, the first plate and the second plate are connected by a turning structure (e.g. a hinge). Each of the plates have two surfaces: one inner surface and one outer surface, wherein the inner surfaces face each other when the plates are pressed against each other. On the inner surfaces, each plate comprises a sample contact area for contacting a liquid sample.

In some embodiments, a detecting agent (e.g. a labeled anti-CD4 antibody) is immobilized on the sample contact area of one or both of the plates. In certain embodiments, the detecting agent comprises an anti-CD4 antibody. In certain embodiments, the detecting agent is labeled with a fluorophore. In certain embodiments, as shown in FIG. 9, the anti-CD4 antibody is labeled with Alex 647.

In step 2, when the plates are in an open configuration, in which the plates are separated apart, a liquid sample is deposited on the sample contact area of one or both of the plates. In certain embodiments, as shown in FIG. 9, the sample is whole blood.

In step 3, the plates are pressed against each other into a closed configuration. In certain embodiments, the pressing is conducted with human hand. In the closed configuration, the plates are pressed against each other with a gap between them, and the sample is compressed into a thin layer. In certain embodiments, the thin layer has a uniform thickness. In certain embodiments, one of both of the plates comprise spacers that are fixed in one or both of the sample contact areas. When the plates are pressed into the closed configuration, the spacers regulate the thickness of the sample layer. In certain embodiments, the spacers have a pillar shape.

In step 4, the sample layer is imaged and the number of CD4 expressing cells are quantified.

In the experiments shown in FIG. 9, the QMAX device has two plates. The first plate was a X-Plate with 2 um or 10 um pillar height, 30×40 um pillar size, 80 um inter spacing distance, and is made of 175 um thick PMMA. The second plate was 1 mm thick glass or acrylic. The Anti-CD 4 antibody with label Alex 647 was on positioned on the second plate in either liquid form or dry form. In its liquid form, the anti-CD4 antibody is 5 to 50 µg/ml with a volume of 0.5 to 1 ul. The anti-CD4 antibody was printed into an array of 300 um period and dried, with a surface concentration of 1 to 100 ng/cm² after drying. In the experiments shown in FIG. 9, for step 2, the sample is fresh whole blood with a volume of ~1 ul. In the experiment shown in FIG. 9, for step 3, after the plates are pressed against each other, the sample layer is incubated with the detecting agent for about 60 seconds. In the experiment shown in FIG. 9, for step 4, the stained whole blood sample layer was imaged either with laboratory microscopy or with a mobile device-adaptor system.

Figure 10:
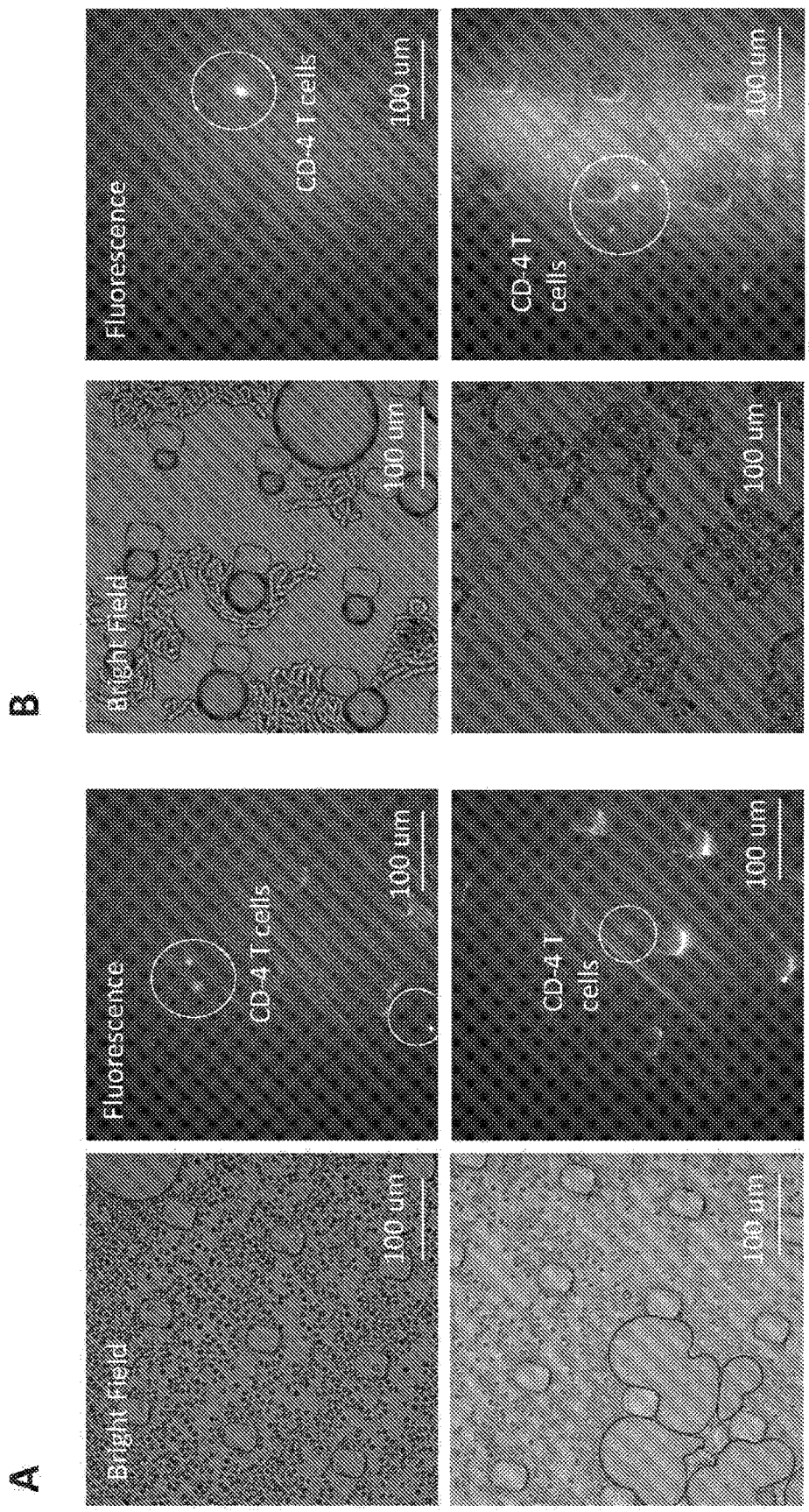
FIG. 10 shows exemplary pictures of CD4 staining with the QMAX device in bright field and fluorescence. The images were captured with inverted microscopy. Panel (A) illustrates the results for the experiments using a QMAX device with a 2 um gap; panel (B) illustrates the results for the experiments using a QMAX device with a 10 um gap.

FIG. 10 shows exemplary pictures of CD4 staining with the QMAX device in bright field and fluorescence. The images were captured with inverted microscopy. Panel (A) illustrates the results for the experiments using a QMAX device with a 2 um gap; panel (B) illustrates the results for the experiments using a QMAX device with a 10 um gap. As shown in FIG. 10, for panel (A), the bright field photo illustrates both red blood cells and white blood cells; the fluorescence photo shows clear fluorescence of stained CD4 T cells. As shown in FIG. 10, for panel (B), the bright field photo illustrates aggregated red blood cells and white blood cells; the fluorescence photo shows clear fluorescence of stained CD4 T cells.

Figure 11:
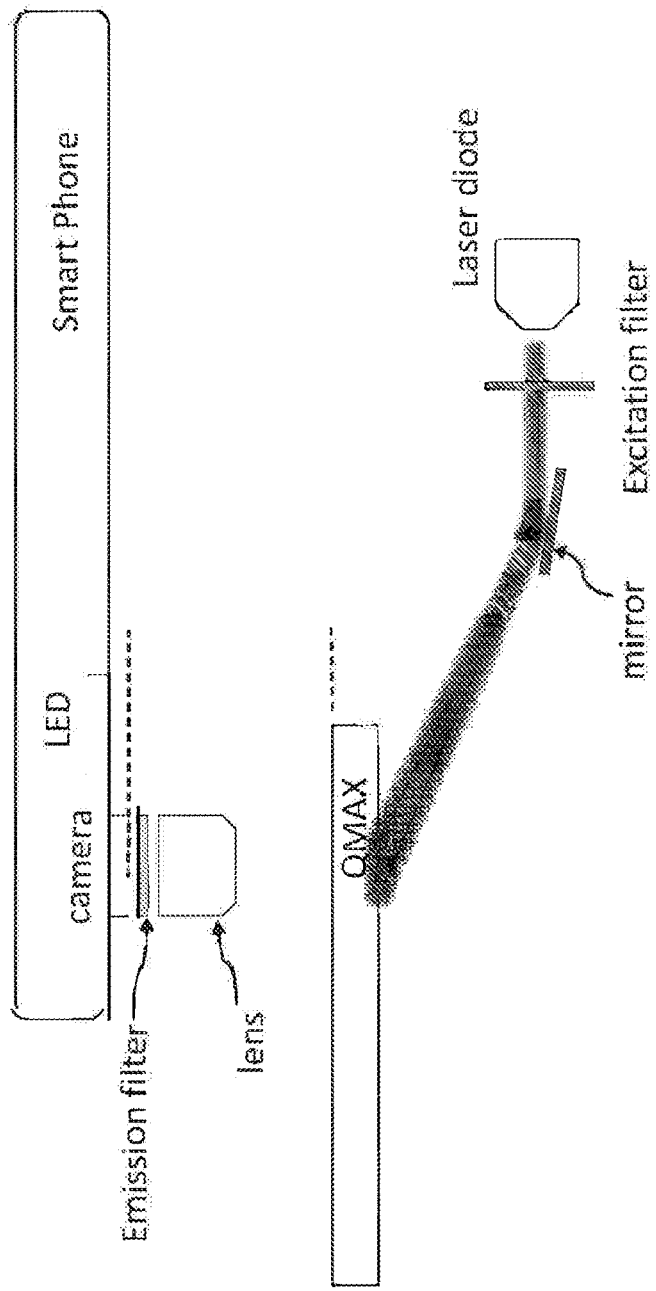
FIG. 11 shows a schematic illustration of the apparatus that is used to capture the images of the sample according to some embodiments of the present invention.

FIG. 11 shows a schematic illustration of the apparatus that is used to capture the images of the sample according to some embodiments of the present invention. With iPhone as an example, FIG. 11 shows the iPhone/reader setup with laser diode as a light source. The laser diode has 638 nm central wavelength with 10 to 20 mW power. The excitation filter before the light source is 650 nm short pass. The light is reflected by an aluminum mirror onto the back of QMAX device with a typical illumination area of 1 mm×4 mm. The observation system is at the front of QMAX device with an iPhone adding an emission filter and lens. The emission filter is 670 nm long pass. The lens has focus distance around 4 mm and N.A. of 0.2.

Figure 12:
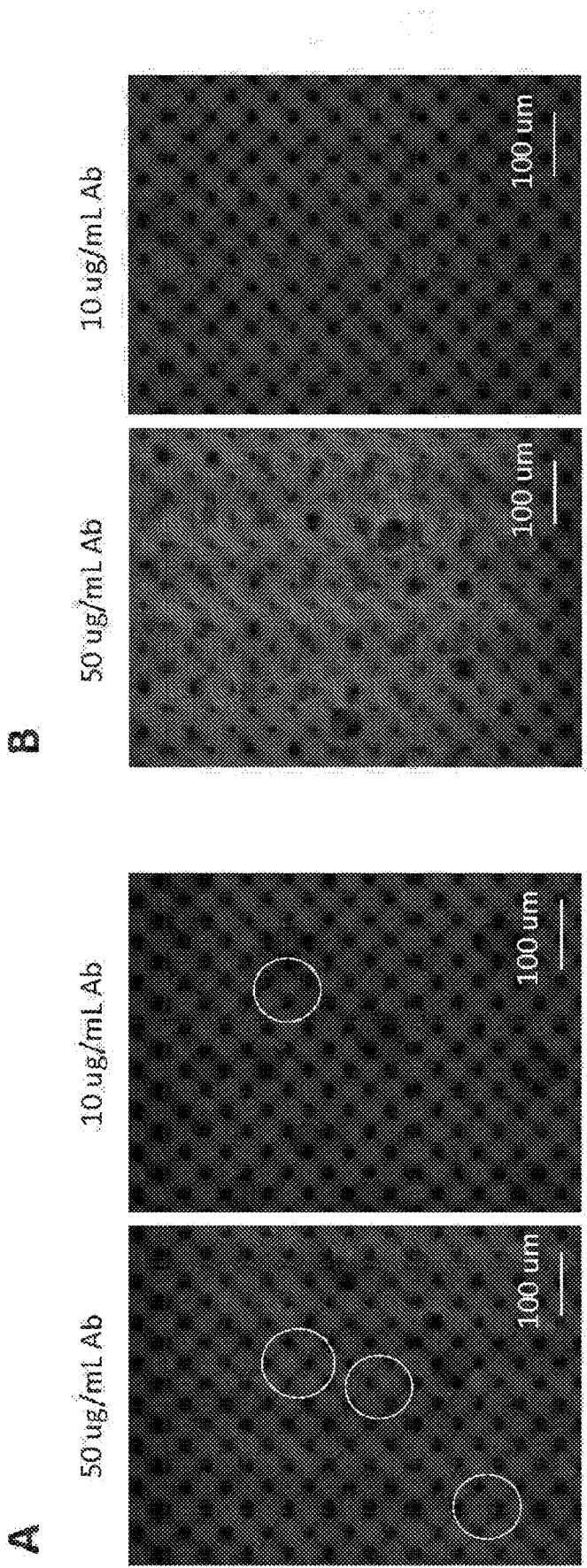
FIG. 12 shows exemplary pictures of CD4 staining with the QMAX device wherein the pictures were captured with the iPhone-laser setup.

FIG. 12 shows exemplary pictures of CD4 staining with the QMAX device wherein the pictures were captured with the iPhone-laser setup shown in FIG. 11. Fluorescence photo of CD-4 stained whole blood in 2 um thick QMAX card under phone/reader system. The left photo is using relative high antibody concentration of 50 μg/ml and right photo is using antibody concentration of 10 μg/ml. The fluorescence photo shows clear fluorescence of stained CD-4 T cells. (b) Fluorescence photo of CD-4 stained whole blood in 10 um thick QMAX card under phone/reader system. The left photo is using relative high antibody concentration of 50 μg/,L and right photo is using antibody concentration of 10 μg/ml. CD-4 T cells is not observed under 10 um QMAX, which might due to the iPhone reader's lower sensitivity and dynamic range compared with inverted microscopy system.

The number of CD4 expressing T cells counted with the QMAX device and the iPhone-laser setup as shown in FIG. 11 are listed in the Table 1 below.

TABLE 1

Back-Calculated CD-4 T Cells Concentration from QMAX/MOST (Mobile Self Test).

|  | QMAX/MOST value | Control Value |
| --- | --- | --- |
| CD4 T Cells | 900/ul | 500-1600 ul |

Figure 13:
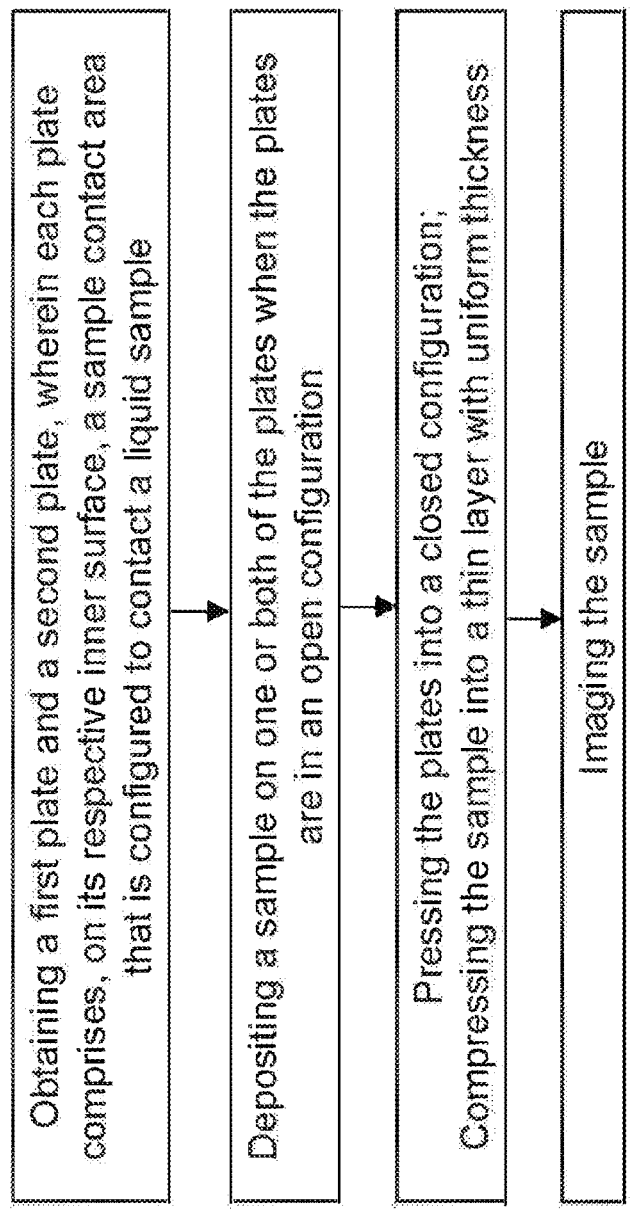
FIG. 13 shows an exemplary flow chart that demonstrates the process to conduct the staining assay for CD4 expressing cells.
Figure 14:
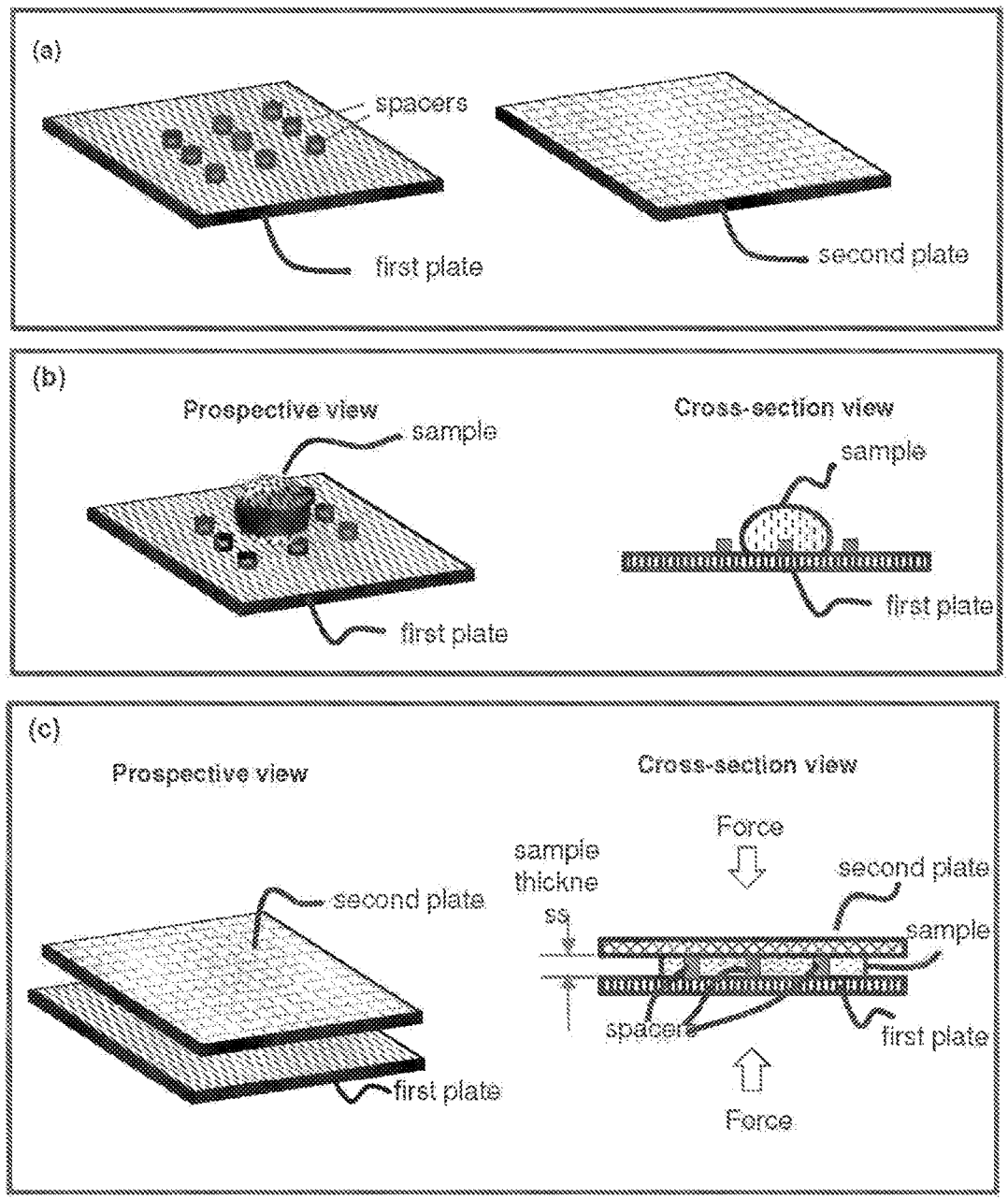
FIG. 14 is an illustration of a CROF (Compressed Regulated Open Flow) embodiment. Panel (a) illustrates a first plate and a second plate wherein the first plate has spacers. Panel (b) illustrates depositing a sample on the first plate (shown), or the second plate (not shown), or both (not shown) at an open configuration. Panel (c) illustrates (i) using the two plates to spread the sample (the sample flow between the plates) and reduce the sample thickness, and (ii) using the spacers and the plate to regulate the sample thickness at the closed configuration. The inner surface of each plate may have one or a plurality of binding sites and or storage sites (not shown).
Figure 15:
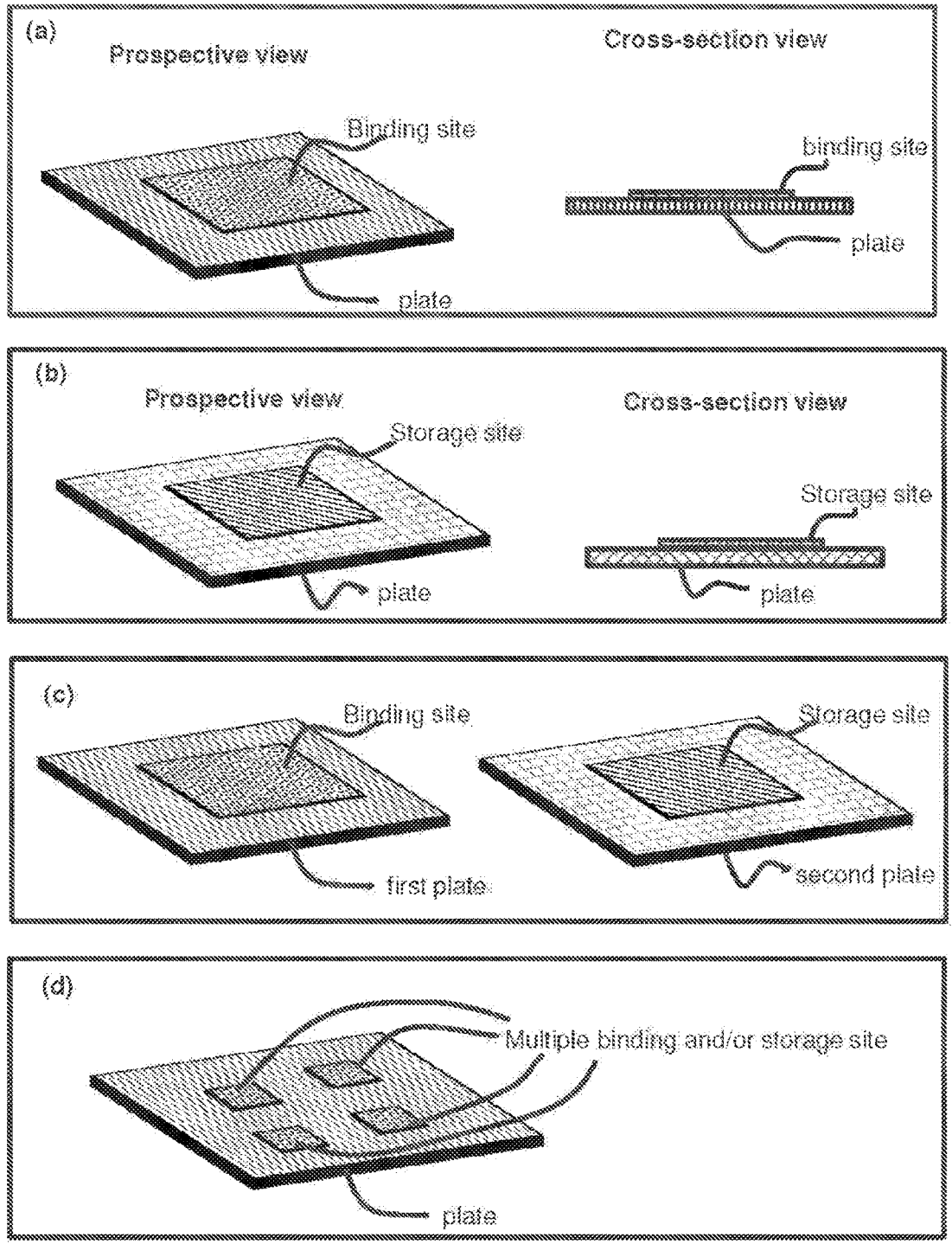
FIG. 15 illustrates plates with a binding site or a storage site. Panel (a) illustrates a plate having a binding site. Panel (b) illustrates a plate having a reagent storage site. Panel (c) illustrates a first plate having a binding site and a second plate having a reagent storage site. Panel (d) illustrates a plate having multiple sites (binding sites and/or storage site).
Figure 16:
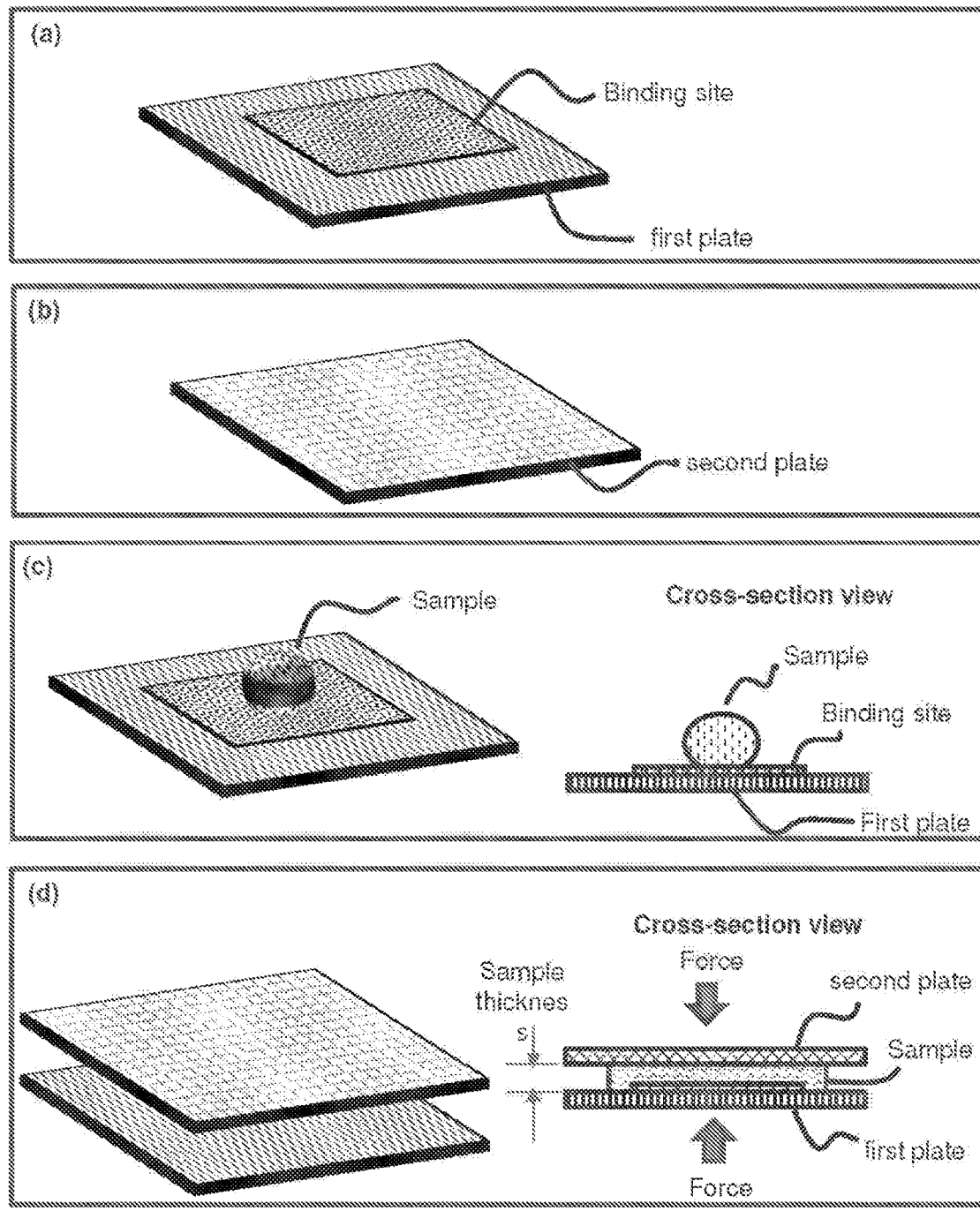
FIG. 16 is a flow-chart and schematic of a method for reducing assay incubation time by reducing sample thickness. Panel (a) illustrates a first plate that has at least one binding site on a substrate surface. Panel (b) illustrates a second plate (which may have a different size from the first plate). Panel (c) illustrates depositing a sample (containing target binding entity) on the substrate surface (shown) or the cover plate (not shown), or both (not shown). Panel (d) illustrates moving the first and second plates so that they are facing each other, and reducing the sample thickness by reducing the spacing of the inner space between the plates. The reduced thickness sample is incubated. The reduced sample thickness speeds up the incubation time. Some embodiment of the method uses spacers to regulate the spacing, which (spacers) are not shown in the illustration.
Figure 17:
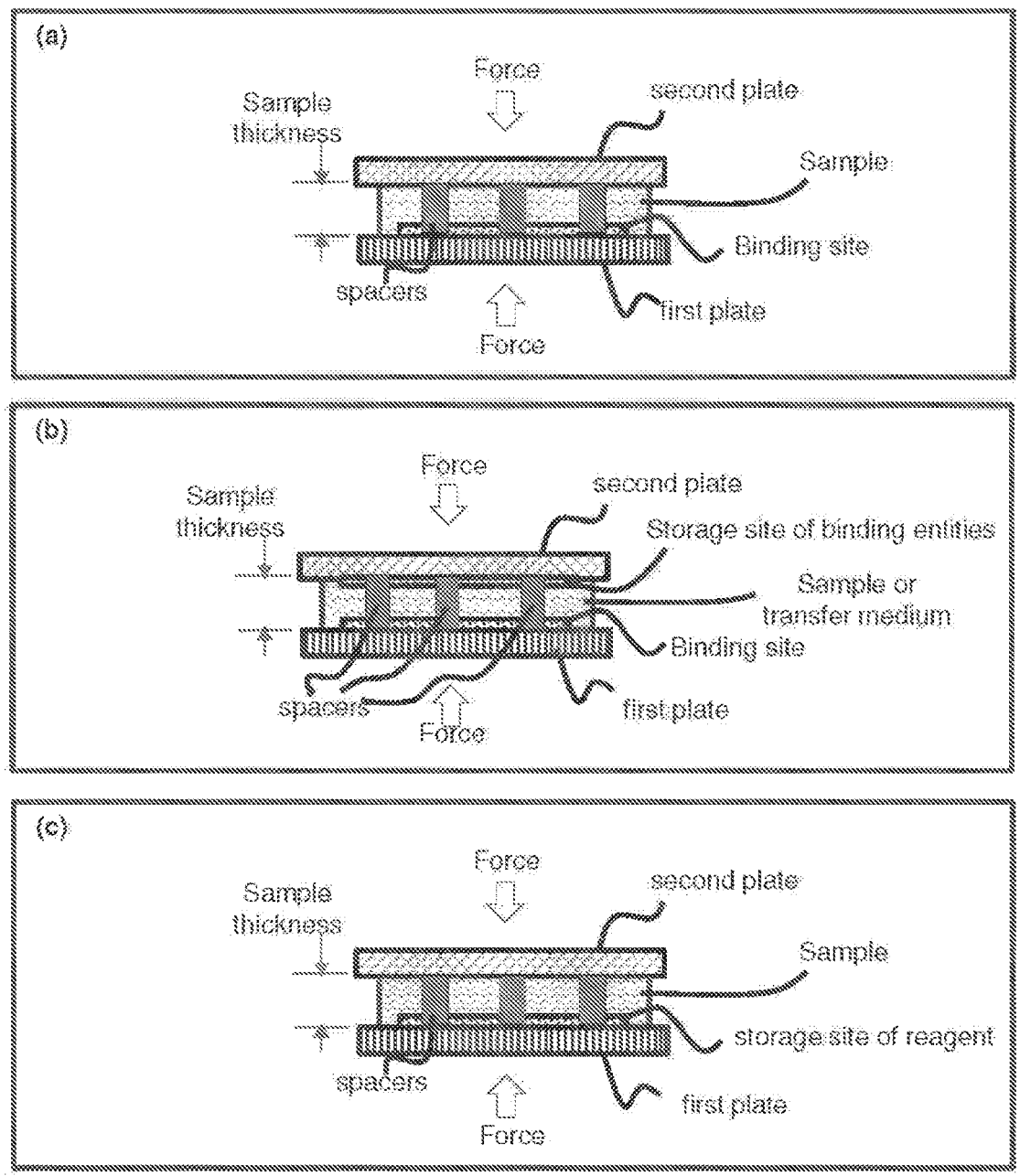
FIG. 17 shows reducing binding or mixing time by reducing the sample thickness using two pates, spacers, and compression (shown in cross-section). Panel (a) illustrates reducing the time for binding entities in a sample to a binding site on a solid surface (X-(Volume to Surface)). Panel (b) illustrates reducing the time for binding entities (e.g. reagent) stored on a surface of plate to a binding site on a surface of another surface (X-(Surface to Surface)). Panel (c) illustrates reducing the time for adding reagents stored on a surface of a plate into a sample that is sandwiched between the plate and other plate (X-(Surface to Volume)).
Figure 18:
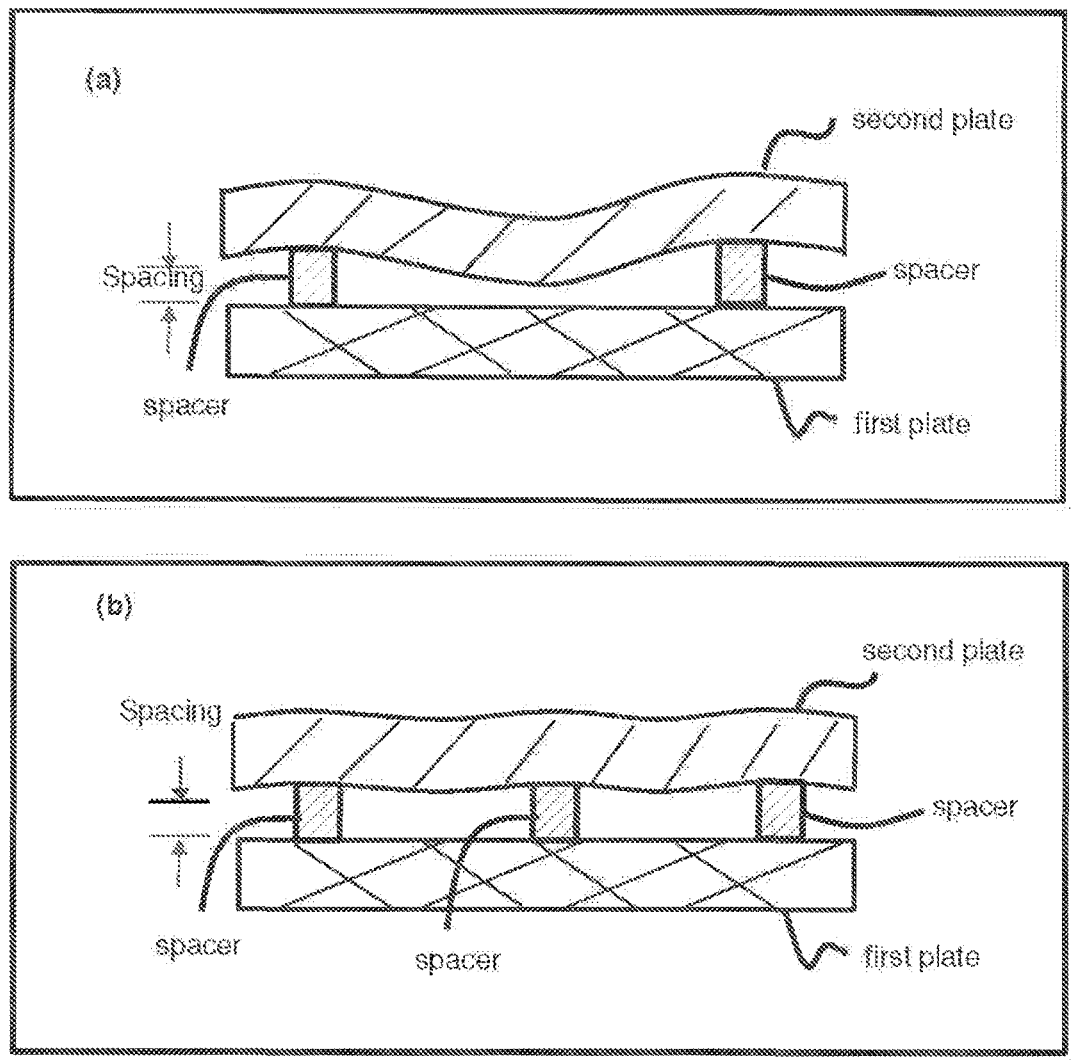
FIG. 18 shows how to avoid or reduce local bending in a flexible plate. Panel (a) illustrates if the inter-spacer distance is too large for a flexible plate (the second plate, e.g. a plastic film) under a given set of sample and compress conditions, the plate has, at the closed configuration, a local sag (i.e. bending inward) between the two neighboring pacers, assuming the first plate is rigid. The sample between the plates is not drawn. Panel (b) illustrates local bending (sag) in a flexible plate in panel (a) is reduced or virtually avoided by using a proper inter-spacer distance and a proper compression force. The sample between the plates is not drawn.
Figure 19:
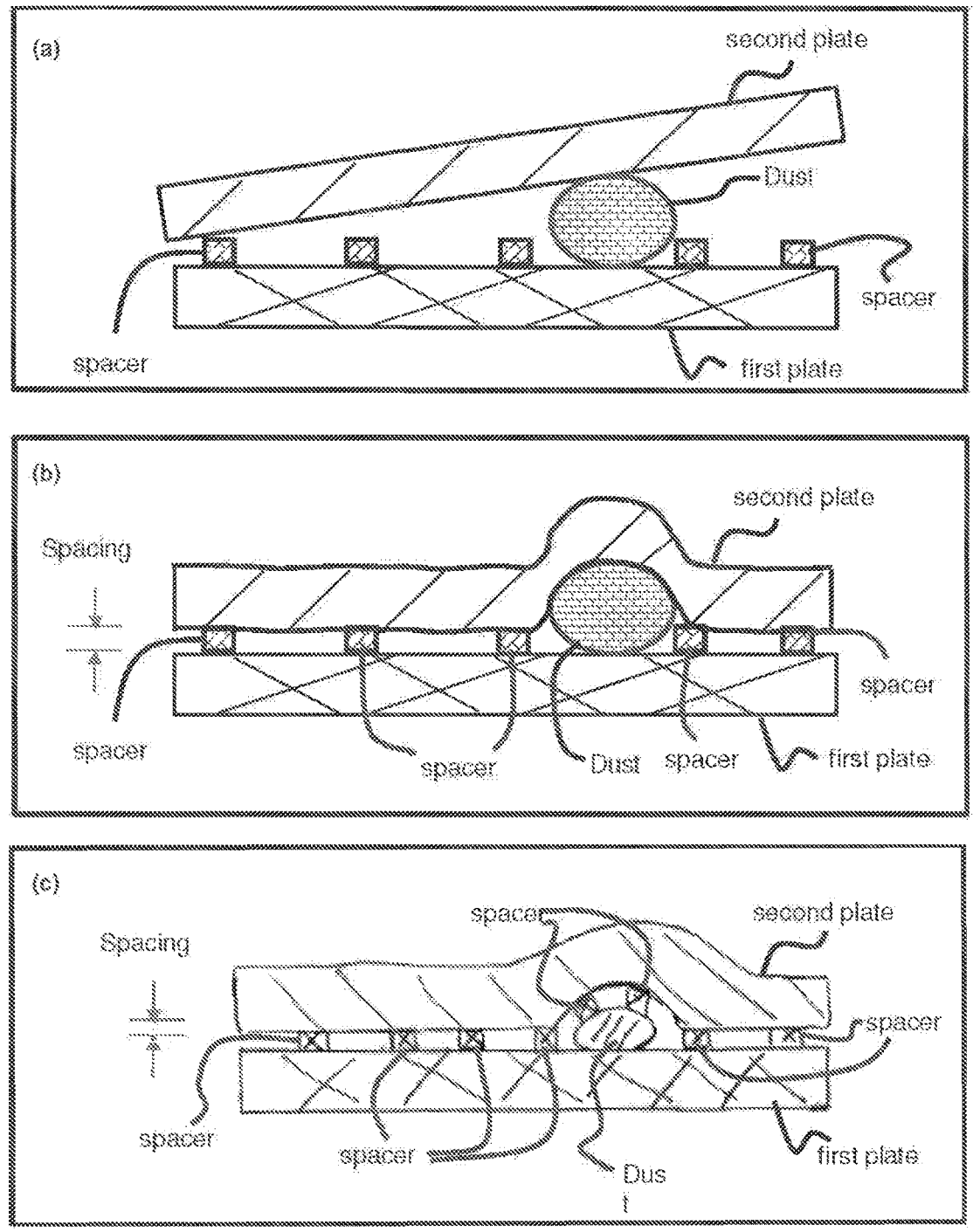
FIG. 19 illustrates reducing effect of large dust on the plate spacing (sample thickness) regulation. Panel (a) illustrates When using two rigid plates, a dust with a thickness larger than a spacer height can destroy an intended plate spacing regulation by the spacers (hence destroy the intended sample thickness regulation). The sample between the plates is not drawn. Panel (b) illustrates using a proper flexible plate and a proper inter-spacer distance, the effect of a dust is isolated to a small area around dust, while in other areas, the plate spacing (hence the sample thickness) is regulated by the spacers not the dust. This illustration has the first plate is rigid, the second plate is flexible, and the spacers are initially fixed on the first plate. Panel (c) illustrates an illustration of using a proper flexible plate and a proper inter-spacer distance, the effect of a dust is isolated to a small area around dust, while in other areas, the plate spacing (hence the sample thickness) is regulated by the spacers not the dust. This illustration has the first plate is rigid, the second plate is flexible, and the spacers are initially fixed on the second plate.
Figure 20:
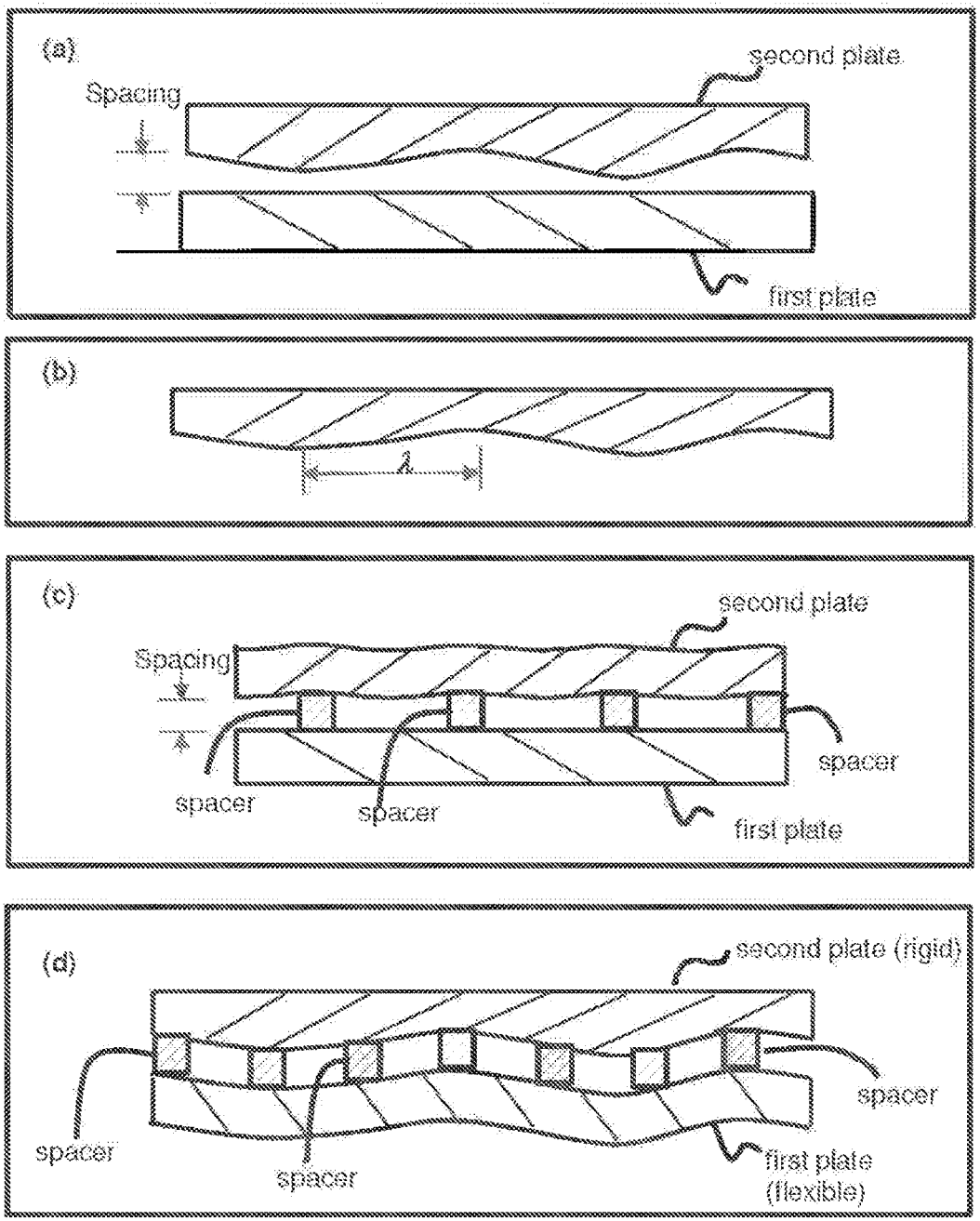
FIG. 20 illustrates reducing effects of surface flatness variation of plate by using proper spacer arrangement and flexible plate(s). Panel (a) shows that surface flatness variation can be significantly large compared with a desired sample thickness, causing errors in determining a sample thickness. In this illustration, only one plate has a large flatness variation (in reality, both plates may have large flatness variation). The sample between the plates is not drawn. Panel (b) illustrates a surface flatness variation distance of a plate, *[][]* is the distance from a local maximum to a neighboring local minimum of a surface height. Panel (c) illustrates how a small surface flatness variation can be achieved by making one or both plate flexible and using a proper inter-spacer distance and proper compressing force to correct, at the closed configuration, the original surface flatness variation of the plate when they are at open configuration. The sample between the plates is not drawn. Panel (d) illustrates making the sample thickness variation less than the initial surface flatness variation of the plate by using a flexible second plate and a proper inter spacer distance. The flexible plate follows the contour of the rigid plate. The sample between the plates is not drawn.
Figure 21:
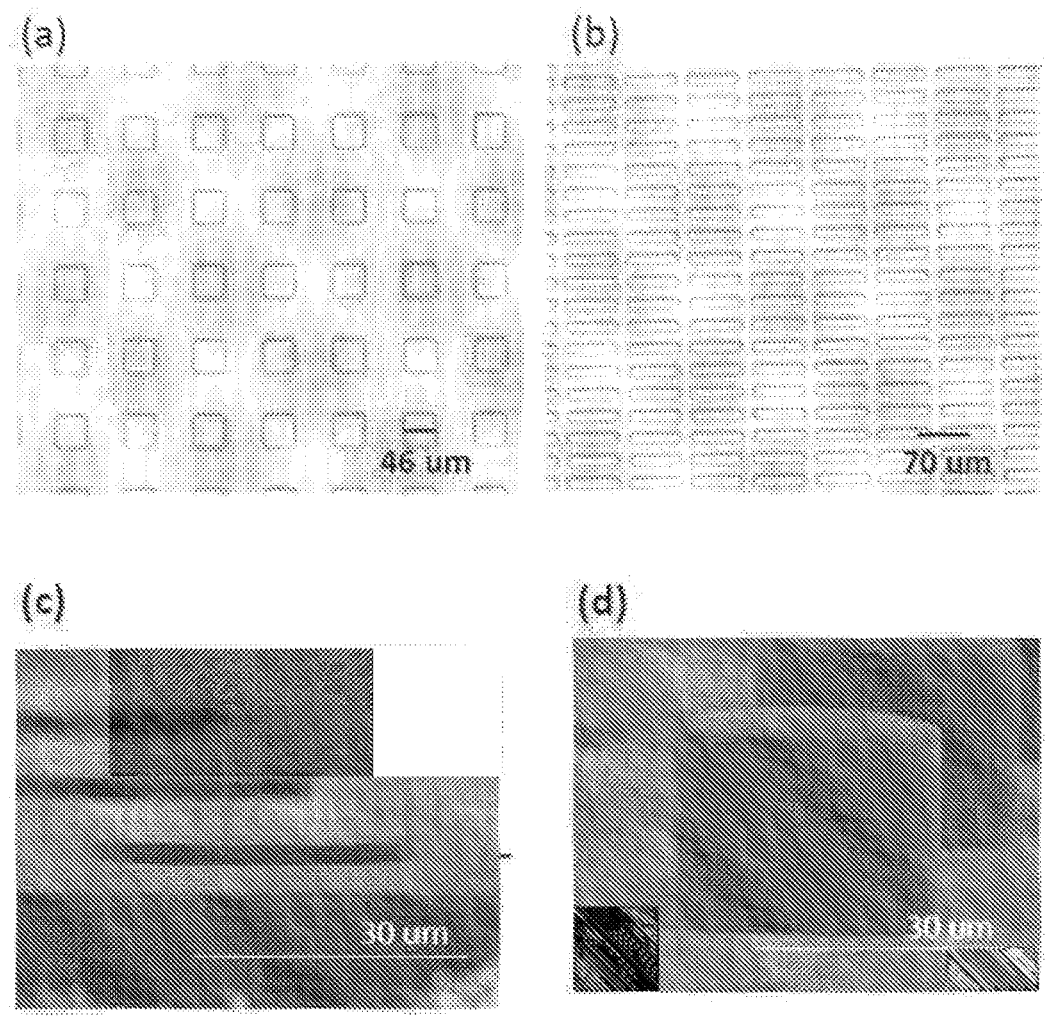
FIG. 21 Spacers on a plate. Top view of photograph of (a) 46 um×46 um pillar spacer size and 54 um inter pillar distance, and (b) 10 um×70 um pillar spacer size and 10 um pillar distance; and prospect view SEM of (c) 30 um×40 um pillar spacer size of 2 um spacer height, and (d) 30 um×40 um pillar spacer size of 30 um spacer height.

FIG. 13 shows an exemplary flow chart that demonstrates the process to conduct the staining assay for CD4 expressing cells.

In some embodiments, the staining comprises the following steps:

(a) obtaining a first plate and a second plate, wherein each plate comprises, on its respective inner surface, a sample contact area that is configured to contact a liquid sample, wherein a detecting agent is positioned on the sample contact area of one or both of the plates, and wherein the detecting agent is configured to specifically bind to the biomarker, (b) depositing the sample in the sample contact area, wherein the sample comprises cells that express the biomarker;

(c) pressing the first plate and the second plate to compress the sample into a thin layer, which is at least partly confined by the two sample contact areas that face each other;

(d) incubating for a predetermined period of time that is about 60 seconds or less; and (e) quantifying the cells expressing the biomarker by imaging the sample layer and counting the cells expressing the biomarker.

Examples of Present Invention

One Step Staining Assay for CD4 T Cells in Whole Blood

BA1.1 A method for quantifying cells that express a biomarker in a sample, comprising:

(a) obtaining a sample holder that is configured to hold a liquid sample that contains an analyte, wherein a detecting agent is positioned in the sample holder and is configured to specifically bind to the biomarker;

(b) depositing the sample in the sample contact area, wherein the sample comprises cells that express the biomarker; and the sample is in contact with the detecting agent in the sample holder;

(c) adjusting the sample holder to compress the sample into a thin layer, (d) incubating for a predetermined period of time; and (e) quantifying the cells expressing the biomarker by imaging the sample layer and counting the cells expressing the biomarker.

BA1.2 A method for quantifying cells that express a biomarker in a sample, comprising:

(a) obtaining a first plate and a second plate, wherein each plate comprises, on its respective inner surface, a sample contact area that is configured to contact a liquid sample, wherein a detecting agent is positioned on the sample contact area of one or both of the plates, and wherein the detecting agent is configured to specifically bind to the biomarker, (b) depositing the sample in the sample contact area, wherein the sample comprises cells that express the biomarker;

(c) pressing the first plate and the second plate to compress the sample into a thin layer, which is at least partly confined by the two sample contact areas that face each other;

(d) incubating for a predetermined period of time that is about 60 seconds or less; and (e) quantifying the cells expressing the biomarker by imaging the sample layer and counting the cells expressing the biomarker.

BA1.3 A method for quantifying cells that express CD4 (cluster of differentiation 4) in a blood sample, comprising:

(a) obtaining a first plate and a second plate, wherein each plate comprises, on its respective inner surface, a sample contact area that is configured to contact a blood sample, wherein a detecting agent is positioned on the sample contact area of one or both of the plates, and wherein the detecting agent is configured to specifically bind to CD4, (b) depositing the blood sample in the sample contact area, wherein the blood sample comprises cells that express CD4;

(c) pressing the first plate and the second plate to compress the blood sample into a thin layer, which is at least partly confined by the two sample contact areas that face each other;

(d) incubating for a predetermined period of time that is about 60 seconds or less; and (e) quantifying the CD4 expressing cells by imaging the sample layer and counting the cells expressing CD4.

BA2.1 An apparatus for quantifying cells that express a biomarker in a sample, comprising:

a sample holder that is configured to hold a liquid sample that contains cells that express a biomarker, wherein a detecting agent is positioned in the sample holder and is configured to specifically bind to the biomarker; and an adaptor that is configured to accommodate the sample holder and be attachable to a mobile device, wherein:

i. the mobile device comprises an imager, ii. the mobile device comprises an imager, the adaptor is configured to position the sample in a field of view (FOV) of the imager when the adaptor is attached to the mobile device, and iii. the imager is configured to capture images of the sample, thereby detecting/measuring a signal that is generated by the binding of the biomarker with the detecting agent after the sample is incubated with the detecting agent for a predetermined period of time that is about 60 seconds or less.

BB1.1 The method or apparatus of any prior embodiments, wherein the predetermined period of time that is about 30 seconds or less.

BB1.2 The method or apparatus of any prior embodiments, with the proviso that the sample contact areas are not washed after step (d).

BB1.3 The method or apparatus of any prior embodiments, wherein the detecting agent is an antibody.

BB1.4.1 The method or apparatus of any prior embodiments, wherein the antibody is labeled with a fluorophore.

BB1.5 The method or apparatus of any prior embodiments, wherein the detecting agent is labeled with signaling molecule that emits a signal upon excitation.

BB1.6 The method or apparatus of any prior embodiments, wherein the thin layer has a uniform thickness that is about equal to or less than 10 um.

BB1.7 The method or apparatus of any prior embodiments, wherein the thin layer has a uniform thickness that is about equal to or less than 2 um.

BB1.8 The method or apparatus of any prior embodiments, wherein the sample is whole blood.

BB1.9 The method or apparatus of any prior embodiments, wherein the biomarker is CD4 (cluster of differentiation 4).

BB1.10 The method or apparatus of any prior embodiments, wherein the cells are T cells.

BB1.11 The method or apparatus of any prior embodiments, wherein the detecting agent is immobilized on the sample contact area.

Device and Assay with High Uniformity

Flat Top of Pillar Spacers

In certain embodiments of the present invention, the spacers are pillars that have a flat top and a foot fixed on one plate, wherein the flat top has a smoothness with a small surface variation, and the variation is less than 5, 10 nm, 20 nm, 30 nm, 50 nm, 100 nm, 200 nm, 300 nm, 400 nm, 500 nm, 600 nm, 700 nm, 800 nm, 1000 nm, or in a range between any two of the values. A preferred flat pillar top smoothness is that surface variation of 50 nm or less.

Furthermore, the surface variation is relative to the spacer height and the ratio of the pillar flat top surface variation to the spacer height is less than 0.5%, 1%, 3%, 5%, 7%, 10%, 15%, 20%, 30%, 40%, or in a range between any two of the values. A preferred flat pillar top smoothness has a ratio of the pillar flat top surface variation to the spacer height is less than 2%, 5%, or 10%.

Sidewall Angle of Pillar Spacers

In certain embodiments of the present invention, the spacers are pillars that have a sidewall angle. In some embodiments, the sidewall angle is less than 5 degree (measured from the normal of a surface), 10 degree, 20 degree, 30 degree, 40 degree, 50 degree, 70 degree, or in a range between any two of the values. In a preferred embodiment, the sidewall angle is less 5 degree, 10 degree, or 20 degree.

Formation of Uniform Thin Fluidic Layer by an Imprecise Force Pressing

In certain embodiment of the present invention, a uniform thin fluidic sample layer is formed by using a pressing with an imprecise force. The term "imprecise pressing force" without adding the details and then adding a definition for imprecise pressing force. As used herein, the term "imprecise" in the context of a force (e.g. "imprecise pressing force") refers to a force that (a) has a magnitude that is not precisely known or precisely predictable at the time the force is applied; (b) has a pressure in the range of 0.01 kg/cm² (centimeter square) to 100 kg/cm². (c) varies in magnitude from one application of the force to the next; and (d) the imprecision (i.e. the variation) of the force in (a) and (c) is at least 20% of the total force that actually is applied.

An imprecise force can be applied by human hand, for example, e.g., by pinching an object together between a thumb and index finger, or by pinching and rubbing an object together between a thumb and index finger.

In some embodiments, the imprecise force by the hand pressing has a pressure of 0.01 kg/cm2, 0.1 kg/cm2, 0.5 kg/cm2, 1 kg/cm2, 2 kg/cm2, kg/cm2, 5 kg/cm2, 10 kg/cm2, 20 kg/cm2, 30 kg/cm2, 40 kg/cm2, 50 kg/cm2, 60 kg/cm2, 100 kg/cm2, 150 kg/cm2, 200 kg/cm2, or a range between any two of the values; and a preferred range of 0.1 kg/cm2 to 0.5 kg/cm2, 0.5 kg/cm2 to 1 kg/cm2, 1 kg/cm2 to 5 kg/cm2, 5 kg/cm2 to 10 kg/cm2 (Pressure).

Spacer Filling Factor.

The term "spacer filling factor" or "filling factor" refers to the ratio of the spacer contact area to the total plate area", wherein the spacer contact area refers, at a closed configuration, the contact area that the spacer's top surface contacts to the inner surface of a plate, and the total plate area refers the total area of the inner surface of the plate that the flat top of the spacers contact. Since there are two plates and each spacer has two contact surfaces each contacting one plate, the filling fact is the filling factor of the smallest. For example, if the spacers are pillars with a flat top of a square shape (10 um×10 um), a nearly uniform cross-section and 2 um tall, and the spacers are periodic with a period of 100 um, then the filling factor of the spacer is 1%. If in the above example, the foot of the pillar spacer is a square shape of 15 um×15 um, then the filling factor is still 1% by the definition.

AA1. A device for forming a thin fluidic sample layer with a uniform predetermined thickness by pressing, comprising:
a first plate, a second plate, and spacers, wherein: the plates are movable relative to each other into different configurations; one or both plates are flexible;
each of the plates comprises an inner surface that has a sample contact area for contacting a fluidic sample;
each of the plates comprises, on its respective outer surface, a force area for applying an pressing force that forces the plates together;
one or both of the plates comprise the spacers that are permanently fixed on the inner surface of a respective plate;
the spacers have a predetermined substantially uniform height that is equal to or less than 200 microns, and a predetermined fixed inter-spacer-distance;
the fourth power of the inter-spacer-distance (ISD) divided by the thickness (h) and the Young's modulus (E) of the flexible plate (ISO4/(hE)) is 5×106 um3/GPa or less; and at least one of the spacers is inside the sample contact area;
wherein one of the configurations is an open configuration, in which: the two plates are partially or completely separated apart, the spacing between the plates is not regulated by the spacers, and the sample is deposited on one or both of the plates;
wherein another of the configurations is a closed configuration which is configured after the sample is deposited in the open configuration and the plates are forced to the close configuration by applying the pressing force on the force area; and in the closed configuration: at least part of the sample is compressed by the two plates into a layer of highly uniform thickness and is substantially stagnant relative to the plates, wherein the uniform thickness of the layer is confined by the sample contact areas of the two plates and is regulated by the plates and the spacers.

AA2. A method of forming a thin fluidic sample layer with a uniform predetermined thickness by pressing, comprising the steps of:
(a) obtaining a device of embodiment AA1;
(b) depositing a fluidic sample on one or both of the plates; when the plates are configured in an open configuration, wherein the open configuration is a configuration in which the two plates are partially or completely separated apart and the spacing between the plates is not regulated by the spacers;
(c) after (b), forcing the two plates into a closed configuration, in which: at least part of the sample is compressed by the two plates into a layer of substantially uniform thickness, wherein the uniform thickness of the layer is confined by the sample contact surfaces of the plates and is regulated by the plates and the spacers.

AA3. A device for analyzing a fluidic sample, comprising: a first plate, a second plate, and spacers, wherein:
i. the plates are movable relative to each other into different configurations;
ii. one or both plates are flexible;
iii. each of the plates has, on its respective inner surface, a sample contact area for contacting a fluidic sample,
iv. one or both of the plates comprise the spacers and the spacers are fixed on the inner surface of a respective plate;
v. the spacers have a predetermined substantially uniform height thatis equal to or less than 200 microns, and the inter-spacer-distance is predetermined;
vi. the Young's modulus of the spacers multiplied by the filling factor of the spacers is at least 2 MPa; and
vii. at least one of the spacers is inside the sample contact area; and
wherein one of the configurations is an open configuration, in which: the two plates are partially or completely separated apart, the spacing between the plates is not regulated by the spacers, and the sample is deposited on one or both of the plates; and wherein another of the configurations is a closed configuration which is configured after the sample is deposited in the open configuration; and in the closed configuration: at least part of the sample is compressed by the two plates into a layer of highly uniform thickness, wherein the uniform thickness of the layer is confined by the sample contact surfaces of the plates and is regulated by the plates and the spacers.

AA4. A method of forming a thin fluidic sample layer with a uniform predetermined thickness by pressing, comprising the steps of:
(a) obtaining a device of embodiment AA3;
(b) depositing a fluidic sample on one or both of the plates; when the plates are configured in an open configuration, wherein the open configuration is a configuration in which the two plates are partially or completely separated apart and the spacing between the plates is not regulated by the spacers; and
(c) after (b), forcing the two plates into a closed configuration, in which: at least part of the sample is compressed by the two plates into a layer of substantially uniform thickness, wherein the uniform thickness of the layer is confined by the sample contact surfaces of the plates and is regulated by the plates and the spacers.

AA5. A device for analyzing a fluidic sample, comprising: a first plate and a second plate, wherein:
i. the plates are movable relative to each other into different configurations;
ii. one or both plates are flexible;
iii. each of the plates has, on its respective surface, a sample contact area for contacting a sample that contains an analyte,
iv. one or both of the plates comprise spacers that are permanently fixed to a plate within a sample contact area, wherein the spacers have a predetermined substantially uniform height and a predetermined fixed inter-spacer distance that is at least about 2 times larger than the size of the analyte, up to 200 um, and wherein at least one of the spacers is inside the sample contact area;
wherein one of the configurations is an open configuration, in which: the two plates are separated apart, the spacing between the plates is not regulated by the spacers, and the sample is deposited on one or both of the plates; and wherein another of the configurations is a closed configuration which is configured after the sample deposition in the open configuration; and in the closed configuration: at least part of the sample is compressed by the two plates into a layer of highly uniform thickness, wherein the uniform thickness of the layer is confined by the sample contact surfaces of the plates and is regulated by the plates and the spacers.

AA6. A method of forming a thin fluidic sample layer with a uniform predetermined thickness by pressing, comprising the steps of:
(a) obtaining a device of embodiment AA5;
(b) depositing a fluidic sample on one or both of the plates; when the plates are configured in an open configuration, wherein the open configuration is a configuration in which the two plates are partially or completely separated apart and the spacing between the plates is not regulated by the spacers;

(c) after (b), forcing the two plates into a closed configuration, in which: at least part of the sample is compressed by the two plates into a layer of substantially uniform thickness, wherein the uniform thickness of the layer is confined by the sample contact surfaces of the plates and is regulated by the plates and the spacers.

AA7. A device for forming a thin fluidic sample layer with a uniform predetermined thickness by pressing, comprising:
a first plate, a second plate, and spacers, wherein:
the plates are movable relative to each other into different configurations;
one or both plates are flexible;
each of the plates comprises, on its respective inner surface, a sample contact area for contacting and/or compressing a fluidic sample;
each of the plates comprises, on its respective outer surface, an area for applying a force that forces the plates together;
one or both of the plates comprise the spacers that are permanently fixed on the inner surface of a respective plate;
the spacers have a predetermined substantially uniform height that is equal to or less than 200 microns, a predetermined width, and a predetermined fixed inter-spacer-distance;
a ratio of the inter-spacer-distance to the spacer width is 1.5 or larger; and
at least one of the spacers is inside the sample contact area;
wherein one of the configurations is an open configuration, in which: the two plates are partially or completely separated apart, the spacing between the plates is not regulated by the spacers, and the sample is deposited on one or both of the plates;
wherein another of the configurations is a closed configuration which is configured after the sample deposition in the open configuration; and in the closed configuration: at least part of the sample is compressed by the two plates into a layer of highly uniform thickness and is substantially stagnant relative to the plates, wherein the uniform thickness of the layer is confined by the sample contact areas of the two plates and is regulated by the plates and the spacers.

AA8. A method of forming a thin fluidic sample layer with a uniform predetermined thickness by pressing with an imprecise pressing force, comprising the steps of:
(a) obtaining a device of embodiment AA7;
(b) obtaining a fluidic sample;
(c) depositing the sample on one or both of the plates; when the plates are configured in an open configuration, wherein the open configuration is a configuration in which the two plates are partially or completely separated apart and the spacing between the plates is not regulated by the spacers; and
(d) after (c), forcing the two plates into a closed configuration, in which: at least part of the sample is compressed by the two plates into a layer of substantially uniform thickness, wherein the uniform thickness of the layer is confined by the sample contact surfaces of the plates and is regulated by the plates and the spacers.

The devices or methods of any prior embodiment, wherein the spacers have a shape of pillar with a foot fixed on one of the plate and a flat top surface for contacting the other plate.

The devices or methods of any prior embodiment, wherein the spacers have a shape of pillar with a foot fixed on one of the plate, a flat top surface for contacting the other plate, substantially uniform cross-section.

The devices or methods of any prior embodiment, wherein the spacers have a shape of pillar with a foot fixed on one of the plate and a flat top surface for contacting the other plate, wherein the flat top surface of the pillars has a variation in less than 10 nm.

The devices or methods of any prior embodiment, wherein the spacers have a shape of pillar with a foot fixed on one of the plate and a flat top surface for contacting the other plate, wherein the flat top surface of the pillars has a variation in less than 50 nm.

The devices or methods of any prior embodiment, wherein the spacers have a shape of pillar with a foot fixed on one of the plate and a flat top surface for contacting the other plate, wherein the flat top surface of the pillars has a variation in less than 50 nm.

The devices or methods of any prior embodiment, wherein the spacers have a shape of pillar with a foot fixed on one of the plate and a flat top surface for contacting the other plate, wherein the flat top surface of the pillars has a variation in less than 10 nm, 20 nm, 30 nm, 100 nm, 200 nm, or in a range of any two of the values.

The devices or methods of any prior embodiment, wherein the Young's modulus of the spacers multiplied by the filling factor of the spacers is at least 2 MPa.

The devices or methods of any prior embodiment, wherein the sample comprises an analyte and the predetermined constant inter-spacer distance is at least about 2 times larger than the size of the analyte, up to 200 um.

The devices or methods of any prior embodiment, wherein the sample comprise an analyte, the predetermined constant inter-spacer distance is at least about 2 times larger than the size of the analyte, up to 200 um, and the Young's modulus of the spacers multiplied by the filling factor of the spacers is at least 2 MPa.

The devices or methods of any prior embodiment, wherein a fourth power of the inter-spacer-distance (IDS) divided by the thickness (h) and the Young's modulus (E) of the flexible plate (ISDA4/(hE)) is $5 \times 10^6$ umA3/GPa or less.

The devices or methods of any prior embodiment, wherein a fourth power of the inter-spacer-distance (IDS) divided by the thickness (h) and the Young's modulus (E) of the flexible plate (ISDA4/(hE)) is $1 \times 10^6$ umA3/GPa or less.

The devices or methods of any prior embodiment, wherein a fourth power of the inter-spacer-distance (IDS) divided by the thickness (h) and the Young's modulus (E) of the flexible plate (ISDA4/(hE)) is $5 \times 10^5$ umA3/GPa or less.

The devices or methods of any prior embodiment, wherein the Young's modulus of the spacers multiplied by the filling factor of the spacers is at least 2 MPa, and a fourth power of the inter-spacer-distance (IDS) divided by the thickness (h) and the Young's modulus (E) of the flexible plate (ISDA4/(hE)) is $1 \times 10^5$ umA3/GPa or less.

The devices or methods of any prior embodiment, wherein the Young's modulus of the spacers multiplied by the filling factor of the spacers is at least 2 MPa, and a fourth power of the inter-spacer-distance (IDS) divided by the thickness (h) and the Young's modulus (E) of the flexible plate (ISDA4/(hE)) is $1 \times 10^{A4}$ umA3/GPa or less.

The devices or methods of any prior embodiment, wherein the Young's modulus of the spacers multiplied by the filling factor of the spacers is at least 20 MPa.

The devices or methods of any prior embodiment, wherein the ratio of the inter-spacing distance of the spacers to the average width of the spacer is 2 or larger.

The devices or methods of any prior embodiment, wherein the ratio of the inter-spacing distance of the spacers to the average width of the spacer is 2 or larger, and the Young's modulus of the spacers multiplied by the filling factor of the spacers is at least 2 MPa.

The devices or methods of any prior embodiment, wherein inter-spacer distance that is at least about 2 times larger than the size of the analyte, up to 200 um.

The devices or methods of any prior embodiment, wherein a ratio of the inter-spacer-distance to the spacer width is 1.5 or larger.

The devices or methods of any prior embodiment, wherein a ratio of the width to the height of the spacer is 1 or larger.

The devices or methods of any prior embodiment, wherein a ratio of the width to the height of the spacer is 1.5 or larger.

The devices or methods of any prior embodiment, wherein a ratio of the width to the height of the spacer is 2 or larger.

The devices or methods of any prior embodiment, wherein a ratio of the width to the height of the spacer is larger than 2, 3, 5, 10, 20, 30, 50, or in a range of any two the value.

The methods of any prior embodiment, wherein the force that presses the two plates into the closed configuration is an imprecise pressing force.

The methods of any prior embodiment, wherein the force that presses the two plates into the closed configuration is an imprecise pressing force provided by human hand.

The methods of any prior embodiment, wherein the forcing of the two plates to compress at least part of the sample into a layer of substantially uniform thickness comprises a use ofa conformable pressing, either in parallel or sequentially, an area of at least one of the plates to press the plates together to a closed configuration, wherein the conformable pressing generates a substantially uniform pressure on the plates over the at least part of the sample, and the pressing spreads the at least part of the sample laterally between the sample contact surfaces of the plates, and wherein the closed configuration is a configuration in which the spacing between the plates in the layer of uniform thickness region is regulated by the spacers; and wherein the reduced thickness of the sample reduces the time for mixing the reagents on the storage site with the sample.

The methods of any prior embodiment, wherein the pressing force is an imprecise force that has a magnitude which is, at the time that the force is applied, either (a) unknown and unpredictable, or (b) cannot be known and cannot be predicted within an accuracy equal or better than 20% of the average pressing force applied.

The methods of any prior embodiment, wherein the pressing force is an imprecise force that has a magnitude which is, at the time that the force is applied, either (a) unknown and unpredictable, or (b) cannot be known and cannot be predicted within an accuracy equal or better than 30% of the average pressing force applied.

The methods of any prior embodiment, wherein the pressing force is an imprecise force that has a magnitude which is, at the time that the force is applied, either (a) unknown and unpredictable, or (b) cannot be known and cannot be predicted within an accuracy equal or better than 30% of the average pressing force applied; and wherein the layer of highly uniform thickness has a variation in thickness uniform of 20% or less.

The methods of any prior embodiment, wherein the pressing force is an imprecise force that has a magnitude which cannot, at the time that the force is applied, be determined within an accuracy equal or better than 30%, 40%, 50%, 70%, 100%, 200%, 300%, 500%, 1000%, 2000%, or in a range between any of the two values.

The devices or methods of any prior embodiment, wherein the flexible plate has a thickness of in the range of 10 μm to 200 um.

The devices or methods of any prior embodiment, wherein the flexible plate has a thickness of in the range of 20 μm to 100 um.

The devices or methods of any prior embodiment, wherein the flexible plate has a thickness of in the range of 25 um to 180 um.

The devices or methods of any prior embodiment, wherein the flexible plate has a thickness of in the range of 200 μm to 260 um.

The devices or methods of any prior embodiment, wherein the flexible plate has a thickness of equal to or less than 250 um, 225 um, 200 um, 175 um, 150 um, 125 um, 100 um, 75 um, 50 um, 25 um, 10 μm, 5 um, 1 um, or in a range between the two of the values.

The devices or methods of any prior method, wherein the sample has a viscosity in the range of 0.1 to 4 (mPa s).

The devices or methods of any prior embodiment, wherein the flexible plate has a thickness of in the range of 200 μm to 260 um.

The devices or methods of any prior embodiment, wherein the flexible plate has a thickness in the range of 20 μm to 200 μm and Young's modulus in the range 0.1 to 5 GPa.

1. The method of any prior claim, wherein the sample deposition of step (b) is a deposition directly from a subject to the plate without using any transferring devices.

2. The method any prior claim, wherein during the deposition of step (b), the amount of the sample deposited on the plate is unknown.

3. The method of any prior claim, wherein the method further comprises an analyzing step that analyzes the sample.

4. The method of any prior embodiment, wherein the analyzing step (e) comprises calculating the volume of a relevant sample volume by measuring the lateral area of the relevant sample volume and calculating the volume from the lateral area and the predetermined spacer height.

5. The method of any prior embodiment, wherein the analyzing step (e) comprises measuring: imaging luminescence selected from photoluminescence, electroluminescence, and electrochemiluminescence, surface Raman scattering, electrical impedance selected from resistance, capacitance, and inductance, or any combination thereof.

6. The method of any prior claim, wherein the analyzing step (e) comprises reading, image analysis, or counting of the analyte, or a combination of thereof.

7. The method of any prior claim, wherein the sample contains one or plurality of analytes, and one or both plate sample contact surfaces comprise one or a plurality of binding sites that each binds and immobilize a respective analyte.

8. The method of any prior claim, wherein one or both plate sample contact surfaces comprise one or a plurality of storage sites that each stores a reagent or reagents, wherein the reagent(s) dissolve and diffuse in the sample during or after step (c).

9. The method of any prior claim, wherein one or both plate sample contact surfaces comprise one or a plurality of amplification sites that are each capable of amplifying a signal from the analyte or a label of the analyte when the analyte or label is within 500 nm from an amplification site.

10. The method of any prior claim, wherein:
  i. one or both plate sample contact surfaces comprise one or a plurality of binding sites that each binds and immobilize a respective analyte; or
  ii. one or both plate sample contact surfaces comprise, one or a plurality of storage sites that each stores a reagent or reagents; wherein the reagent(s) dissolve and diffuse in the sample during or after step (c), and wherein the sample contains one or plurality of analytes; or
  iii. one or a plurality of amplification sites that are each capable of amplifying a signal from the analyte or a label of the analyte when the analyte or label is 500 nm from the amplification site; or
  iv. any combination of i to iii.

11. The devices or methods of any prior embodiment, wherein the liquid sample is a biological sample selected from amniotic fluid, aqueous humour, vitreous humour, blood (e.g., whole blood, fractionated blood, plasma or serum), breast milk, cerebrospinal fluid CSF), cerumen (earwax), chyle, chime, endolymph, perilymph, feces, breath, gastric acid, gastric juice, lymph, mucus (including nasal drainage and phlegm), pericardia! fluid, peritoneal fluid, pleural fluid, pus, rheum, saliva, exhaled breath condensates, 12. The devices or methods of any prior embodiment, wherein the layer of uniform thickness in the closed configuration is less than 150 um.

13. The method of any prior claim, wherein the pressing is provided by a pressured liquid, a pressed gas, or a conformal material.

14. The method of any prior claim, wherein the analyzing comprises counting cells in the layer of uniform thickness.

15. The method of any prior claim, wherein the analyzing comprises performing an assay in the layer of uniform thickness.

16. The devices or methods of any prior embodiment, wherein the assay is a binding assay or biochemical assay.

17. The method of any prior claim, wherein the sample deposited has a total volume less 0.5 ul.

18. The method of any prior claim, wherein multiple drops of sample are deposited onto one or both of the plates.

19. The devices or methods of any prior embodiment, wherein the inter-spacer distance is in the range of 1 µm to 120 um.

20. The devices or methods of any prior embodiment, wherein the inter-spacer distance is in the range of 120 µm to 50 um.

20. The devices or methods of any prior embodiment, wherein the inter-spacer distance is in the range of 120 µm to 200 um.

21. The device of any prior device claim, wherein the flexible plates have a thickness in the range of 20 µm to 250 µm and Young's modulus in the range 0.1 to 5 GPa.

22. The device of any prior device claim, wherein for a flexible plate, the thickness of the flexible plate times the Young's modulus of the flexible plate is in the range 60 to 750 GPa-um.

23. The device of any prior device claim, wherein the layer of uniform thickness sample is uniform over a lateral area that is at least 1 $mm^2$.

24. The device of any prior device claim, wherein the layer of uniform thickness sample is uniform over a lateral area that is at least 3 $mm^2$.

25. The device of any prior device claim, wherein the layer of uniform thickness sample is uniform over a lateral area that is at least 5 $mm^2$.

26. The device of any prior device cm, wherein the layer of uniform thickness sample is uniform over a lateral area that is at least 10 $mm^2$.

27. The device of any prior device claim, wherein the layer of uniform thickness sample is uniform over a lateral area that is at least 20 $mm^2$.

28. The device of any prior device claim, wherein the layer of uniform thickness sample is uniform over a lateral area that is in a range of 20 $mm^2$ to 100 $mm^2$.

29. The device of any prior device claim, wherein the layer of uniform thickness sample has a thickness uniformity of up to +/−5% or better.

30. The device of any prior device claim, wherein the layer of uniform thickness sample has a thickness uniformity of up to +/−10% or better.

31. The device of any prior device claim, wherein the layer of uniform thickness sample has a thickness uniformity of up to +/−20% or better.

33 The device of any prior device claim, wherein the layer of uniform thickness sample has a thickness uniformity of up to +/−30% or better.

34 The device of any prior device claim, wherein the layer of uniform thickness sample has a thickness uniformity of up to +/−40% or better.

35. The device of any prior device claim, wherein the layer of uniform thickness sample has a thickness uniformity of up to +/−50% or better.

36 The device of any prior device claim, wherein the spacers are pillars with a cross-sectional shape selected from round, polygonal, circular, square, rectangular, oval, elliptical, or any combination of the same.

37. The device of any prior device claim, wherein the spacers have pillar shape, have a substantially flat top surface, and have substantially uniform cross-section, wherein, for each spacer, the ratio of the lateral dimension of the spacer to its height is at least 1.

38 The device of any prior device claim, wherein the inter spacer distance is periodic.

39 The device of any prior device claim, wherein the spacers have a filling factor of 1% or higher, wherein the filling factor is the ratio of the spacer contact area to the total plate area.

40 The device of any prior device claim, wherein the Young's modulus of the spacers times the filling factor of the spacers is equal or larger than 20 MPa, wherein the filling factor is the ratio of the spacer contact area to the total plate area.

41. The device of any prior device claim, wherein the spacing between the two plates closed configuration is in less 200 um.

42. The device of any prior device claim, wherein the spacing between the two plates at the closed configuration is a value selected from between 1.8 um and 3.5 um.

43. The device of any prior device claim, wherein the spacing are fixed on a plate by directly embossing the plate or injection molding of the plate.

44. The device of any prior device claim, wherein the materials of the plate and the spacers are selected from polystyrene, PMMA, PC, COC, COP, or another plastic.

45. The device of any prior device claim, wherein the spacers have a pillar shape, and the sidewall corners of the spacers have a round shape with a radius of curvature at least 1 um.

46. The device of any prior device claim, wherein the spacers have a density of at least $1000/mm^2$.

47. The device of any prior device claim, wherein at least one of the plates is transparent.

48. The device of any prior device claim, wherein the mold used to make the spacers is fabricated by a mold containing features that are fabricated by either (a) directly reactive ion etching or ion beam etched or (b) by a duplication or multiple duplication of the features that are reactive ion etched or ion beam etched.

49. The devices or methods of any prior embodiment, wherein the spacers are configured, such that the filling factor is in the range of 1% to 5%.

50. The devices or methods of any prior embodiment, wherein the surface variation is relative to the spacer height and the ratio of the pillar flat top surface variation to the spacer height is less than 0.5%, 1%, 3%, 5%, 7%, 10%, 15%, 20%, 30%, 40%, or in a range between any two of the values. A preferred flat pillar top smoothness has a ratio of the pillar flat top surface variation to the spacer height is less than 2%, 5%, or 10%.

50. The devices or methods of any prior embodiment, wherein the spacers are configured, such that the filling factor is in the range of 1% to 5%.

51. The devices or methods of any prior embodiment, wherein the spacers are configured, such that the filling factor is in the range of 5% to 10%.

52. The devices or methods of any prior embodiment, wherein the spacers are configured, such that the filling factor is in the range of 10% to 20%.

The devices or methods of any prior embodiment, wherein the spacers are configured, such that the filling factor is in the range of 20% to 30%.

The devices or methods of any prior embodiment, wherein the spacers are configured, such that the filling factor is 5%, 10%, 20%, 30%, 40%, 50%, or in a range of any two of the values.

55. The devices or methods of any prior embodiment, wherein the spacers are configured, such that the filling factor is 50%, 60%, 70%, 80%, or in a range of any two of the values.

56. The devices or methods of any prior embodiment, wherein the spacers are configured, such that the filling factor multiplies the Young's modulus of the spacer is in the range of 2 MPa and 10 MPa.

57. The devices or methods of any prior embodiment, wherein the spacers are configured, such that the filling factor multiplies the Young's modulus of the spacer is in the range of 10 MPa and 20 MPa.

58. The devices or methods of any prior embodiment, wherein the spacers are configured, such that the filling factor multiplies the Young's modulus of the spacer is in the range of 20 MPa and 40 MPa.

59. The devices or methods of any prior embodiment, wherein the spacers are configured, such that the filling factor multiplies the Young's modulus of the spacer is in the range of 40 MPa and 80 MPa.

60. The devices or methods of any prior embodiment, wherein the spacers are configured, such that the filling factor multiplies the Young's modulus of the spacer is in the range of 80 MPa and 120 MPa.

61. The devices or methods of any prior embodiment, wherein the spacers are configured, such that the filling factor multiplies the Young's modulus of the spacer is in the range of 120 MPa to 150 MPa.

62. The devices or methods of any prior embodiment, wherein the device further comprises a dry reagent coated on one or both plates.

63. The devices or methods of any prior embodiment, wherein the device further comprises, on one or both plates, a dry binding site that has a predetermined area, wherein the dry binding site binds to and immobilizes an analyte in the sample.

64. The devices or methods of any prior embodiment, wherein the device further comprises, on one or both plates, a releasable dry reagent and a release time control material that delays the time that the releasable dry regent is released into the sample.

65 The device of any prior embodiment, wherein the release time control material delays the time that the dry regent is released into the sample by at least 3 seconds.

66. The device of any prior embodiment, wherein the regent comprises anticoagulant and/or staining reagent(s).

67. The device of any prior embodiment, wherein the reagent comprises cell lysing reagent(s).

68. The devices or methods of any prior embodiment, wherein the device further comprises, on one or both plates, one or a plurality of dry binding sites and/or one or a plurality of reagent sites.

69. The device of any prior device embodiment, wherein the analyte comprises a molecule (e.g., a protein, peptides, DNA, RNA, nucleic acid, or other molecule), cells, tissues, viruses, and nanoparticles with different shapes.

70 The device of any prior device embodiment, wherein the analyte comprises white blood cells, red blood cells and platelets.

71. The device of any prior device embodiment, wherein the analyte is stained.

72. The devices or methods of any prior embodiment, wherein the spacers regulating the layer of uniform thickness have a filling factor of at least 1%, wherein the filling factor is the ratio of the spacer area in contact with the layer of uniform thickness to the total plate area in contact with the layer of uniform thickness.

73. The devices or methods of any prior embodiment, wherein for spacers regulating the layer of uniform thickness, the Young's modulus of the spacers times the filling factor of the spacers is equal or larger than 10 MPa, wherein the filling factor is the ratio of the spacer area in contact with the layer of uniform thickness to the total plate area in contact with the layer of uniform thickness.

74 The devices or methods of any prior embodiment, wherein for a flexible plate, the thickness of the flexible plate times the Young's modulus of the flexible plate is in the range 60 to 750 GPa-um.

75 The devices or methods of any prior embodiment, wherein for a flexible plate, the fourth power of the inter-spacer-distance (ISO) divided by the thickness of the flexible plate (h) and the Young's modulus (E) of the flexible plate, ISO4/(h E), is equal to or less than 106 um3/GPa.

76 The devices or methods of any prior embodiment, wherein one or both plates comprise a location marker, either on a surface of or inside the plate, that provide information of a location of the plate.

77 The devices or methods of any prior embodiment, wherein one or both plates comprise a scale marker, either on a surface of or inside the plate, that provide information of a lateral dimension of a structure of the sample and/or the plate.

78. The devices or methods of any prior embodiment, wherein one or both plates comprise an imaging marker, either on surface of or inside the plate, that assists an imaging of the sample.

79. The devices or methods of any prior embodiment, wherein the spacers functions as a location marker, a scale marker, an imaging marker, or any combination of thereof.

80. The devices or methods of any prior embodiment, wherein the average thickness of the layer of uniform thickness is about equal to a minimum dimension of an analyte in the sample.

81. The devices or methods of any prior embodiment, wherein the inter-spacer distance is in the range of 7 um to 50 um.

The devices or methods of any prior embodiment, wherein the inter-spacer distance is in the range of 50 µm to 120 um.

82. The devices or methods of any prior embodiment, wherein the inter-spacer distance is in the range of 120 µm to 200 um (micron).

83. The devices or methods of any prior embodiment, wherein the inter-spacer distance is substantially periodic.

84. The devices or methods of any prior embodiment, wherein the spacers are pillars with a cross-sectional shape selected from round, polygonal, circular, square, rectangular, oval, elliptical, or any combination of the same.

85. The devices or methods of any prior embodiment, wherein the spacers have are pillar shape and have a substantially flat top surface, wherein, for each spacer, the ratio of the lateral dimension of the spacer to its height is at least 1.

86. The devices or methods of any prior embodiment, wherein each spacer has the ratio of the lateral dimension of the spacer to its height is at least 1.

87. The devices or methods of any prior embodiment, wherein the minimum lateral dimension of spacer is less than or substantially equal to the minimum dimension of an analyte in the sample.

88. The devices or methods of any prior embodiment, wherein the minimum lateral dimension of spacer is in the range of 0.5 µm to 100 um.

89. The devices or methods of any prior embodiment, wherein the minimum lateral 90. The devices or methods of any prior embodiment, wherein the sample is blood.

91. The devices or methods of any prior embodiment, wherein the sample is whole blood without dilution by liquid.

92. The devices or methods of any prior embodiment, wherein the sample is a biological sample selected from amniotic fluid, aqueous humour, vitreous humour, blood (e.g., whole blood, fractionated blood, plasma or serum), breast milk, cerebrospinal fluid (CSF), cerumen (earwax), chyle, chime, endolymph, perilymph, feces, breath, gastric acid, gastric juice, lymph, mucus (including nasal drainage and phlegm), pericardia! fluid, peritoneal fluid, pleural fluid, pus, rheum, saliva, exhaled breath condensates, sebum, semen, sputum, sweat, synovial fluid, tears, vomit, and urine.

93. The devices or methods of any prior embodiment, wherein the sample is a biological sample, an environmental sample, a chemical sample, or clinical sample.

94. dimension of spacer is in the range of 0.5 µm to 10 um.

95. The devices or methods of any prior embodiment, wherein the spacers have a pillar shape, and the sidewall corners of the spacers have a round shape with a radius of curvature at least 1 um.

96. The devices or methods of any prior embodiment, wherein the spacers have a density of at least $100/mm^2$.

97. The devices or methods of any prior embodiment, wherein the spacers have a density of at least $1000/mm^2$.

98. The devices or methods of any prior embodiment, wherein at least one of the plates is transparent.

99. The devices or methods of any prior embodiment, wherein at least one of the plates is made from a flexible polymer.

100. The devices or methods of any prior embodiment, wherein, for a pressure that compresses the plates, the spacers are not compressible and/or, independently, only one of the plates is flexible.

101. The device of any of any prior embodiment, wherein the flexible plate has a thickness in the range of 10 µm to 200 um.

102. The devices or methods of any prior embodiment, wherein the variation is less than 30%.

103. The devices or methods of any prior embodiment, wherein the variation is less than 10%.

104. The devices or methods of any prior embodiment, wherein the variation is less than 5%.

105. The devices or methods of any prior embodiment, wherein the first and second plates are connected and are configured to be changed from the open configuration to the closed configuration by folding the plates.

106. The devices or methods of any prior embodiment, wherein the first and second plates are connected by a hinge and are configured to be changed from the open configuration to the closed configuration by folding the plates along the hinge.

107. The devices or methods of any prior embodiment, wherein the first and second plates are connected by a hinge that is a separate material to the plates, and are configured to be changed from the open configuration to the closed configuration by folding the plates along the hinge 108. The devices or methods of any prior embodiment, wherein the first and second plates are made in a single piece of material and are configured to be changed from the open configuration to the closed configuration by folding the plates.

109. The devices or methods of any prior embodiment, wherein the layer of uniform thickness sample is uniform over a lateral area that is at least 1 $mm^2$.

110. The devices or methods of any prior embodiment, wherein the device is configured to analyze the sample in 60 seconds or less.

111. The devices or methods of any prior embodiment, wherein at the closed configuration, the final sample thickness device is configured to analyze the sample in 60 seconds or less.

112. The devices or methods of any prior embodiment, wherein at the closed configuration, the final sample thickness device is configured to analyze the sample in 10 seconds or less.

113. The devices or methods of any prior embodiment, wherein the dry binding site comprises a capture agent.

114. The devices or methods of any prior embodiment, wherein the dry binding site comprises an antibody or nucleic acid.

115. The devices or methods of any prior embodiment, wherein the releasable dry reagent is a labeled reagent.

116. The devices or methods of any prior embodiment, wherein the releasable dry reagent is a fluorescently-labeled reagent.

117. The devices or methods of any prior embodiment, wherein the releasable dry reagent is a fluorescently-labeled antibody.

118. The devices or methods of any prior embodiment, wherein the releasable dry reagent is a cell stain.

119. The devices or methods of any prior embodiment, wherein the releasable dry reagent is a cell lysing.

120. The devices or methods of any prior embodiment, wherein the detector is an optical detector that detects an optical signal.

121. The devices or methods of any prior embodiment, wherein the detector is an electric detector that detect electrical signal.

122. The device of any prior device embodiment, wherein the spacing are fixed on a plate by directly embossing the plate or injection molding of the plate.

123. The device of any prior device embodiment, wherein the materials of the plate and the spacers are selected from polystyrene, PMMA, PC, COC, COP, or another plastic.

124. A system for rapidly analyzing a sample using a mobile phone comprising:
(a) a device of any prior embodiment;
(b) a mobile communication device comprising:
 i. one or a plurality of cameras for the detecting and/or imaging the sample;
 ii. electronics, signal processors, hardware and software for receiving and/or processing the detected signal and/or the image of the sample and for remote communication; and
(c) a light source; a light source from either the mobile communication device or an external source, wherein the detector in the devices or methods of any prior embodiment is provided by the mobile communication device, and detects an analyte in the sample at the closed configuration.

125. The system of any prior system embodiment, wherein one of the plates has a binding site that binds an analyte, wherein at least part of the uniform sample thickness layer is over the binding site, and is substantially less than the average lateral linear dimension of the binding site.

126. The system of any prior system embodiment, further comprising: a housing configured to hold the sample and to be mounted to the mobile communication device.

127. The system of any prior system embodiment, wherein the housing comprises optics for facilitating the imaging and/or signal processing of the sample by the mobile communication device, and a mount configured to hold the optics on the mobile communication device.

128. The system of any prior system embodiment, wherein an element of the optics in the housing is movable relative to the housing.

129. The system of any prior system embodiment, wherein the mobile communication device is configured to communicate test results to a medical professional, a medical facility or an insurance company.

130. The system of any prior system embodiment, wherein the mobile communication device is further configured to communicate information on the test and the subject with the medical professional, medical facility or insurance company.

131. The system of any prior system embodiment, wherein the mobile communication device is further configured to communicate information of the test to a cloud network, and the cloud network process the information to refine the test results.

132. The system of any prior system embodiment, wherein the mobile communication device is further configured to communicate information of the test and the subject to a cloud network, the cloud network process the information to refine the test results, and the refined test results will send back the subject.

133. The system of any prior system embodiment, wherein the mobile communication device is configured to receive a prescription, diagnosis or a recommendation from a medical professional.

134. The system of any prior system embodiment, wherein the mobile communication device is configured with hardware and software to:
(a) capture an image of the sample;
(b) analyze a test location and a control location in in image; and
(c) compare a value obtained from analysis of the test location to a threshold value that characterizes the rapid diagnostic test.

135. The system of any prior system embodiment, wherein at least one of the plates comprises a storage site in which assay reagents are stored.

136. The system of any prior system embodiment, at least one of the cameras reads a signal from the device.

137. The system of any prior system embodiment, wherein the mobile communication device communicates with the remote location via a wifi or cellular network.

138. The system of any prior system embodiment, wherein the mobile communication device is a mobile phone.

139. A method for rapidly analyzing an analyte in a sample using a mobile phone, comprising:
(a) depositing a sample on the device of any prior system embodiment;
(b) assaying an analyte in the sample deposited on the device to generate a result; and
(c) communicating the result from the mobile communication device to a location remote from the mobile communication device.

140. The method of any prior embodiments embodiment, wherein the analyte comprises a molecule (e.g., a protein, peptides, DNA, RNA, nucleic acid, or other molecule), cells, tissues, viruses, and nanoparticles with different shapes.

141. The method of any prior embodiment, wherein the analyte comprises white blood cell, red blood cell and platelets.

142. The method of any prior embodiment, wherein the assaying comprises performing a white blood cells differential assay.

143. The method of any prior embodiments embodiment, wherein the method comprises: analyzing the results at the remote location to provide an analyzed result; and communicating the analyzed result from the remote location to the mobile communication device.

144. The method of any prior embodiment, wherein the analysis is done by a medical professional at a remote location.

145. The method of any prior embodiment, wherein the mobile communication device receives a prescription, diagnosis or a recommendation from a medical professional at a remote location.

146. The method of any prior embodiment, wherein the sample is a bodily fluid.

147. The method of any prior embodiment, wherein the bodily fluid is blood, saliva or urine.

148. The method of any prior embodiment, wherein the sample is whole blood without dilution by a liquid.

149. The method of any prior embodiment, wherein the assaying step comprises detecting an analyte in the sample.

150. The method of any prior embodiment, wherein the analyte is a biomarker.

151. The method of any prior embodiment, wherein the analyte is a protein, nucleic acid, cell, or metabolite.

152. The method of any prior embodiment, wherein the method comprises counting the number of red blood cells.

153. The method of any of any prior embodiment, wherein the method comprises counting 154. The method of any prior embodiment, wherein method comprises staining the cells in the sample and counting the number of neutrophils, lymphocytes, monocytes, eosinophils and basophils.

155. The method of any prior embodiments embodiment, wherein the assay done in step (b) is a binding assay or a biochemical assay.

156. A method for analyzing a sample comprising:
obtaining a device of any prior device embodiment;
depositing the sample onto one or both pates of the device;
placing the plates in a closed configuration and applying an external force over at least part of the plates; and
analyzing the sample in the layer of uniform thickness while the plates are the closed configuration.

157. The devices or methods of any prior embodiment, wherein the first plate further comprises, on its surface, a first predetermined assay site and a second predetermined assay site, wherein the distance between the edges of the assay site is substantially larger than the thickness of the uniform thickness layer when the plates are in the closed position, wherein at least a part of the uniform thickness layer is over the predetermined assay sites, and wherein the sample has one or a plurality of analytes that are capable of diffusing in the sample.

158. The devices or methods of any prior embodiment, wherein the first plate has, on its surface, at least three analyte assay sites, and the distance between the edges of any two neighboring assay sites is substantially larger than the thickness of the uniform
thickness layer when the plates are in the closed position, wherein at least a part of the uniform thickness layer is over the assay sites, and wherein the sample has one or a plurality of analytes that are capable of diffusing in the sample.

159. The devices or methods of any prior embodiment, wherein the first plate has, on its surface, at least two neighboring analyte assay sites that are not separated by a distance that is substantially larger than the thickness of the uniform thickness layer when the plates are in the closed position, wherein at least a part of the uniform thickness layer is over the assay sites, and wherein the sample has one or a plurality of analytes that are capable of diffusing in the sample.

160. The devices or methods of any prior embodiment, wherein the analyte assay area is between a pair of electrodes.

161. The devices or methods of any prior embodiment, wherein the assay area is defined by a patch of dried reagent.

162. The devices or methods of any prior embodiment, wherein the assay area binds to and immobilizes the analyte.

163. The devices or methods of any prior embodiment, wherein the assay area is defined by a patch of binding reagent that, upon contacting the sample, dissolves into the sample, diffuses in the sample, and binds to the analyte.

164. The devices or methods of any prior embodiment, wherein the inter-spacer distance is in the range of 14 um to 200 um.

165. The devices or methods of any prior embodiment, wherein the inter-spacer distance is in the range of 7 um to 20 um.

166. The devices or methods of any prior embodiment, wherein the spacers are pillars with a cross-sectional shape selected from round, polygonal, circular, square, rectangular, oval, elliptical, or any combination of the same.

167. The devices or methods of any prior embodiment, wherein the spacers have a pillar shape and have a substantially flat top surface, wherein, for each spacer, the ratio of the lateral dimension of the spacer to its height is at least 1.

168. The devices or methods of any prior embodiment, wherein the spacers have a pillar shape, and the sidewall corners of the spacers have a round shape with a radius of curvature at least 1 um.

169. The devices or methods of any prior embodiment, wherein the spacers have a density of at least $1000/mm^2$.

170. The devices or methods of any prior embodiment, wherein at least one of the plates is transparent.

171. The devices or methods of any prior embodiment, wherein at least one of the plates is made from a flexible polymer.

172. The devices or methods of any prior embodiment, wherein only one of the plates is flexible.

173. The device of any prior embodiment, wherein the area-determination device is a camera.

174. The area-determination device comprises an area in the sample contact area of a plate, wherein the area is less than $1/100$, $1/20$, $1/10$, $1/6$, $1/5$, $1/4$, $1/3$, $1/2$, $2/3$ of the sample contact area, or in a range between any of the two values.

175. The area-determination device comprises a camera and an area in the sample contact area of a plate, wherein the area is in contact with the sample.

176. The devices or methods of any prior embodiment, wherein the deformable sample comprises a liquid sample.

177. The devices or methods of any prior embodiment, wherein the imprecision force has a variation at least 30% of the total force that actually is applied.

178. The devices or methods of any prior embodiment, wherein the imprecision force has a variation at least 20%, 30%, 40%, 50%, 60, 70%, 80%, 90%100%, 150%, 200%, 300%, 500%, or in a range of any two values, of the total force that actually is applied.

179. The device of any prior embodiment, wherein spacers have a flat top.

180. The device of any prior embodiment, wherein the device is further configured to have, after the pressing force is removed, a sample thickness that is substantially the same in thickness and uniformity as that when the force is applied.

181. The device of any prior embodiment, wherein the imprecise force is provided by human hand.

182. The device of any prior embodiment, wherein the inter spacer distance is substantially constant.

183. The device of any prior embodiment, wherein the inter spacer distance is substantially periodic in the area of the uniform sample thickness area.

184. The device of any prior embodiment, wherein the multiplication product of the filling factor and the Young's modulus of the spacer is 2 MPa or larger.

185. The device of any prior embodiment, wherein the force is applied by hand directly or indirectly/

186. The device of any prior embodiment, wherein the force applied is in the range of 1 N to 20 N.

187. The device of any prior embodiment, wherein the force applied is in the range of 20 N to 200 N.

188. The device of any prior embodiment wherein the highly uniform layer has a thickness that varies by less than 15%, 10%, or 5% of an average thickness.

189. The device of any prior embodiment, wherein the imprecise force is applied by pinching the device between a thumb and forefinger.

190. The device of any prior embodiment, wherein the predetermined sample thickness is larger than the spacer height.

191. The device of any prior embodiment, wherein the device holds itself in the closed configuration after the pressing force has been removed.

192. The device of any prior embodiment, wherein the uniform thickness sample layer area is larger than that area upon which the pressing force is applied.

193. The device of any prior embodiment, wherein the spacers do not significantly deform during application of the pressing force.

194. The device of any prior embodiment, wherein the pressing force is not predetermined beforehand and is not measured.

195. In some embodiments, the fluidic sample is replaced by a deformable sample and the embodiments for making at least a part of the fluidic sample into a uniform thickness layer can make at least a part of the deformable sample into a uniform thickness layer.

196. The devices and methods of any prior device claim, wherein the inter spacer distance is periodic.

197. The devices and methods of any prior device claim, wherein the spacers have a flat top.

198. The devices and methods of any prior device claim, wherein the inter spacer distance is at least two times large than the size of the targeted analyte in the sample.

Manufacturing of Q-Card

MA1. An embodiment of the Q-Card comprising: a first plate, a second plate, and a hinge, wherein
  i. the first plate, that is about 200 nm to 1500 nm thick, comprises, on its inner surface, (a) a sample contact area for contacting a sample, and (b) a sample overflow dam that surrounds the sample contact area is configured to present a sample flow outside of the dam;
  ii. the second plate is 10 μm to 250 μm thick and comprises, on its inner surface, (a) a sample contact area for contacting a sample, and (b) spacers on the sample contact area;
  iii. the hinge that connect the first and the second plates; and wherein the first and second plate are movable relative to each other around the axis of the hinge.

MA2. An embodiment of the Q-Card comprising: a first plate, a second plate, and a hinge, wherein
  i. the first plate, that is about 200 nm to 1500 nm thick, comprises, on its inner surface, (a) a sample contact area for contacting a sample, (b) a sample overflow dam that surrounds the sample contact area is configured to present a sample flow outside of the dam, and (c) spacers on the sample contact area;
  ii. the second plate, that is 10 μm to 250 μm thick, comprises, on its inner surface,
  iii. a sample contact area for contacting a sample; the hinge that connect the first and the second plates; and wherein the first and second plate are movable relative to each other around the axis of the hinge.

MA3. An embodiment of the Q-Card comprising: a first plate, a second plate, and a hinge, wherein i. the first plate, that is about 200 nm to 1500 nm thick, comprises, on its inner surface, (a) a sample contact area for contacting a sample, and (b) spacers on the sample contact area; ii. the second plate, that is 10 μm to 250 μm thick, comprises, on its inner surface, a sample contact area for contacting a sample, and (b) a sample overflow dam that surrounds the sample contact area is configured to present a sample flow outside of the dam, and iii. the hinge that connects the first and the second plates; and wherein the first and second plate are movable relative to each other around the axis of the hinge.

MA4 An embodiment of the Q-Card comprising: a first plate, a second plate, and a hinge, wherein the first plate, that is about 200 nm to 1500 nm thick, comprises, on its inner surface, a sample contact area for contacting a sample; ii. the second plate, that is 10 μm to 250 μm thick, comprises, on its inner surface,
  (a) sample contact area for contacting a sample, (b) a sample overflow dam that surrounds the sample contact area is configured to present a sample flow outside of the dam, and (c) spacers on the sample contact area; and the hinge that connect the first and the second plates; and wherein the first and second plate are movable relative to each other around the axis of the hinge.

M1 An embodiment of a method for fabricating the Q-Card of any embodiments of MA1 to MA4, comprising:
  (a) injection molding of the first plate,
  (b) nanoimprinting or extrusion printing of the second plate.

M2 An embodiment of a method for fabricating the Q-Card of any embodiments of MA1 to MA4, comprising:
  (a) Laser cutting the first plate, and
  (b) nanoimprinting or extrusion printing of the second plate.

M3 An embodiment of a method for fabricating the Q-Card of any embodiments of MA1 to MA4, comprising:
  (a) Injection molding and laser cutting the first plate, and
  (b) nanoimprinting or extrusion printing of the second plate.

M4 An embodiment of a method for fabricating the Q-Card of any embodiments of MA1 to MA4, comprising: nanoimprinting or extrusion printing to fabricated both the first and the second plate.

M5 An embodiment of a method for fabricating the Q-Card of any embodiments of MA1 to MA4, comprising: fabricating the first plate or the second plate, using injection molding, laser cutting the first plate, nanoimprinting, extrusion printing, or a combination of thereof.

The method of any embodiments of M1-M5, wherein the method further comprises a step of attaching the hinge on the first and the second plates after the fabrication of the first and second plates.

In the device, kit and method of any prior embodiment, wherein the thickness of the stain solution layer is configured to have, at a closed configuration, a thickness that the stained cell or any part of the cell being stained is visible without out removing (e.g. washing away) the staining solution layer between the tissue and the second plate.

Compressed Regulated Open Flow" (CROF)

In assaying, a manipulation of a sample or a reagent can lead to improvements in the assaying. The manipulation includes, but not limited to, manipulating the geometric shape and location of a sample and/or a reagent, a mixing or a binding of a sample and a reagent, and a contact area of a sample of reagent to a plate.

Many embodiments of the present invention manipulate the geometric size, location, contact areas, and mixing of a sample and/or a reagent using a method, termed "compressed regulated open flow (CROF)", and a device that performs CROF.

The term "compressed open flow (COF)" refers to a method that changes the shape of a flowable sample deposited on a plate by (i) placing other plate on top of at least a part of the sample and (ii) then compressing the sample between two plates by pushing the two plates towards each other; wherein the compression reduces a thickness of at least a part of the sample and makes the sample flow into open spaces between the plates.

The term "compressed regulated open flow" or "CROF" (or "self-calibrated compressed open flow" or "SCOF" or "SCCOF") refers to a particular type of COF, wherein the final thickness of a part or entire sample after the compression is "regulated" by spacers, wherein the spacers are placed between the two plates.

The term "the final thickness of a part or entire sample is regulated by spacers" in a CROF means that during a CROF, once a specific sample thickness is reached, the relative movement of the two plates and hence the change of sample thickness stop, wherein the specific thickness is determined by the spacer.

One embodiment of the method of CROF, as illustrated in FIG. 1, comprises:
(a) obtaining a sample, that is flowable;
(b) obtaining a first plate and a second plate that are movable relative to each other into different configurations, wherein each plate has a sample contact surface that is substantially planar, wherein one or both of the plates comprise spacers and the spacers have a predetermined height, and the spacers are on a respective sample contacting surface;
(c) depositing, when the plates are configured in an open configuration, the sample on one or both of the plates; wherein the open configuration is a configuration in which the two plates are either partially or completely separated apart and the spacing between the plates is not regulated by the spacers; and
(d) after (c), spreading the sample by bringing the plates into a closed configuration, wherein, in the closed configuration: the plates are facing each other, the spacers and a relevant volume of the sample are between the plates, the thickness of the relevant volume of the sample is regulated by the plates and the spacers, wherein the relevant volume is at least a portion of an entire volume of the sample, and wherein during the sample spreading, the sample flows laterally between the two plates.

The term "plate" refers to, unless being specified otherwise, the plate used in a CROF process, which a solid that has a surface that can be used, together with another plate, to compress a sample placed between the two plate to reduce a thickness of the sample.

The term "the plates" or "the pair of the plates" refers to the two plates in a CROF process. The term "first plate" or "second plate" refers to the plate use in a CROF process.

The term "the plates are facing each other" refers to the cases where a pair of plates are at least partially facing each other.

The term "spacers" or "stoppers" refers to, unless stated otherwise, the mechanical objects that set, when being placed between two plates, a limit on the minimum spacing between the two plates that can be reached when compressing the two plates together. Namely, in the compressing, the spacers will stop the relative movement of the two plates to prevent the plate spacing becoming less than a preset (i.e. predetermined) value. There are two types of the spacers: "open-spacers" and "enclosed-spacers".

The term "open-spacer" means the spacer have a shape that allows a liquid to flow around the entire perimeter of the spacer and flow pass the spacer. For example, a pillar is an open spacer.

The term of "enclosed spacer" means the spacer of having a shape that a liquid cannot flow abound the entire perimeter of the spacer and cannot flow pass the spacer. For example, a ring shape spacer is an enclosed spacer for a liquid inside the ring, where the liquid inside the ring spacer remains inside the ring and cannot go to outside (outside perimeter).

The term "a spacer has a predetermined height" and "spacers have predetermined inter-spacer distance" means, respectively, that the value of the spacer height and the inter spacer distance is known prior to a CROF process. It is not predetermined, if the value of the spacer height and the inter-spacer distance is not known prior to a CROF process. For example, in the case that beads are sprayed on a plate as spacers, where beads are landed on random locations of the plate, the inter-spacer distance is not predetermined. Another example of not predetermined inter spacer distance is that the spacers moves during a CROF processes.

The term "a spacer is fixed on its respective plate" in a CROF process means that the spacer is attached to a location of a plate and the attachment to that location is maintained during a CROF (i.e. the location of the spacer on respective plate does not change). An example of "a spacer is fixed with its respective plate" is that a spacer is monolithically made of one piece of material of the plate, and the location of the spacer relative to the plate surface does not change during CROF. An example of "a spacer is not fixed with its respective plate" is that a spacer is glued to a plate by an adhesive, but during a use of the plate, during CROF, the adhesive cannot hold the spacer at its original location on the plate surface and the spacer moves away from its original location on the plate surface.

The term "a spacer is fixed to a plate monolithically" means the spacer and the plate behavior like a single piece of an object where, during a use, the spacer does not move or separated from its original location on the plate.

The term "open configuration" of the two plates in a CROF process means a configuration in which the two plates are either partially or completely separated apart and the spacing between the plates is not regulated by the spacers The term "closed configuration" of the two plates in a CROF process means a configuration in which the plates are facing each other, the spacers and a relevant volume of the sample are between the plates, the thickness of the relevant volume of the sample is regulated by the plates and the spacers, wherein the relevant volume is at least a portion of an entire volume of the sample.

The term "a sample thickness is regulated by the plate and the spacers" in a CROF process means that for a give condition of the plates, the sample, the spacer, and the plate compressing method, the thickness of at least a port of the sample at the closed configuration of the plates can be predetermined from the properties of the spacers and the plate.

The term "inner surface" or "sample surface" of a plate in a CROF device refers to the surface of the plate that touches the sample, while the other surface (that does not touch the sample) of the plate is termed "outer surface".

The term "X-Plate" of a CROF device refers to a plate that comprises spaces that are on the sample surface of the plate, wherein the spacers have a predetermined inter-spacer distance and spacer height, and wherein at least one of the spacers is inside the sample contact area.

The term "CROF device" refers to a device that performs a CROF process. The term "CROFed" means that a CROF process is used. For example, the term "a sample was CROFed" means that the sample was put inside a CROF device, a CROF process was performed, and the sample was hold, unless stated otherwise, at a final configuration of the CROF.

The term "CROF plates" refers to the two plates used in performing a CROF process.

The term "surface smoothness" or "surface smoothness variation" of a planar surface refers to the average deviation of a planar surface from a perfect flat plane over a short distance that is about or smaller than a few micrometers. The surface smoothness is different from the surface flatness variation. A planar surface can have a good surface flatness, but poor surface smoothness.

The term "surface flatness" or "surface flatness variation" of a planar surface refers to the average deviation of a planar surface from a perfect flat plane over a long distance that is about or larger than 10 um. The surface flatness variation is different from the surface smoothness. A planar surface can have a good surface smoothness, but poor surface flatness (i.e. large surface flatness variation).

The term "relative surface flatness" of a plate or a sample is the ratio of the plate surface flatness variation to the final sample thickness.

The term "final sample thickness" in a CROF process refers to, unless specified otherwise, the thickness of the sample at the closed configuration of the plates in a CORF process.

The term "compression method" in CROF refers to a method that brings two plates from an open configuration to a closed configuration.

The term of "interested area" or "area of interest" of a plate refers to the area of the plate that is relevant to the function that the plates perform.

The term "at most" means "equal to or less than". For example, a spacer height is at most 1 um, it means that the spacer height is equal to or less than 1 um.

The term "sample area" means the area of the sample in the direction approximately parallel to the space between the plates and perpendicular to the sample thickness.

The term "sample thickness" refers to the sample dimension in the direction normal to the surface of the plates that face each other (e.g., the direction of the spacing between the plates). The term "plate-spacing" refers to the distance between the inner surfaces of the two plates.

The term "deviation of the final sample thickness" in a CROF means the difference between the predetermined spacer height (determined from fabrication of the spacer) and the average of the final sample thickness, wherein the average final sample thickness is averaged over a given area (e.g. an average of 25 different points (4 mm apart) over 1.6 cm by 1.6 cm area).

The term "uniformity of the measured final sample thickness" in a CROF process means the standard deviation of the measured final sample thickness over a given sample area (e.g. the standard deviation relative to the average.).

The term "relevant volume of a sample" and "relevant area of a sample" in a CROF process refers to, respectively, the volume and the area of a portion or entire volume of the sample deposited on the plates during a CROF process, that is relevant to a function to be performed by a respective method or device, wherein the function includes, but not limited to, reduction in binding time of analyte or entity, detection of analytes, quantify of a volume, quantify of a concentration, mixing of reagents, or control of a concentration (analytes, entity or reagents).

The term "some embodiments", "in some embodiments" "in the present invention, in some embodiments", "embodiment", "one embodiment", "another embodiment", "certain embodiments", "many embodiments", or alike refers, unless specifically stated otherwise, to an embodiment(s) that is (are) applied to the entire disclosure (i.e. the entire invention).

The term "height" or "thickness" of an object in a CROF process refers to, unless specifically stated, the dimension of the object that is in the direction normal to a surface of the plate. For example, spacer height is the dimension of the spacer in the direction normal to a surface of the plate, and the spacer height and the spacer thickness means the same thing.

The term "area" of an object in a CROF process refers to, unless specifically stated, the area of the object that is parallel to a surface of the plate. For example, spacer area is the area of the spacer that is parallel to a surface of the plate.

The term "lateral" or "laterally" in a CROF process refers to, unless specifically stated, the direction that is parallel to a surface of the plate.

The term "width" of a spacer in a CROF process refers to, unless specifically stated, a lateral dimension of the spacer.

The term "a spacer inside a sample" means that the spacer is surrounded by the sample (e.g. a pillar spacer inside a sample).

The term "critical bending span" of a plate in a CROF process refers the span (i.e. distance) of the plate between two supports, at which the bending of the plate, for a given flexible plate, sample, and compression force, is equal to an allowed bending. For example, if an allowed bending is 50 nm and the critical bending span is 40 um for a given flexible plate, sample, and compression force, the bending of the plate between two neighboring spacers 40 um apart will be 50 nm, and the bending will be less than 50 nm if the two neighboring spacers is less than 40 um.

The term "flowable" for a sample means that when the thickness of the sample is reduced, the lateral dimension increases. For an example, a stool sample is regarded flowable.

The term "cell" and "target cell" are interchangeable.

In some embodiments of the present invention, a sample under a CROF process do not to be flowable to benefit from the process, as long as the sample thickness can be reduced under a CROF process. For an example, to stain a tissue by put a dye on a surface of the CROF plate, a CROF process can reduce the tissue thickness and hence speed up the saturation incubation time for staining by the dye.

The terms "CROF Card (or card)", "COF Card", "QMAX-Card", "Q-Card", "CROF device", "COF device", "QMAX-device", "CROF plates", "COF plates", and "QMAX-plates" are interchangeable, except that in some embodiments, the COF card does not comprise spacers; and the terms refer to a device that comprises a first plate and a second plate that are movable relative to each other into different configurations (including an open configuration and a closed configuration), and that comprises spacers (except some embodiments of the COF) that regulate the spacing between the plates. The term "X-plate" refers to one of the two plates in a CROF card, wherein the spacers are fixed to this plate. More descriptions of the COF Card, CROF Card, and X-plate are described in the provisional application Ser. Nos. 62/456,065, filed on Feb. 7, 2017, which is incorporated herein in its entirety for all purposes.

ADDITIONAL NOTES

Further examples of inventive subject matter according to the present disclosure are described in the following enumerated paragraphs.

It must be noted that as used herein and in the appended claims, the singular forms "a", "an", and "the" include plural referents unless the context clearly dictates otherwise, e.g., when the word "single" is used. For example, reference to "an analyte" includes a single analyte and multiple analytes, reference to "a capture agent" includes a single capture agent and multiple capture agents, reference to "a detection agent" includes a single detection agent and multiple detection agents, and reference to "an agent" includes a single agent and multiple agents.

As used herein, the terms "adapted" and "configured" mean that the element, component, or other subject matter is designed and/or intended to perform a given function. Thus, the use of the terms "adapted" and "configured" should not be construed to mean that a given element, component, or other subject matter is simply "capable of" performing a given function. Similarly, subject matter that is recited as being configured to perform a particular function may additionally or alternatively be described as being operative to perform that function.

As used herein, the phrase, "for example," the phrase, "as an example," and/or simply the terms "example" and "exemplary" when used with reference to one or more components, features, details, structures, embodiments, and/or methods according to the present disclosure, are intended to convey that the described component, feature, detail, structure, embodiment, and/or method is an illustrative, non-exclusive example of components, features, details, structures, embodiments, and/or methods according to the present disclosure. Thus, the described component, feature, detail, structure, embodiment, and/or method is not intended to be limiting, required, or exclusive/exhaustive; and other components, features, details, structures, embodiments, and/or methods, including structurally and/or functionally similar and/or equivalent components, features, details, structures, embodiments, and/or methods, are also within the scope of the present disclosure.

As used herein, the phrases "at least one of" and "one or more of," in reference to a list of more than one entity, means any one or more of the entity in the list of entity, and is not limited to at least one of each and every entity specifically listed within the list of entity. For example, "at least one of A and B" (or, equivalently, "at least one of A or B," or, equivalently, "at least one of A and/or B") may refer to A alone, B alone, or the combination of A and B.

As used herein, the term "and/or" placed between a first entity and a second entity means one of (1) the first entity, (2) the second entity, and (3) the first entity and the second entity. Multiple entity listed with "and/or" should be construed in the same manner, i.e., "one or more" of the entity so conjoined. Other entity may optionally be present other than the entity specifically identified by the "and/or" clause, whether related or unrelated to those entities specifically identified.

Where numerical ranges are mentioned herein, the invention includes embodiments in which the endpoints are included, embodiments in which both endpoints are excluded, and embodiments in which one endpoint is included and the other is excluded. It should be assumed that both endpoints are included unless indicated otherwise. Furthermore, unless otherwise indicated or otherwise evident from the context and understanding of one of ordinary skill in the art.

In the event that any patents, patent applications, or other references are incorporated by reference herein and (1) define a term in a manner that is inconsistent with and/or (2) are otherwise inconsistent with, either the non-incorporated portion of the present disclosure or any of the other incorporated references, the non-incorporated portion of the present disclosure shall control, and the term or incorporated disclosure therein shall only control with respect to the reference in which the term is defined and/or the incorporated disclosure was present originally.

As will be apparent to those of skill in the art upon reading this disclosure, each of the individual embodiments described and illustrated herein has discrete components and features which can be readily separated from or combined with the features of any of the other several embodiments without departing from the scope or spirit of the present teachings. Any recited method can be carried out in the order of events recited or in any other order which is logically possible.

One with skill in the art will appreciate that the present invention is not limited in its application to the details of construction, the arrangements of components, category selections, weightings, pre-determined signal limits, or the steps set forth in the description or drawings herein. The invention is capable of other embodiments and of being practiced or being carried out in many different ways.

The practice of various embodiments of the present disclosure employs, unless otherwise indicated, conventional techniques of immunology, biochemistry, chemistry, molecular biology, microbiology, cell biology, genomics and recombinant DNA, which are within the skill of the art. See Green and Sambrook, MOLECULAR CLONING: A LABORATORY MANUAL, $4^{th}$ edition (2012); CURRENT PROTOCOLS IN MOLECULAR BIOLOGY (F. M. Ausubel, et al. eds., (1987));
the series METHODS IN ENZYMOLOGY (Academic Press, Inc.): PCR 2: A PRACTICAL APPROACH (M. J. MacPherson, B. D. Hames and G. R. Taylor eds. (1995)), Harlow and Lane, eds. (1988) ANTIBODIES, A LABORATORY MANUAL, and ANIMAL CELL CULTURE (R.I. Freshney, ed. (1987)).

OTHER EXEMPLARY EMBODIMENTS

The present invention includes a variety of embodiments, which can be combined in multiple ways as long as the various components do not contradict one another. The embodiments should be regarded as a single invention file: each filing has other filing as the references and is also referenced in its entirety and for all purpose, rather than as a discrete independent. These embodiments include not only the disclosures in the current file, but also the documents that are herein referenced, incorporated, or to which priority is claimed.

(1) Definitions

The terms used in describing the devices/apparatus, systems, and methods herein disclosed are defined in the current application, or in PCT Application (designating U.S.) Nos PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

The terms "CROF Card (or card)", "COF Card", "QMAX-Card", "Q-Card", "CROF device", "COF device", "QMAX-device", "CROF plates", "COF plates", and "QMAX-plates" are interchangeable, except that in some embodiments, the COF card does not comprise spacers; and the terms refer to a device that comprises a first plate and a second plate that are movable relative to each other into different configurations (including an open configuration and a closed configuration), and that comprises spacers (except some embodiments of the COF card) that regulate the spacing between the plates. The term "X-plate" refers to one of the two plates in a CROF card, wherein the spacers are fixed to this plate. More descriptions of the COF Card, CROF Card, and X-plate are given in the provisional application Ser. Nos. 62/456,065, filed on Feb. 7, 2017, which is incorporated herein in its entirety for all purposes.

(2) Sample

The devices/apparatus, systems, and methods herein disclosed can be applied to manipulation and detection of various types of samples. The samples are herein disclosed, listed, described, and/or summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

The devices, apparatus, systems, and methods herein disclosed can be used for samples such as but not limited to diagnostic samples, clinical samples, environmental samples and foodstuff samples. The types of sample include but are not limited to the samples listed, described and/or summarized in PCT Application (designating U.S.) Nos. PCT/US2016/045437 and PCT/US0216/051775, which were respectively filed on Aug. 10, 2016 and Sep. 14, 2016, and are hereby incorporated by reference by their entireties.

For example, in some embodiments, the devices, apparatus, systems, and methods herein disclosed are used for a sample that includes cells, tissues, bodily fluids and/or a mixture thereof. In some embodiments, the sample comprises a human body fluid. In some embodiments, the sample comprises at least one of cells, tissues, bodily fluids, stool, amniotic fluid, aqueous humour, vitreous humour, blood, whole blood, fractionated blood, plasma, serum, breast milk, cerebrospinal fluid, cerumen, chyle, chime, endolymph, perilymph, feces, gastric acid, gastric juice, lymph, mucus, nasal drainage, phlegm, pericardia! fluid, peritoneal fluid, pleural fluid, pus, rheum, saliva, sebum, semen, sputum, sweat, synovial fluid, tears, vomit, urine, and exhaled breath condensate.

In some embodiments, the devices, apparatus, systems, and methods herein disclosed are used for an environmental sample that is obtained from any suitable source, such as but not limited to: river, lake, pond, ocean, glaciers, icebergs, rain, snow, sewage, reservoirs, tap water, drinking water, etc.; solid samples from soil, compost, sand, rocks, concrete, wood, brick, sewage, etc.; and gaseous samples from the air, underwater heat vents, industrial exhaust, vehicular exhaust, etc. In certain embodiments, the environmental sample is fresh from the source; in certain embodiments, the environmental sample is processed. For example, samples that are not in liquid form are converted to liquid form before the subject devices, apparatus, systems, and methods are applied.

In some embodiments, the devices, apparatus, systems, and methods herein disclosed are used for a foodstuff sample, which is suitable or has the potential to become suitable for animal consumption, e.g., human consumption. In some embodiments, a foodstuff sample includes raw ingredients, cooked or processed food, plant and animal sources of food, preprocessed food as well as partially or fully processed food, etc. In certain embodiments, samples that are not in liquid form are converted to liquid form before the subject devices, apparatus, systems, and methods are applied.

The subject devices, apparatus, systems, and methods can be used to analyze any volume of the sample. Examples of the volumes include, but are not limited to, about 10 ml or less, 5 ml or less, 3 ml or less, 1 microliter ($\mu$l, also "ul" herein) or less, 500 $\mu$l or less, 300 $\mu$l or less, 250 $\mu$l or less, 200 $\mu$l or less, 170 $\mu$l or less, 150 $\mu$l or less, 125 $\mu$l or less, 100 $\mu$l or less, 75 $\mu$l or less, 50 $\mu$l or less, 25 $\mu$l or less, 20 $\mu$l or less, 15 $\mu$l or less, 10 $\mu$l or less, 5 $\mu$l or less, 3 $\mu$l or less, 1 $\mu$l or less, 0.5 $\mu$l or less, 0.1 $\mu$l or less, 0.05 $\mu$l or less, 0.001 $\mu$l or less, 0.0005 $\mu$l or less, 0.0001 $\mu$l or less, 10 pl or less, 1 pl or less, or a range between any two of the values.

In some embodiments, the volume of the sample includes, but is not limited to, about 100 $\mu$l or less, 75 $\mu$l or less, 50 $\mu$l or less, 25 $\mu$l or less, 20 $\mu$l or less, 15 $\mu$l or less, 10 $\mu$l or less, 5 $\mu$l or less, 3 $\mu$l or less, 1 $\mu$l or less, 0.5 $\mu$l or less, 0.1 $\mu$l or less, 0.05 $\mu$l or less, 0.001 $\mu$l or less, 0.0005 $\mu$l or less, 0.0001 $\mu$l or less, 10 pl or less, 1 pl or less, or a range between any two of the values. In some embodiments, the volume of the sample includes, but is not limited to, about 10 $\mu$l or less, 5 $\mu$l or less, 3 $\mu$l or less, 1 $\mu$l or less, 0.5 $\mu$l or less, 0.1 $\mu$l or less, 0.05 $\mu$l or less, 0.001 $\mu$l or less, 0.0005 $\mu$l or less, 0.0001 $\mu$l or less, 10 pl or less, 1 pl or less, or a range between any two of the values.

In some embodiments, the amount of the sample is about a drop of liquid. In certain embodiments, the amount of sample is the amount collected from a pricked finger or fingerstick. In certain embodiments, the amount of sample is the amount collected from a microneedle, micropipette or a venous draw.

In certain embodiments, the sample holder is configured to hold a fluidic sample. In certain embodiments, the sample holder is configured to compress at least part of the fluidic sample into a thin layer. In certain embodiments, the sample holder comprises structures that are configured to heat and/or cool the sample. In certain embodiments, the heating source provides electromagnetic waves that can be absorbed by certain structures in the sample holder to change the temperature of the sample. In certain embodiments, the signal sensor is configured to detect and/or measure a signal from the sample. In certain embodiments, the signal sensor is configured to detect and/or measure an analyte in the sample. In certain embodiments, the heat sink is configured to absorb heat from the sample holder and/or the heating source. In certain embodiments, the heat sink comprises a chamber that at least partly enclose the sample holder.

(3) Q-Card, Spacers and Uniform Sample Thickness

The devices/apparatus, systems, and methods herein disclosed can include or use Q-cards, spacers, and uniform sample thickness embodiments for sample detection, analysis, and quantification. In some embodiments, the Q-card comprises spacers, which help to render at least part of the sample into a layer of high uniformity. The structure, material, function, variation and dimension of the spacers, as well as the uniformity of the spacers and the sample layer, are herein disclosed, listed, described, and/or summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

The term "open configuration" of the two plates in a QMAX process means a configuration in which the two plates are either partially or completely separated apart and the spacing between the plates is not regulated by the spacers.

The term "closed configuration" of the two plates in a QMAX process means a configuration in which the plates are facing each other, the spacers and a relevant volume of the sample are between the plates, the relevant spacing between the plates, and thus the thickness of the relevant volume of the sample, is regulated by the plates and the spacers, wherein the relevant volume is at least a portion of an entire volume of the sample.

The term "a sample thickness is regulated by the plate and the spacers" in a QMAX process means that for a give condition of the plates, the sample, the spacer, and the plate compressing method, the thickness of at least a port of the sample at the closed configuration of the plates can be predetermined from the properties of the spacers and the plate.

The term "inner surface" or "sample surface" of a plate in a QMAX card refers to the surface of the plate that touches the sample, while the other surface (that does not touch the sample) of the plate is termed "outer surface".

The term "height" or "thickness" of an object in a QMAX process refers to, unless specifically stated, the dimension of the object that is in the direction normal to a surface of the plate. For example, spacer height is the dimension of the spacer in the direction normal to a surface of the plate, and the spacer height and the spacer thickness means the same thing.

The term "area" of an object in a QMAX process refers to, unless specifically stated, the area of the object that is parallel to a surface of the plate. For example, spacer area is the area of the spacer that is parallel to a surface of the plate.

The term of QMAX card refers the device that perform a QMAX (e.g. CROF) process on a sample, and have or not have a hinge that connect the two plates.

The term "QMAX card with a hinge and "QMAX card" are interchangeable.

The term "angle self-maintain", "angle self-maintaining", or "rotation angle self-maintaining" refers to the property of the hinge, which substantially maintains an angle between the two plates, after an external force that moves the plates from an initial angle into the angle is removed from the plates.

In using QMAX card, the two plates need to be open first for sample deposition. However, in some embodiments, the QMAX card from a package has the two plates are in contact each other (e.g., a close position), and to separate them is challenges, since one or both plates are very thing. To facilitate an opening of the QMAX card, opening notch or notches are created at the edges or corners of the first plate or both places, and, at the close position of the plates, a part of the second plate placed over the opening notch, hence in the notch of the first plate, the second plate can be lifted open without a blocking of the first plate.

In the QMAX assay platform, a QMAX card uses two plates to manipulate the shape of a sample into a thin layer (e.g., by compressing). In certain embodiments, the plate manipulation needs to change the relative position (termed: plate configuration) of the two plates several times by human hands or other external forces. There is a need to design the QMAX card to make the hand operation easy and fast.

In QMAX assays, one of the plate configurations is an open configuration, wherein the two plates are completely or partially separated (the spacing between the plates is not controlled by spacers) and a sample can be deposited. Another configuration is a closed configuration, wherein at least part of the sample deposited in the open configuration is compressed by the two plates into a layer of highly uniform thickness, the uniform thickness of the layer is confined by the inner surfaces of the plates and is regulated by the plates and the spacers. In some embodiments, the average spacing between the two plates is more than 300 um.

In a QMAX assay operation, an operator needs to first make the two plates to be in an open configuration ready for sample deposition, then deposit a sample on one or both of the plates, and finally close the plates into a close position. In certain embodiments, the two plates of a QMAX card are initially on top of each other and need to be separated to get into an open configuration for sample deposition. When one of the plate is a thin plastic film (175 um thick PMA), such separation can be difficult to perform by hand. The present invention intends to provide the devices and methods that make the operation of certain assays, such as the QMAX card assay, easy and fast.

In some embodiments, the QMAX device comprises a hinge that connect two or more plates together, so that the plates can open and close in a similar fashion as a book. In some embodiments, the material of the hinge is such that the hinge can self-maintain the angle between the plates after adjustment. In some embodiments, the hinge is configured to maintain the QMAX card in the closed configuration, such that the entire QMAX card can be slide in and slide out a card slot without causing accidental separation of the two plates. In some embodiments, the QMAX device comprises one or more hinges that can control the rotation of more than two plates.

In some embodiments, the hinge is made from a metallic material that is selected from a group consisting of gold, silver, copper, aluminum, iron, tin, platinum, nickel, cobalt, alloys, or any combination of thereof. In some embodiments, the hinge comprises a single layer, which is made from a polymer material, such as but not limited to plastics.

The polymer material is selected from the group consisting of acrylate polymers, vinyl polymers, olefin polymers, cellulosic polymers, noncellulosic polymers, polyester polymers, Nylon, cyclic olefin copolymer (COC), poly(methyl methacrylate) (PMMB), polycarbonate (PC), cyclic olefin polymer (COP), liquid crystalline polymer (LCP), polyamide (PB), polyethylene (PE), polyimide (PI), polypropylene (PP), poly(phenylene ether) (PPE), polystyrene (PS), polyoxymethylene (POM), polyether ether ketone (PEEK), polyether sulfone (PES), poly(ethylene phthalate) (PET), polytetrafluoroethylene (PTFE), polyvinyl chloride (PVC), polyvinylidene fluoride (PVDF), polybutylene terephthalate (PBT), fluorinated ethylene propylene (FEP), perfluoroalkoxyalkane (PFB), polydimethylsiloxane (PDMS), rubbers, or any combinations of thereof. In some embodiments, the polymer material is selected from polystyrene, PMMB, PC, COC, COP, other plastic, or any combination of thereof.

In essence, the term "spacers" or "stoppers" refers to, unless stated otherwise, the mechanical objects that set, when being placed between two plates, a limit on the minimum spacing between the two plates that can be reached when compressing the two plates together. Namely, in the compressing, the spacers will stop the relative movement of the two plates to prevent the plate spacing becoming less than a preset (i.e. predetermined) value.

The term "a spacer has a predetermined height" and "spacers have a predetermined inter-spacer distance" means, respectively, that the value of the spacer height and the inter spacer distance is known prior to a QMAX process. It is not predetermined, if the value of the spacer height and the inter-spacer distance is not known prior to a QMAX process. For example, in the case that beads are sprayed on a plate as spacers, where beads are landed at random locations of the plate, the inter-spacer distance is not predetermined. Another example of not predetermined inter spacer distance is that the spacers moves during a QMAX processes.

The term "a spacer is fixed on its respective plate" in a QMAX process means that the spacer is attached to a location of a plate and the attachment to that location is maintained during a QMAX (i.e. the location of the spacer on respective plate does not change) process. An example of "a spacer is fixed with its respective plate" is that a spacer is monolithically made of one piece of material of the plate, and the location of the spacer relative to the plate surface does not change during the QMAX process. An example of "a spacer is not fixed with its respective plate" is that a spacer is glued to a plate by an adhesive, but during a use of the plate, during the QMAX process, the adhesive cannot hold the spacer at its original location on the plate surface and the spacer moves away from its original location on the plate surface.

In some embodiments, human hands can be used to press the plates into a closed configuration; In some embodiments, human hands can be used to press the sample into a thin layer. The manners in which hand pressing is employed are described and/or summarized in PCT Application (designating U.S.) Nos. PCT/US2016/045437 filed on Aug. 10, 2016 and PCT/US0216/051775 filed on Sep. 14, 2016, and in U.S. Provisional Application Nos. 62/431,639 filed on Dec. 9, 2016, 62/456,287 filed on Feb. 8, 2017, 62/456,065 filed on Feb. 7, 2017, 62/456,504 filed on Feb. 8, 2017, and 62/460,062 filed on Feb. 16, 2017, which are all hereby incorporated by reference in their entireties.

In some embodiments, human hand can be used to manipulate or handle the plates of the QMAX device. In certain embodiments, the human hand can be used to apply an imprecise force to compress the plates from an open configuration to a closed configuration. In certain embodiments, the human hand can be used to apply an imprecise force to achieve high level of uniformity in the thickness of the sample (e.g. less than 5%, 10%, 15%, or 20% variability).

(4) Hinges, Opening Notches, Recessed Edge and Sliders

The devices/apparatus, systems, and methods herein disclosed can include or use Q-cards for sample detection, analysis, and quantification. In some embodiments, the Q-card comprises hinges, notches, recesses, and sliders, which help to facilitate the manipulation of the Q card and the measurement of the samples. The structure, material, function, variation and dimension of the hinges, notches, recesses, and sliders are herein disclosed, listed, described, and/or summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/431,639, which was filed on Dec. 9, 2016, U.S. Provisional Application No. 62/456,065, which was filed on Feb. 7, 2017, U.S. Provisional Application Nos. 62/456,287 and 62/456,504, which was filed on Feb. 8, 2017, and U.S. Provisional Application No. 62/539,660, which was filed on Aug. 1, 2017, all of which applications are incorporated herein in their entireties for all purposes.

In some embodiments, the QMAX device comprises opening mechanisms such as but not limited to notches on plate edges or strips attached to the plates, making is easier for a user to manipulate the positioning of the plates, such as but not limited to separating the plates of by hand.

In some embodiments, the QMAX device comprises trenches on one or both of the plates.

In certain embodiments, the trenches limit the flow of the sample on the plate.

(5) Q-Card and Adaptor

The devices/apparatus, systems, and methods herein disclosed can include or use Q-cards for sample detection, analysis, and quantification. In some embodiments, the Q-card is used together with an adaptor that is configured to accommodate the Q-card and connect to a mobile device so that the sample in the Q-card can be imaged, analyzed, and/or measured by the mobile device. The structure, material, function, variation, dimension and connection of the Q-card, the adaptor, and the mobile are herein disclosed, listed, described, and/or summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application Nos. 62/456,287 and 62/456,590, which were filed on Feb. 8, 2017, U.S. Provisional Application No. 62/456,504, which was filed on Feb. 8, 2017, U.S. Provisional Application No. 62/459,544, which was filed on Feb. 15, 2017, and U.S. Provisional Application Nos. 62/460,075 and 62/459,920, which were filed on Feb. 16, 2017, all of which applications are incorporated herein in their entireties for all purposes.

In some embodiments, the adaptor comprises a receptacle slot, which is configured to accommodate the QMAX device when the device is in a closed configuration. In certain embodiments, the QMAX device has a sample deposited therein and the adaptor can be connected to a mobile device (e.g. a smartphone) so that the sample can be read by the mobile device. In certain embodiments, the mobile device can detect and/or analyze a signal from the sample. In certain embodiments, the mobile device can capture images of the sample when the sample is in the QMAX device and positioned in the field of view (FOV) of a camera, which in certain embodiments, is part of the mobile device.

In some embodiments, the adaptor comprises optical components, which are configured to enhance, magnify, and/or optimize the production of the signal from the sample. In some embodiments, the optical components include parts that are configured to enhance, magnify, and/or optimize illumination provided to the sample. In certain embodiments, the illumination is provided by a light source that is part of the mobile device. In some embodiments, the optical components include parts that are configured to enhance, magnify, and/or optimize a signal from the sample.

(6) Smartphone Detection System

The devices/apparatus, systems, and methods herein disclosed can include or use Q-cards for sample detection, analysis, and quantification. In some embodiments, the Q-card is used together with an adaptor that can connect the Q-card with a smartphone detection system.

In some embodiments, the smartphone comprises a camera and/or an illumination source The smartphone detection system, as well the associated hardware and software are herein disclosed, listed, described, and/or summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application Nos. 62/456,287 and 62/456,590, which were filed on Feb. 8, 2017, U.S. Provisional Application No. 62/456,504, which was filed on Feb. 8, 2017, U.S. Provisional Application No. 62/459,544, which was filed on Feb. 15, 2017, and U.S. Provisional Application Nos. 62/460,075 and 62/459,920, which were filed on Feb. 16, 2017, all of which applications are incorporated herein in their entireties for all purposes.

In some embodiments, the smartphone comprises a camera, which can be used to capture images or the sample when the sample is positioned in the field of view of the camera (e.g. by an adaptor). In certain embodiments, the camera includes one set of lenses (e.g. as in iPhone™ 6). In certain embodiments, the camera includes at least two sets of lenses (e.g. as in iPhone™ 7). In some embodiments, the smartphone comprises a camera, but the camera is not used for image capturing.

In some embodiments, the smartphone comprises a light source such as but not limited to LED (light emitting diode). In certain embodiments, the light source is used to provide illumination to the sample when the sample is positioned in the field of view of the camera (e.g. by an adaptor). In some embodiments, the light from the light source is enhanced, magnified, altered, and/or optimized by optical components of the adaptor.

In some embodiments, the smartphone comprises a processor that is configured to process the information from the sample. The smartphone includes software instructions that, when executed by the processor, can enhance, magnify, and/or optimize the signals (e.g. images) from the sample. The processor can include one or more hardware components, such as a central processing unit (CPU), an application-specific integrated circuit (ASIC), an application-specific instruction-set processor (ASIP), a graphics processing unit (GPU), a physics processing unit (PPU), a digital signal processor (DSP), a field-programmable gate array (FPGA), a programmable logic device (PLO), a controller, a microcontroller unit, a reduced instruction-set computer (RISC), a microprocessor, or the like, or any combination thereof.

In some embodiments, the smartphone comprises a communication unit, which is configured and/or used to transmit data and/or images related to the sample to another device. Merely by way of example, the communication unit can use a cable network, a wireline network, an optical fiber network, a telecommunications network, an intranet, the Internet, a local area network (LAN), a wide area network (WAN), a wireless local area network (WLAN), a metropolitan area network (MAN), a wide area network (WAN), a public telephone switched network (PSTN), a Bluetooth network, a ZigBee network, a near field communication (NFC) network, or the like, or any combination thereof.

In some embodiments, the smartphone is an iPhone™, an Android™ phone, or a Windows™ phone.

(7) Detection Methods

The devices/apparatus, systems, and methods herein disclosed can include or be used in various types of detection methods. The detection methods are herein disclosed, listed, described, and/or summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application Nos. 62/456,287, 62/456,528, 62/456631, 62/456522, 62/456598, 62/456603, and 62/456,628, which were filed on Feb. 8, 2017, U.S. Provisional Application Nos. 62/459,276, 62/456,904, 62/457075, and 62/457,009, which were filed on Feb. 9, 2017, and U.S. Provisional Application Nos. 62/459,303, 62/459,337, and 62/459,598, which were filed on Feb. 15, 2017, and U.S. Provisional Application Nos. 62/460,083, 62/460,076, which were filed on Feb. 16, 2017, all of which applications are incorporated herein in their entireties for all purposes.

(8) Labels, Capture Agent and Detection Agent

The devices/apparatus, systems, and methods herein disclosed can employ various types of labels, capture agents, and detection agents that are used for analytes detection. The labels are herein disclosed, listed, described, and/or summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

In some embodiments, the label is optically detectable, such as but not limited to a fluorescence label. In some embodiments, the labels include, but are not limited to, IRDye800CW, Alexa 790, Dylight 800, fluorescein, fluorescein isothiocyanate, succinimidyl esters of carboxyfluorescein, succinimidyl esters of fluorescein, 5-isomer of fluorescein dichlorotriazine, caged carboxyfluorescein-alanine-carboxamide, Oregon Green 488, Oregon Green 514; Lucifer Yellow, acridine Orange, rhodamine, tetramethylrhodamine, TEXAS RED®, propidium iodide, JC-1 (5,5',6, 6'-tetrachloro-1,1',3,3'-tetraethylbenzimidazoylcarbocyanine iodide), tetrabromorhodamine 123, rhodamine 6G, TMRM (tetramethyl rhodamine methyl ester), TMRE (tetramethyl rhodamine ethyl ester), tetramethylrosamine, rhodamine Band 4-dimethylaminotetramethylrosamine, green fluorescent protein, blue-shifted green fluorescent protein, cyan-shifted green fluorescent protein, red-shifted green fluorescent protein, yellow-shifted green fluorescent protein, 4-acetamido-4'-isothiocyanatostilbene-2,2'disulfonic acid; acridine and derivatives, such as acridine, acridine isothiocyanate; 5-(2'-aminoethyl)aminonaphthalene-1-sulfonic acid (EDANS); 4-amino-N-[3-vinylsulfonyl)phenyl]naphthalimide-3,5 disulfonate; N-(4-anilino-1-naphthyl)maleimide; anthranilamide; 4,4-difluoro-5-(2-thienyl)-4-bora-3a,4a diaza-5-indacene-3-propioni-c acid BODIPY; cascade blue; Brilliant Yellow; coumarin and derivatives: coumarin, 7-amino-4-methylcoumarin (AMC, Coumarin 120), 7-amino-4-trifluoromethylcoumarin (Coumarin 151); cyanine dyes; cyanosine; 4',6-diaminidino-2-phenylindole (DAPI); 5',5''-dibromopyrogallol-sulfonaphthalein (Bromopyrogallol Red); 7-diethylamino-3-(4'-isothiocyanatophenyl)-4-methylcoumarin; diethylenetriaamine pentaacetate; 4,4'-diisothiocyanatodihydro-stilbene-2-,2'-disulfonic acid; 4,4'-diisothiocyanatostilbene-2,2'-disulfonic acid; 5-(dimethylamino ]naphthalene-1-sulfonyl chloride (DNS, dansylchloride); 4-dimethylaminophenylazophenyl-4'-isothiocyanate (DABITC); eosin and derivatives: eosin, eosin isothiocyanate, erythrosin and derivatives: erythrosin B, erythrosin, isothiocyanate; ethidium; fluorescein and derivatives: 5-carboxyfluorescein (FAM), 5-(4,6-dichlorotriazin-2-yl)amino-fluorescein (DTAF), 2', ?'dimethoxy-4'5'-dichloro-6-carboxyfluorescein (JOE), fluorescein, fluorescein isothiocyanate, QFITC, (XRITC); fluorescamine; IR144; IR1446; Malachite Green isothiocyanate; 4-methylumbelliferoneortho cresolphthalein; nitrotyrosine; pararosaniline; Phenol Red; B-phycoerythrin; o-phthaldialdehyde; pyrene and derivatives: pyrene, pyrene butyrate, succinimidyl 1-pyrene;
butyrate quantum dots; Reactive Red 4 (Cibacron™ Brilliant Red 3B-A) rhodamine and derivatives: 6-carboxy-X-rhodamine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of sulforhodamine 101 (TEXAS RED®); N,N, N',N'-tetramethyl-6-carboxyrhodamine (TAMRA); tetramethyl rhodamine;
tetramethyl hodamine isothiocyanate (TRITC); riboflavin; 5-(2'-aminoethyl) aminonaphthalene-1-sulfonic acid (EDANS), 4-(4'-dimethylaminophenylazo)benzoic acid (DABCYL), rosolic acid; CAL Fluor Orange 560; terbium chelate derivatives; Cy 3; Cy 5; Cy 5.5; Cy 7; IRD 700; IRD 800; La Jolla Blue; phthalo cyanine; and naphthalo cyanine, coumarins and related dyes, xanthene dyes such as rhodols, resorufins, bimanes, acridines, isoindoles, dansyl dyes, aminophthalic
hydrazides such as luminol, and isoluminol derivatives, aminophthalimides, aminonaphthalimides, aminobenzofurans, aminoquinolines, dicyanohydroquinones, fluorescent europium and terbium complexes; combinations thereof, and the like. Suitable fluorescent proteins and chromogenic proteins include, but are not limited to, a green fluorescent protein (GFP), including, but not limited to, a GFP derived from Aequoria victoria or a derivative thereof, e.g., a "humanized" derivative such as Enhanced GFP; a GFP from another species such as *Renilla reniformis, Renilla mulleri*, or *Ptilosarcus guernyi*; "humanized" recombinant GFP (hrGFP); any of a variety of fluorescent and colored proteins from Anthozoan species; combinations thereof; and the like.

In any embodiment, the QMAX device can contain a plurality of capture agents and/or detection agents that each bind to a biomarker selected from Tables B1, B2, B3 and/or B7 in U.S. Provisional Application No. 62/234,538 and/or PCT Application No. PCT/US2016/054025, wherein the reading step d) includes obtaining a measure of the amount of the plurality of biomarkers in the sample, and wherein the amount of the plurality of biomarkers in the sample is diagnostic of a disease or condition.

In any embodiment, the capture agent and/or detection agents can be an antibody epitope and the biomarker can be an antibody that binds to the antibody epitope. In some embodiments, the antibody epitope includes a biomolecule, or a fragment thereof, selected from Tables B4, B5 or B6 in U.S. Provisional Application No. 62/234,538 and/or PCT Application No. PCT/US2016/054025. In some embodiments, the antibody epitope includes an allergen, or a fragment thereof, selected from Table B5. In some embodiments, the antibody epitope includes an infectious agent-derived biomolecule, or a fragment thereof, selected from Table B6 in U.S. Provisional Application No. 62/234,538 and/or PCT Application No. PCT/US2016/054025.

In any embodiment, the QMAX device can contain a plurality of antibody epitopes selected from Tables B4, B5 and/or B6 in U.S. Provisional Application No. 62/234,538 and/or PCT Application No. PCT/US2016/054025, wherein the reading step d) includes obtaining a measure of the amount of a plurality of epitope-binding antibodies in the sample, and wherein the amount of the plurality of epitope-binding antibodies in the sample is diagnostic of a disease or condition.

(9) Analytes

The devices/apparatus, systems, and methods herein disclosed can be applied to manipulation and detection of various types of analytes (including biomarkers). The analytes are herein disclosed, listed, described, and/or summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

The devices, apparatus, systems, and methods herein disclosed can be used for the detection, purification and/or quantification of various analytes. In some embodiments, the analytes are biomarkers that associated with various diseases. In some embodiments, the analytes and/or biomarkers are indicative of the presence, severity, and/or stage of the diseases.

The analytes, biomarkers, and/or diseases that can be detected and/or measured with the devices, apparatus, systems, and/or method of the present invention include the analytes, biomarkers, and/or diseases listed, described and/or summarized in PCT Application (designating U.S.) Nos. PCT/US2016/045437 filed on Aug. 10, 2016, and PCT Application No. PCT/US2016/054025 filed on Sep. 27, 2016, and U.S. Provisional Application Nos. 62/234,538 filed on Sep. 29, 2015, 62/233,885 filed on Sep. 28, 2015, 62/293,188 filed on Feb. 9, 2016, and 62/305,123 filed on Mar. 8, 2016, which are all hereby incorporated by reference by their entireties. For example, the devices, apparatus, systems, and methods herein disclosed can be used in (a) the detection, purification and quantification of chemical compounds or biomolecules that correlates with the stage of certain diseases, e.g., infectious and parasitic disease, injuries, cardiovascular disease, cancer, mental disorders, neuropsychiatric disorders and organic diseases, e.g., pulmonary diseases, renal diseases, (b) the detection, purification and quantification of microorganism, e.g., virus, fungus and bacteria from environment, e.g., water, soil, or biological samples, e.g., tissues, bodily fluids, (c) the detection, quantification of chemical compounds or biological samples that pose hazard to food safety or national security, e.g. toxic waste, anthrax, (d) quantification of vital parameters in medical or physiological monitor, e.g., glucose, blood oxygen level, total blood count, (e) the detection and quantification of specific DNA or RNA from biosamples, e.g., cells, viruses, bodily fluids, (f) the sequencing and comparing of genetic sequences in DNA in the chromosomes and mitochondria for genome analysis or (g) to detect reaction products, e.g., during synthesis or purification of pharmaceuticals.

In some embodiments, the analyte can be a biomarker, an environmental marker, or a foodstuff marker. The sample in some instances is a liquid sample, and can be a diagnostic sample (such as saliva, serum, blood, sputum, urine, sweat, lacrima, semen, or mucus); an environmental sample obtained from a river, ocean, lake, rain, snow, sewage, sewage processing runoff, agricultural runoff, industrial runoff, tap water or drinking water; or a foodstuff sample obtained from tap water, drinking water, prepared food, processed food or raw food.

In any embodiment, the sample can be a diagnostic sample obtained from a subject, the analyte can be a biomarker, and the measured the amount of the analyte in the sample can be diagnostic of a disease or a condition.

In any embodiment, the devices, apparatus, systems, and methods in the present invention can further include diagnosing the subject based on information including the measured amount of the biomarker in the sample. In some cases, the diagnosing step includes sending data containing the measured amount of the biomarker to a remote location and receiving a diagnosis based on information including the measurement from the remote location.

In any embodiment, the biomarker can be selected from Tables B1, 2, 3 or 7 as disclosed in U.S. Provisional Application Nos. 62/234,538, 62/293,188, and/or 62/305,123, and/or PCT Application No. PCT/US2016/054,025, which are all incorporated in their entireties for all purposes. In some instances, the biomarker is a protein selected from Tables B1, 2, or 3. In some instances, the biomarker is a nucleic acid selected from Tables B2, 3 or 7. In some instances, the biomarker is an infectious agent-derived biomarker selected from Table B2. In some instances, the biomarker is a microRNA (miRNA) selected from Table B7.

In any embodiment, the applying step b) can include isolating miRNA from the sample to generate an isolated miRNA sample, and applying the isolated miRNA sample to the disk-coupled dots-on-pillar antenna (QMAX device) array.

In any embodiment, the QMAX device can contain a plurality of capture agents that each bind to a biomarker selected from Tables B1, B2, B3 and/or B7, wherein the reading step d) includes obtaining a measure of the amount of the plurality of biomarkers in the sample, and wherein the amount of the plurality of biomarkers in the sample is diagnostic of a disease or condition.

In any embodiment, the capture agent can be an antibody epitope and the biomarker can be an antibody that binds to the antibody epitope. In some embodiments, the antibody epitope includes a biomolecule, or a fragment thereof, selected from Tables B4, B5 or B6. In some embodiments, the antibody epitope includes an allergen, or a fragment thereof, selected from Table B5. In some embodiments, the antibody epitope includes an infectious agent-derived biomolecule, or a fragment thereof, selected from Table B6.

In any embodiment, the QMAX device can contain a plurality of antibody epitopes selected from Tables B4, B5 and/or B6, wherein the reading step d) includes obtaining a measure of the amount of a plurality of epitope-binding antibodies in the sample, and wherein the amount of the plurality of epitope-binding antibodies in the sample is diagnostic of a disease or condition.

In any embodiment, the sample can be an environmental sample, and wherein the analyte can be an environmental marker. In some embodiments, the environmental marker is selected from Table B8 in U.S. Provisional Application No. 62/234,538 and/or PCT Application No. PCT/US2016/054025.

In any embodiment, the method can include receiving or providing a report that indicates the safety or harmfulness for a subject to be exposed to the environment from which the sample was obtained.

In any embodiment, the method can include sending data containing the measured amount of the environmental marker to a remote location and receiving a report that indicates the safety or harmfulness for a subject to be exposed to the environment from which the sample was obtained.

In any embodiment, the QMAX device array can include a plurality of capture agents that each binds to an environmental marker selected from Table B8, and wherein the reading step d) can include obtaining a measure of the amount of the plurality of environmental markers in the sample.

In any embodiment, the sample can be a foodstuff sample, wherein the analyte can be a foodstuff marker, and wherein the amount of the foodstuff marker in the sample can correlate with safety of the foodstuff for consumption. In some embodiments, the foodstuff marker is selected from Table B9.

In any embodiment, the method can include receiving or providing a report that indicates the safety or harmfulness for a subject to consume the foodstuff from which the sample is obtained. In any embodiment, the method can include sending data containing the measured amount of the foodstuff marker to a remote location and receiving a report that indicates the safety or harmfulness for a subject to consume the foodstuff from which the sample is obtained.

In any embodiment, the devices, apparatus, systems, and methods herein disclosed can include a plurality of capture agents that each binds to a foodstuff marker selected from Table B9 from in U.S. Provisional Application No. 62/234,538 and PCT Application No. PCT/US2016/054025, wherein the obtaining can include obtaining a measure of the amount of the plurality of foodstuff markers in the sample, and wherein the amount of the plurality of foodstuff marker in the sample can correlate with safety of the foodstuff for consumption.

Also provided herein are kits that find use in practicing the devices, systems and methods in the present invention.

The amount of sample can be about a drop of a sample. The amount of sample can be the amount collected from a pricked finger or fingerstick. The amount of sample can be the amount collected from a microneedle or a venous draw.

A sample can be used without further processing after obtaining it from the source, or can be processed, e.g., to enrich for an analyte of interest, remove large particulate matter, dissolve or resuspend a solid sample, etc.

Any suitable method of applying a sample to the QMAX device can be employed. Suitable methods can include using a pipette, dropper, syringe, etc. In certain embodiments, when the QMAX device is located on a support in a dipstick format, as described below, the sample can be applied to the QMAX device by dipping a sample-receiving area of the dipstick into the sample.

A sample can be collected at one time, or at a plurality of times. Samples collected over time can be aggregated and/or processed (by applying to a QMAX device and obtaining a measurement of the amount of analyte in the sample, as described herein) individually. In some instances, measurements obtained over time can be aggregated and can be useful for longitudinal analysis over time to facilitate screening, diagnosis, treatment, and/or disease prevention.

Washing the QMAX device to remove unbound sample components can be done in any convenient manner, as described above. In certain embodiments, the surface of the QMAX device is washed using binding buffer to remove unbound sample components.

Detectable labeling of the analyte can be done by any convenient method. The analyte can be labeled directly or indirectly. In direct labeling, the analyte in the sample is labeled before the sample is applied to the QMAX device. In indirect labeling, an unlabeled analyte in a sample is labeled after the sample is applied to the QMAX device to capture the unlabeled analyte, as described below.

(10) Applications

The devices/apparatus, systems, and methods herein disclosed can be used for various applications (fields and samples). The applications are herein disclosed, listed, described, and/or summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

In some embodiments, the devices, apparatus, systems, and methods herein disclosed are used in a variety of different application in various field, wherein determination of the presence or absence, quantification, and/or amplification of one or more analytes in a sample are desired. For example, in certain embodiments the subject devices, apparatus, systems, and methods are used in the detection of proteins, peptides, nucleic acids, synthetic compounds, inorganic compounds, organic compounds, bacteria, virus, cells, tissues, nanoparticles, and other molecules, compounds, mixtures and substances thereof. The various fields in which the subject devices, apparatus, systems, and methods can be used include, but are not limited to: diagnostics, management, and/or prevention of human diseases and conditions, diagnostics, management, and/or prevention of veterinary diseases and conditions, diagnostics, management, and/or prevention of plant diseases and conditions, agricultural uses, veterinary uses, food testing, environments testing and decontamination, drug testing and prevention, and others.

The applications of the present invention include, but are not limited to: (a) the detection, purification, quantification, and/or amplification of chemical compounds or biomolecules that correlates with certain diseases, or certain stages of the diseases, e.g., infectious and parasitic disease, injuries, cardiovascular disease, cancer, mental disorders, neuropsychiatric disorders and organic diseases, e.g., pulmonary diseases, renal diseases, (b) the detection, purification, quantification, and/or amplification of cells and/or microorganism, e.g., virus, fungus and bacteria from the environment, e.g., water, soil, or biological samples, e.g., tissues, bodily fluids, (c) the detection, quantification of chemical compounds or biological samples that pose hazard to food safety, human health, or national security, e.g. toxic waste, anthrax, (d) the detection and quantification of vital parameters in medical or physiological monitor, e.g., glucose, blood oxygen level, total blood count, (e) the detection and quantification of specific DNA or RNA from biological samples, e.g., cells, viruses, bodily fluids, (f) the sequencing and comparing of genetic sequences in DNA in the chromosomes and mitochondria for genome analysis or (g) the detection and quantification of reaction products, e.g., during synthesis or purification of pharmaceuticals.

In some embodiments, the subject devices, apparatus, systems, and methods are used in the detection of nucleic acids, proteins, or other molecules or compounds in a sample. In certain embodiments, the devices, apparatus, systems, and methods are used in the rapid, clinical detection and/or quantification of one or more, two or more, or three or more disease biomarkers in a biological sample, e.g., as being employed in the diagnosis, prevention, and/or management of a disease condition in a subject. In certain embodiments, the devices, apparatus, systems, and methods are used in the detection and/or quantification of one or more, two or more, or three or more environmental markers in an environmental sample, e.g., sample obtained from a river, ocean, lake, rain, snow, sewage, sewage processing runoff, agricultural runoff, industrial runoff, tap water or drinking water. In certain embodiments, the devices, apparatus, systems, and methods are used in the detection and/or quantification of one or more, two or more, or three or more foodstuff marks from a food sample obtained from tap water, drinking water, prepared food, processed food or raw food.

In some embodiments, the subject device is part of a microfluidic device. In some embodiments, the subject devices, apparatus, systems, and methods are used to detect a fluorescence or luminescence signal. In some embodiments, the subject devices, apparatus, systems, and methods include, or are used together with, a communication device, such as but not limited to: mobile phones, tablet computers and laptop computers. In some embodiments, the subject devices, apparatus, systems, and methods include, or are used together with, an identifier, such as but not limited to an optical barcode, a radio frequency ID tag, or combinations thereof.

In some embodiments, the sample is a diagnostic sample obtained from a subject, the analyte is a biomarker, and the measured amount of the analyte in the sample is diagnostic of a disease or a condition. In some embodiments, the subject devices, systems and methods further include receiving or providing to the subject a report that indicates the measured amount of the biomarker and a range of measured values for the biomarker in an individual free of or at low risk of having the disease or condition, wherein the measured amount of the biomarker relative to the range of measured values is diagnostic of a disease or condition.

In some embodiments, the sample is an environmental sample, and wherein the analyte is an environmental marker. In some embodiments, the subject devices, systems and methods includes receiving or providing a report that indicates the safety or harmfulness for a subject to be exposed to the environment from which the sample was obtained. In some embodiments, the subject devices, systems and methods include sending data containing the measured amount of the environmental marker to a remote location and receiving a report that indicates the safety or harmfulness for a subject to be exposed to the environment from which the sample was obtained. In some embodiments, the sample is a foodstuff sample, wherein the analyte is a foodstuff marker, and wherein the amount of the foodstuff marker in the sample correlate with safety of the foodstuff for consumption. In some embodiments, the subject devices, systems and methods include receiving or providing a report that indicates the safety or harmfulness for a subject to consume the foodstuff from which the sample is obtained. In some embodiments, the subject devices, systems and methods include sending data containing the measured amount of the foodstuff marker to a remote location and receiving a report that indicates the safety or harmfulness for a subject to consume the foodstuff from which the sample is obtained.

(11) Dimensions

The devices, apparatus, systems, and methods herein disclosed can include or use a QMAX device, which can comprise plates and spacers. In some embodiments, the dimension of the individual components of the QMAX device and its adaptor are listed, described and/or summarized in PCT Application (designating U.S.) No. PCT/US2016/045437 filed on Aug. 10, 2016, and U.S Provisional Application Nos. 62/431,639 filed on Dec. 9, 2016 and 62/456,287 filed on Feb. 8, 2017, which are all hereby incorporated by reference by their entireties.

In some embodiments, the dimensions are listed in the Tables below.

| | Plates: | |
|---|---|---|
| Parameters | Embodiments | Preferred Embodiments |
| Shape | round, ellipse, rectangle, triangle, polygonal, ring-shaped, or any superposition of these shapes; the two (or more) plates of the QMAX card can have the same size and/or shape, or different size and/or shape; | at least one of the two (or more) plates of the QMAX card has round corners for user safety concerns, wherein the round corners have a diameter of 100 um or less, 200 um or less, 500 um or less, 1mm or less, 2 mm or less, 5 mm or less, 10 mm or less, 50 mm or less, or in a range between any two of the values. |
| Thickness | the average thickness for at least one of the plates is 2 nm or less, 10 nm or less, 100 nm or less, 200 nm or less, 500 nm or less, 1000 nm or less, 2 μm (micron) or less, 5 μm or less, 10 μm or less, 20 μm or less, 50 μm or less, 100 μm or less, 150 μm or less, 200 μm or less, 300 μm or less, 500 μm or less, 800 μm or less, 1 mm (millimeter) or less, 2 mm or less, 3 mm or less, 5 mm or less, 10 mm or less, 20 mm or less, 50 mm or less, 100 mm or less, 500 mm or less, or in a range between any two of these values | For at least one of the plates is in the range of 0.5 to 1.5 mm; around 1 mm; in the range of 0.15 to 0.2 mm; or around 0.175 mm |
| Lateral Area | For at least one of the plate is 1 mm2 (square millimeter) or less, 10 mm2 or less, 25 mm2 or less, 50 mm2 or less, 75 mm2 or less, 1 cm2 (square centimeter) or less, 2 cm2 or less, 3 cm2 or less, 4 cm2 or less, 5 cm2 or less, 10 cm2 or less, 100 cm2 or less, 500 cm2 or less, 1000 cm2 or less, 5000 cm2 or less, 10,000 cm2 or less, 10,000 cm2 or less, or in a range between any two of these values | For at least one plate of the QMAX card is in the range of 500 to 1000 mm$^2$; or around 750 mm$^2$ |
| Lateral Linear Dimension (width, length, or diameter, etc.) | For at least one of the plates of the QMAX card is 1 mm or less, 5 mm or less, 10 mm or less, 15 mm or less, 20 mm or less, 25 mm or less, 30 mm or less, 35 mm or less, 40 mm or less, 45 mm or less, 50 mm or less, 100 mm or less, 200 mm or less, 500 mm or less, 1000 mm or less, 5000 mm or less, or in a range between any two of these values | For at least one plate of the QMAX card is in the range of 20 to 30 mm; or around 24 mm |
| Recess width | 1 um or less, 10 um or less, 20 um or less, 30 um or less, 40 um or less, 50 um or less, 100 um or less, 200 um or less, 300 um or less, 400 um or less, 500 um or less, 7500 um or less, 1 mm or less, 5 mm or less, 10 mm or less, 100 mm or less, or 1000 mm or less, or in a range between any two of these values. | In the range of 1 mm to 10 mm; Or About 5 mm |

| Hinge: | | |
|---|---|---|
| Parameters | Embodiments | Preferred Embodiments |
| Number | 1, 2, 3, 4, 5, or more | 1 or 2 |
| Length of Hinge Joint | 1 mm or less, 2 mm or less, 3 mm or less, 4 mm or less, 5 mm or less, 10 mm or less, 15 mm or less, 20 mm or less, 25 mm or less, 30 mm or less, 40 mm or less, 50 mm or less, 100 mm or less, 200 mm or less, or 500 mm or less, or in a range between any two of these values | In the range of 5 mm to 30 mm. |
| Ratio (hinge joint length vs. aligning plate edge length | 1.5 or less, 1 or less, 0.9 or less, 0.8 or less, 0.7 or less, 0.6 or less, 0.5 or less, 0.4 or less, 0.3 or less, 0.2 or less, 0.1 or less, 0.05 or less or in a range between any two of these values. | In the range of 0.2 to 1; or about 1 |
| Area | 1 $mm^2$ or less, 5 $mm^2$ or less, 10 $mm^2$ or less, 20 $mm^2$ or less, 30 $mm^2$ or less, 40 $mm^2$ or less, 50 $mm^2$ or less, 100 $mm^2$ or less, 200 $mm^2$ or less, 500 $mm^2$ or less, or in a range between any of the two values | In the range of 20 to 200 $mm^2$; or about 120 $mm^2$ |
| Ratio (hinge area vs. plate area) | 1 or less, 0.9 or less, 0.8 or less, 0.7 or less, 0.6 or less, 0.5 or less, 0.4 or less, 0.3 or less, 0.2 or less, 0.1 or less, 0.05 or less, 0.01 or less or in a range between any two of these values | In the range of 0.05 to 0.2, around 0.15 |
| Max. Open Degree | 15 or less, 30 or less, 45 or less, 60 or less, 75 or less, 90 or less, 105 or less, 120 or less, 135 or less, 150 or less, 165 or less, 180 or less, 195 or less, 210 or less, 225 or less, 240 or less, 255 or less, 270 or less, 285 or less, 300 or less, 315 or less, 330 or less, 345 or less or 360 or less degrees, or in a range between any two of these values | In the range of 90 to 180 degrees |
| No. of Layers | 1, 2, 3, 4, 5, or more | 1 or 2 |
| Layer thickness | 0.1 um or less, 1 um or less, 2 um or less, 3 um or less, 5 um or less, 10 um or less, 20 um or less, 30 um or less, 50 um or less, 100 um or less, 200 um or less, 300 um or less, 500 um or less, 1 mm or less, 2 mm or less, and a range between any two of these values | In the range of 20 um to 1 mm; or around 50 um |
| Angle-maintaining | Limiting the angle adjustment with no more than ±90, ±45, ±30, ±25, ±20, ±15, ±10, ±8, ±6, ±5, ±4, ±3, ±2, or ±1, or in a range between any two of these values | No more than ±2 |

| Notch: | | |
|---|---|---|
| Parameters | Embodiments | Preferred Embodiments |
| Number | 1, 2, 3, 4, 5, or more | 1 or 2 |
| Shape | round, ellipse, rectangle, triangle, polygon, ring-shaped, or any superposition or portion of these shapes. | Part of a circle |
| Positioning | Any location along any edge except the hingeedge, or any corner joint by non-hinge edges | |
| Lateral Linear Dimension (Length along the edge, radius, etc.) | 1 mm or less, 2.5 mm or less, 5 mm or less, 10 mm or less, 15 mm or less, 20 mm or less, 25 mm or less, 30 mm or less, 40 mm or less, 50 mm or less, or in a range between any two of these values | In the range of 5 mm to 15 mm; or about 10 mm |
| Area | 1 $mm^2$ (square millimeter) or less, 10 $mm^2$ or less, 25 $mm^2$ or less, 50 $mm^2$ or less, 75 $mm^2$ or less or in a range between any two of these values. | In the range of 10 to 150 $mm^2$, or about 50 $mm^2$ |

Trench:

| Parameters | Embodiments | Preferred Embodiments |
|---|---|---|
| Number | 1, 2, 3, 4, 5, or more | 1 or 2 |
| Shape | Closed (round, ellipse, rectangle, triangle, polygon, ring-shaped, or any superposition or portion of these shapes) or open-ended (straight line, curved line, arc, branched tree, or any other shape with open endings); | |
| Length | 0.001 mm or less, 0.005 mm or less, 0.01 mm or less, 0.05 mm or less, 0.1 mm or less, 0.5 mm or less, 1 mm or less, 2 mm or less, 5 mm or less, 10 mm or less, 20 mm or less, 50 mm or less, 100 mm or less, or in a range between any two of these values | |
| Cross-sectional Area | 0.001 mm$^2$ or less, 0.005 mm$^2$ or less, 0.01 mm$^2$ or less, 0.05 mm$^2$ or less, 0.1 mm$^2$ or less, 0.5 mm$^2$ or less, 1 mm$^2$ or less, 2 mm$^2$ or less, 5 mm$^2$ or less, 10 mm$^2$ or less, 20 mm$^2$ or less, or in a range between any two of these values. | |
| Volume | 0.1 ul or more, 0.5 ul or more, 1 ul or more, 2 ul or more, 5 ul or more, 10 ul or more, 30 ul or more, 50 ul or more, 100 ul or more, 500 ul or more, 1 ml or more, or in a range between any two of these values | In the range of 1 ul to 20 ul; or about 5 ul |

Receptacle Slot

| Parameters | Embodiments | Preferred Embodiments |
|---|---|---|
| Shape of receiving area | round, ellipse, rectangle, triangle, polygon, ring-shaped, or any superposition of these shapes; | |
| Difference between sliding track gap size and card thickness | 100 nm, 500 nm, 1 um, 2 um, 5 um, 10 um, 50 um, 100 um, 300 um, 500 um, 1 mm, 2 mm, 5 mm, 1 cm, or in a range between any two of the values. | In the range of 50 to 300 um; or about 75 um |
| Difference between receiving area and card area | 1 mm$^2$ (square millimeter) or less, 10 mm$^2$ or less, 25 mm$^2$ or less, 50 mm$^2$ or less, 75 mm$^2$ or less, 1 cm$^2$ (square centimeter) or less, 2 cm$^2$ or less, 3 cm$^2$ or less, 4 cm$^2$ or less, 5 cm$^2$ or less, 10 cm$^2$ or less, 100 cm$^2$ or less, or in a range between any of the two values. | |

(12) Cloud

The devices/apparatus, systems, and methods herein disclosed can employ cloud technology for data transfer, storage, and/or analysis. The related cloud technologies are herein disclosed, listed, described, and/or summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

In some embodiments, the cloud storage and computing technologies can involve a cloud database. Merely by way of example, the cloud platform can include a private cloud, a public cloud, a hybrid cloud, a community cloud, a distributed cloud, an inter-cloud, a multi-cloud, or the like, or any combination thereof. In some embodiments, the mobile device (e.g. smartphone) can be connected to the cloud through any type of network, including a local area network (LAN) or a wide area network (WAN).

In some embodiments, the data (e.g. images of the sample) related to the sample is sent to the cloud without processing by the mobile device and further analysis can be conducted remotely. In some embodiments, the data related to the sample is processed by the mobile device and the results are sent to the cloud. In some embodiments, both the raw data and the results are transmitted to the cloud.

What is claimed:

1. A method for analyzing an analyte in a sample, comprising:
   (a) obtaining a tissue sample containing or suspected of containing a target analyte;
   (b) obtaining a device comprising a first plate, a second plate, and spacers, wherein
      (i) the first and second plate are movable relative to each other into different configurations, including an open configuration and a closed configuration, and (ii) the spacers have a predetermined substantially uniform height that is equal to or less than about 200 microns, and a predetermined inter-spacer distance, and
(iii) each plate has a sample contact area on respective inner surface of the plate for contacting the sample;
(c) depositing, when the plates are in the open configuration, the sample on one or both of the plates;
(d) after (c), bringing the two plates together and pressing the plates into the closed configuration;
(e) imaging, using an imager, without washing the sample in the closed configuration, one or more images of the sample; and
(f) analyzing, using a machine learning model, the one or more images to detect the analyte,
wherein the open configuration is the configuration, in which: the two plates are partially or entirely separated apart, the spacing between the plates is not regulated by the spacers, and the tissue sample is deposited on one or both of the plates; and
wherein the closed configuration is the configuration that is configured after the open configuration; and in the closed configuration: at least part of the tissue sample and a layer of at least part of the staining liquid are between the two plates, wherein the thickness of the layer of at least part of the staining liquid is regulated by the plates, the tissue sample, and the spacers, and has an average distance between the sample surface and the surface of the plates that is equal to or less than 250 µm.

2. The method of claim 1, further comprising a use of reagent for detection of the analyte.

3. The method of claim 2, wherein the reagent comprises a labeled antibody and a dye.

4. The method of claim 1, further comprising a step of imaging the sample.

5. The method of claim 1, wherein said dye non-specifically binds to said target cell.

6. The method of claim 1, wherein said label on said labeled antibody and said dye are capable of excitation at the same wavelength.

7. The method of claim 3, wherein the analyte in the sample is chlamydia, wherein the antibody comprises a chlamydia-binding antibody, and the dye is a staining medium.

8. The method of claim 1, wherein the analyte comprises a protein, peptides, DNA, RNA, nucleic acid, or other molecules.

9. The method of claim 1, wherein the chlamydia antibody is fluorescently labeled.

10. The method of claim 1 wherein the layer has a thickness that is 10 µm.

11. The method of claim 1, wherein the layer has a thickness that is less than 50 µm.

12. The method of claim 1, wherein the layer has a thickness that is about 30 µm or less.

13. The method of claim 1, wherein the sample thickness between the two plates is 30 µm.

14. The method of claim 1, wherein the sample between the two plates has a thickness in the range of 1 µm to 35 µm.

15. A method of claim 1, wherein the analyte is CD4 (cluster of differentiation 4) in a blood sample.

16. The method of claim 1, wherein the antibody and/or the dye are coated on one of the first and second plates.

17. The method of claim 1, further comprising, after the plates are in the closed configuration, a step of imaging the sample, wherein the sample is imaged without washing.

18. The method of claim 1, wherein the layer has a thickness that is about equal to or less than 10 µm.

19. The method of claim 1, wherein the inter spacer distance between the spacers is periodic.

20. The method of claim 1, wherein one of the plates is flexible, wherein the fourth power of the inter-spacer-distance (ISD) divided by the thickness of the flexible plate (h) and the Young's modulus (E) of the flexible plate, $ISD^4/(hE)$, is equal to or less than $10^6$ µm$^3$/GPa, and the thickness of the flexible plate times the Young's modulus of the flexible plate is in the range of 60 to 750 GPa-µm.

21. The method of claim 1, wherein the sample is a biological sample selected from amniotic fluid, aqueous humour, vitreous humour, blood, breast milk, cerebrospinal fluid (CSF), cerumen (earwax), chyle, chime, endolymph, perilymph, feces, breath, gastric acid, gastric juice, lymph, mucus, pericardia! fluid, peritoneal fluid, pleural fluid, pus, rheum, saliva, exhaled breath condensates, sebum, semen, sputum, sweat, synovial fluid, tears, vomit, and urine.

22. The method of claim 1, wherein the first and second plates are connected by a hinge and are configured to be changed from the open configuration to the closed configuration by folding the plates along the hinge.

23. The method of claim 1, further comprising a step of using a mobile communication device comprising:
one or a plurality of cameras for the detecting and/or imaging the sample; electronics, signal processors, hardware and software for receiving and/or processing the detected signal and/or the image of the sample and for remote communication.

24. The method of claim 1, further comprising: a housing configured to hold the sample and to be mounted to the mobile communication device.

25. The method of claim 1, wherein the analyte comprises a molecule, cells, tissues, viruses, and nanoparticles with different shapes, wherein the molecule comprises a protein, peptides, DNA, RNA, nucleic.

26. The method of claim 1, wherein the inter-spacer distance between the spacers is in the range of 14 µm to 200 µm.

27. The method of claim 1, wherein the layer thickness of the at least a part of the sample is configured so that the sample is analyzed in 120 sec or less.

28. The method of claim 1, wherein the analyte is a cell.

29. The method of claim 28, wherein the cell is stained by a reagent.

30. The method of claim 29, wherein the reagent comprises a protein that specifically binds to the cell.

31. The method of claim 29, wherein the reagent comprises a nucleic acid that specifically binds to the cell.

32. The method of claim 1, further comprising a reagent that comprises a protein that specifically binds to the analyte.

33. The method of claim 1, further comprising a reagent that comprises a nucleic acid that specifically binds to the analyte.

34. The method of claim 1, wherein one or both plates comprise a location marker, a scale marker, an imaging marker, or any combination thereof.

35. The method of claim 1, wherein the spacers function as a location marker, a scale marker, an imaging marker, or any combination thereof.

36. The method of claim 1, wherein the spacers function as a location marker.

37. The method of claim 1, wherein the spacers function as a scale marker.

38. The method of claim 1, wherein the spacers function as an imaging marker.

39. The method of claim 1, wherein incubation time between the end of step (d) and the beginning of the step (e) is 60 seconds or less.

40. The method of claim 1, wherein incubation time between the end of step (d) and the beginning of the step (e) is 120 seconds or less.

41. The method of claim 1, wherein the machine learning model is a deep learning model.

42. The method of claim 1, wherein the machine learning model is a statistical model.

43. The method of claim 1, wherein the spacers are fabricated using injection molding, laser cutting the first plate, nanoimprinting, extrusion printing, or a combination of thereof.

* * * * *